United States Patent [19]

Hunter

[11] Patent Number: 5,554,372
[45] Date of Patent: Sep. 10, 1996

[54] METHODS AND VACCINES COMPRISING SURFACE-ACTIVE COPOLYMERS

[75] Inventor: Robert L. Hunter, Tucker, Ga.

[73] Assignee: Emory University, Atlanta, Ga.

[21] Appl. No.: 420,333

[22] Filed: Apr. 11, 1995

Related U.S. Application Data

[63] Continuation of Ser. No. 133,760, Oct. 7, 1993, abandoned, which is a continuation of Ser. No. 716,807, Jun. 21, 1991, abandoned, which is a continuation-in-part of Ser. No. 544,831, Jun. 27, 1990, abandoned, which is a continuation-in-part of Ser. No. 449,086, Dec. 8, 1989, abandoned, which is a continuation of Ser. No. 341,315, Apr. 21, 1989, abandoned, which is a continuation of Ser. No. 208,335, Jun. 17, 1988, abandoned, which is a continuation-in-part of Ser. No. 75,187, Jul. 16, 1987, abandoned, which is a continuation-in-part of Ser. No. 909,964, Sep. 22, 1986, abandoned.

[51] Int. Cl.$^6$ .......................... A61K 45/00; A61K 47/30
[52] U.S. Cl. .......................... 424/280.1; 424/278.1; 424/283.1; 424/279.1; 514/723; 514/772.3
[58] Field of Search .......................... 424/280.1, 283.1, 424/278.1, 279.1, 78.38; 514/723, 772.3

[56] References Cited

U.S. PATENT DOCUMENTS

| | | | |
|---|---|---|---|
| 2,674,619 | 4/1954 | Lundsted | 560/198 |
| 2,979,528 | 4/1961 | Lundsted | 564/505 |
| 3,022,335 | 2/1962 | Lundsted | 536/120 |
| 3,036,118 | 5/1962 | Jackson et al. | 560/182 |
| 3,867,521 | 2/1975 | Miskel et al. | 424/457 |
| 3,869,546 | 3/1975 | Lund | 424/78.18 |
| 3,869,549 | 3/1975 | Geller | 514/12 |
| 4,101,536 | 7/1978 | Yamamura et al. | 530/322 |
| 4,158,052 | 6/1979 | Audibert et al. | 424/45 |
| 4,185,089 | 6/1980 | Derrien et al. | 424/88 |
| 4,314,998 | 2/1982 | Yamamura et al. | 514/8 |
| 4,323,559 | 4/1982 | Audibert et al. | 514/8 |
| 4,323,560 | 4/1982 | Baschang et al. | 514/8 |
| 4,369,178 | 1/1983 | Yamamura et al. | 514/8 |
| 4,372,945 | 2/1983 | Likhite | 424/88 |
| 4,382,080 | 5/1983 | Shiba et al. | 514/8 |
| 4,400,376 | 8/1983 | Sanderson | 530/405 |
| 4,406,889 | 9/1983 | Hartmann et al. | 514/8 |
| 4,409,209 | 10/1983 | Baschang et al. | 514/8 |
| 4,423,038 | 12/1983 | Baschang et al. | 514/8 |
| 4,427,659 | 1/1984 | Le Francier et al. | 514/8 |
| 4,461,761 | 7/1984 | Le Francier et al. | 514/8 |
| 4,478,823 | 10/1984 | Sanderson | 503/405 |
| 4,503,036 | 5/1985 | Girardon et al. | 424/92 |
| 4,606,918 | 8/1986 | Allison et al. | 424/88 |
| 4,609,546 | 9/1986 | Hiratani | 424/88 |
| 4,770,874 | 9/1988 | Allison et al. | 424/88 |
| 4,803,070 | 2/1989 | Cantrell et al. | 424/92 |
| 4,806,352 | 2/1989 | Cantrell | 424/92 |
| 4,866,034 | 9/1989 | Ribi | 514/2 |
| 4,912,094 | 3/1990 | Myers et al. | 514/54 |

OTHER PUBLICATIONS

Abstract: Biosis Accession No. 64008712, Mancino, D. et al., "Adjuvant Effect of Amorphous Silica on the Immune Response to Various Antigens in Guinea-Pigs," Int. Arch. Allergy Appl. Immunol., vol. 53, No. 2, pp. 97–103 (1977).

Morrison et al., "Adjuvant-free immunological manipulation of livestock", Res. Vet. Sci., vol. 37, pp. 108–113 (1984).

Stevens, "A synthetic peptide vaccine against human chlorionic gonadotropin", Vaccines 86, pp. 39–44 (1986).

Pike et al., "A reappraisal of 'T-independent' antigens. I. Effect of lymphokines on the response of single adult hapten-specific B lymphocytes", J. Immunol., vol. 132, No. 4, pp. 1687–1695 (1984).

Feldmann, "Induction of immunity and tolerance in vitro by hapten protein conjugates. II. Carrier independence of the response to dinitrophenylated polymerized flagellin", Eur. J. Immunol., vol. 2, pp. 130–137 (1972).

Majarian et al., "Expression of heterologous epitopes as recombinant flagella on the surface of attenuated *Salmonella*", Vaccines 89, pp. 277–281 (1989).

Netwon et al., "Immune response to cholera toxin epitope inserted in *Salmonella* flagellin", Science, vol. 244, pp. 70–72 (1989).

Nossal et al., "Antigens in immunity. II. Immunogenic properties of flagella, polymerized flagellin and flagellin in the primary response", Aust. J. Exp. Biol. Med. Sci., vol. 42, pp. 283–294 (1964).

Kobayashi et al., "Purification and chemical properties of flagellin", Arch. Biochem. Biophys., vol. 84, pp. 342–362 (1959).

Feldmann et al., "The relationship between antigenic structure and the requirement for thymus-derived cells in the immune response", J. Exp. Med., vol. 134, pp. 103–119 (1971).

Lee et al., "Communications: Decline and spontaneous recovery of the monoclonal response to phosphorylcholine during repeated immunization", J. Immunol., vol. 113, No. 5, pp. 1644–1646 (1974).

Rietschel et al., "Bacterial endotoxins: Relationships between chemical structure and biological activity", Immunological Adjuvants & Vaccines, ed. Gregoriadis et al., Series A: Life Sciences vol. 179, pp. 61–74 ().

Galanos et al., "Biological activities and immunological properties of lipid A", Microbiology, pp. 269–276 (1977).

(List continued on next page.)

*Primary Examiner*—James C. Housel
*Assistant Examiner*—Jennifer Shaver
*Attorney, Agent, or Firm*—Jones & Askew

[57] ABSTRACT

The present invention comprises adjuvants which, when admixed with an antigen and administered into a human or animal, will induce a more intense immune response to the antigen than when the antigen is administered alone. In many cases, the adjuvant that is described as the present invention will increase overall titer of antibodies of a specific isotype which are specific for the antigen. For example, in mice, when the adjuvant of the present invention is admixed with a conventional antigen, the isotype that is induced in the mouse is changed from a predominantly IgG1 isotype to the more protective IgG2 isotype and, in some cases, IgG3 isotype. Thus, by practicing the present invention, one can improve the overall protective effect of conventional vaccines.

8 Claims, 17 Drawing Sheets

OTHER PUBLICATIONS

Haslberger et al., "Immunopharmacology of lipopolysaccharides (endotoxins) from gram–negative bacteria", Triangle, vol. 26, No. 1, pp. 33–49 (1987).

Louis et al., "Lipopolysaccharides: From immunostimulation to autoimmunity", Springer Semin. Immunopathol., vol. 2, pp. 215–228 (1979).

Qureshi, et al., "Purification and structural determination of nontoxic lipid A obtained from the lipopolysaccharide of *Salmonella Typhimurium*", J. Biol. Chem., vol. 257, No. 19, pp. 11808–11815 (1982).

Kotani et al., "Immunobiologically active lipid A analogs synthesized according to a revised structural model of natural lipid A", Infect. Immun., vol. 45, No. 1, pp. 293–296 (1984).

Ribi et al., "Lipid A and immunotherapy", Rev. Infect. Dis., vol. 6, No. 4, pp. 567–572 (1984).

Hadjipetrou–Kourounakis et al., "Adjuvants influence the immunoglobin subclass distribution of immune responses in vivo", Scand. J. Immunol., vol. 19, pp. 219–225 (1984).

Munford et al., "Detoxification of bacterial lipopolysaccharides (endotoxins) by a human neutrophil enzyme", Science, vol. 234, pp. 203–205 (1986).

Kanegasaki et al., "Structure–activity relationship of lipid A: Comparison of biological activities of natural and synthetic lipid A's with different fatty acid compositions", J. Biochem., vol. 99, pp. 1203–1210 (1986).

Hunter et al., "The adjuvant activity of nonionic block polymer surfactants. III. Characterization of selected biologically active surfaces", Scand. J. Immunol., vol. 23, pp. 287–300 (1986).

Hunter et al., "The adjuvant activity of nonionic block polymer surfactants. I. The role of hydrophile–lipophile balance", J. Immunol., vol. 127, No. 3, pp. 1244–1250 (1981).

Snippe et al., "Adjuvant effect of nonionic block polymer surfactants in humoral and cellular immunity", Int. Archs. Allery Appl. Immun., vol. 65, pp. 390–398 (1981).

Hunter et al., "Nonionic block copolymer surfactants as immunological adjuvants: Mechanisms of action and novel formulations", Immunological Adjuvants & Vaccines, ed. Gregoriadis et al., *Plenum Publishing Corp.*, pp. 133–144 (1989).

W. R. Clark, "The Properties and Fine Structure of Immunoglobulins", *The Experimental Foundations of Modern Immunology*, 3rd ed., John Wiley & Sons, pp. 62–74.

Hoffman et al., "Naturally acquired antibodies to sporozoites do not prevent malaria: Vaccine development implications", Science, vol. 237, pp. 639–642 (1987).

Egan et al., "Efficacy of murine malaria sporozoite vaccines: Implications for human vaccine development", Science, vol. 236, pp. 453–456 (1987).

Good et al., "Construction of synthetic immunogen: Use of new T–helper epitope on malaria circumsporozite protein", Science, vol. 235, pp. 1059–1062 (1987).

Hoffman et al., "Immunity to malaria and naturally acquired antibodies to the circumsporozoite protein of *plasmodium falciparum*", N. Engl. J. Med., vol. 315, No. 10, pp. 601–606 (1986).

Hunter, R. L., et al., "The Adjuvant Activity of Nonionic Block Polymer Surfactants II. Antibody Formulation and Inflammation Related to the Structure of Triblock and Octablock Copolymers", J. Immunol., vol. 133, pp. 3167–3175 (1984).

Schmolka, J. R., "A Review of Block Polymer Surfactants", J. Am. Oil Chemists' Soc., 54:110–116 (1977).

Block and Graft Copolymerization, vol. 2, edited by R. J. Ceresa, John Wiley & Sons, New York (1976).

Raetz, C. R. H., "Structure and Biosynthesis of Lipid A in *Escherichia coli*", Cellular and Molecular Biology, vol. 1, Neidhardt, F. C. Editor, American Society for Microbiology.

Liang, X, et al., "Oral Administration of Cholera Toxin–Sedai Virus Conjugate Potentiates Gut and Respiratory Immunity Against Sendai Virus", J. Immunol., vol. 141, No. 5, pp. 1495–1501 (1988).

Wechsler, D. S., et al., "Heat labile IgG2a antibodies affect cure of *Trypanosoma muculi* infection in C57BL/6 mice", J. Immunol. vol. 137, pp. 2968–2972 (1986).

Takehara, H. A., et al. "*Trypanosoma cruzi:* role of different antibody classes in protection against infection in the mouse", Exp. Parasitology, vol. 52, pp. 137–146 (1981).

Vukajlovich, et al., "Conversion of lipopolysaccharides to molecular aggregates with reduced subunit heterogeneity: Demonstration of LPS–responsiveness in 'Endotoxin–unresponsive C3H/HeJ splenocytes", J. Immunol., vol. 130, pp. 2804–2808 (1983).

Scott, M. T., et al., "Restricted IgG isotype profiles in *T. cruzi* infected mice and Chagas' disease patients", Clin. Exp. Immunol., vol. 58, pp. 372–379 (1984).

Raetz, C. R. H., et al., "Isolation and characterization of eight lipid A precursors from a 3–deoxy–D–manno–octylosonic acid deficient mutant of Salmonella typhimurium", J. Biol. Chem., vol. 260, pp. 16080–16088 (1985).

Karch, H., "Modulation of the IgG subclass responses to lipopolysaccharide by bacterial membrane components: Differential adjuvant effects produced by primary and secondary stimulation" J. Immun., vol. 131, pp. 6–8 (1983).

Galanos, C., et al., "A new method for the extraction of lipopolysaccharides", Eur. J. Biochem., vol. 9, pp. 245–249 (1969).

Ohta, M., "Adjuvant action of bacterial lipopolysaccharide in induction of delayed–type hypersensitivity to protein antigens: II. Relationships of Intensity of the action to that of other immunological activities", Immunobiol., vol. 163, pp. 400–469, (1982).

Takayama, K., et al., "Fatty Acyl Derivatives of Glucosamine 1 Phosphate in *Escherichia coli* and Their Relation to Lipid A", J. Biol. Chem., vol. 256, pp. 7379–7385 (1983).

Qureshi, N., et al., "Position of ester groups in the lipid A backbone of lipopolysaccharides obtained from *Salmonella typhimurium*", J. Biol. Chem., vol. 258, pp. 12947–12951 (1983).

Qureshi et al., *Molecular Basis of Bacterial Pathogenesis*, "Structure and function of lipid A", The Bacteria, vol. XI, *Academic Press, Inc.,* San Diego, Cal., eds. Iglewski et al., pp. 319–338 (1990).

Quershi, et al., "Application of fast atom bombardment mass spectrometry and nuclear magnetic resonance on the structural analysis of purified lipid A" J. Microbiological Methods, vol 5, pp. 65–77 (1986).

Jansson et al, "Structural Studies on the Hexose Region of the Core in Lipopolysaccharides from Enterobacteriaceae", J. Biochem, vol. 115, pp. 571–577 (1981).

Kobayashi et al., "Purification and Chemical Properties of Flagellin," *Arch. Biochem. Biophys.*, vol. 84, pp. 342–362 (1959).

Feldmann et al., "The Relationship Between Antigenic Structure and Requirement for Thymus–Derived Cells in the Immune Response," *J. Exp. Med.*, vol. 134, pp. 103–119 (1971).

Hoffman et al., "Immunity to Malaria and Naturally Applied Antibodies to the Circumsporozoite Protein of *Plasmodium Falciparum*", New England Journal of Medicine, vol. 315, No. 10, pp. 601–606 (Sep. 4, 1986).

Schmolka, "A Review of Block Polymer Surfactant," *J. of Amer. Oil. Chem. Soc.*, vol. 54, pp. 110–116.

Wu et al., "New Catalyst Systems of Rare Earth: Acetylscetonate/AlEt$_3$–½H$_2$O for Polymerization of Propylene Oxide," *J. Polym. Sci.: Polym. Chem. Ed.*, vol. 28, pp. 1995–1997 (1990).

López et al., "Polymerization of Some Oxiranes using the Diphenylzinc–Butanone System in Benzene at 60° C.," *Polymer International*, vol. 24, No. 2, pp. 105–112 (1991).

Aida et al., "Synthesis of Propylene Oxide–Ethylene Oxide Block Copolymers with Controlled Molecular Weight, Using Metalloporphyrin as a Catalyst," *Makromol. Chem. Rapid Commun.* I., pp. 677–680 (1980).

Morrison et al., "Adjuvant–free immunological manipulation of livestock," *Res. in Vet. Sci.*, vol. 37, pp. 108–113 (1984).

Hunter et al., "Adjuvant activity of non–ionic block copolymers. IV. Effect of molecular weight and formulation on titre and isotype of antibody," *Vaccine*, vol. 9, pp. 250–256 (1991).

Takayama et al., "Adjuvant activity of non–ionic block copolymers. V. Modulation of antibody isotype by lipopolysaccharides, lipid A and precursors," *Vaccine*, vol. 9, pp. 257–265 (1991).

Zigterman, et al., "Nonionic Block Polymer Surfactants Enhance Immunogenicity of Pneumococcal Hexasaccharide–Protein Vaccines", *Infection and Immunity*, vol. 56, No. 5, pp. 1391–1393 (1988).

Strittmatter et al., "Nontoxic Lipopolysaccharide from *Rhodopseudomonas sphaeroides* ATCC 17023," *J. Bacteriology*, vol. 155, No. 1, pp. 153–158 (1983).

Takayama et al., "Diphosphoryl Lipid A from Rhodopseudomonas sphaeroides ATCC 17023 Blocks Induction of Cachectin in Macrophages by Lipopolysaccharide," *Infection and Immunity*, vol. 57, No. 4, pp. 1336–1338 (1989).

Zigterman et al., "Stimulation of liposome–induced humoral immune responses by non–ionic bloyk polymer surfactants in Xid mice," *J. Immunol.*, vol. 65, pp. 37–42 (1988).

Loppnow et al., "Cytokine Induction by Lipopolysaccharides (LPS) Corresponds to Lethal Toxicity and Is Inhibited by Nontoxic Rhodobacter capsulatus LPS," Infection and Immunity, vol. 58, No. 11, pp. 3743–3750 (1990).Kirkland et al., "Diphosphoryl Lipid A Derived from Lipopolysaccharide (LPS) of *Rhodopseudomonas sphaeroides* Inhibits Activation of 70Z/3 Cells by LPS," Infection and Immunity, vol. 59, No. 1, pp. 131–136 (1991).

Kalish et al., "The Influence of Vaccine Components on the IgG Isotype," Abstracts of the 90th Annual Meeting of the American Society for Microbiology 1990, American Society for Microbiology, Washington, D.C., E–65 (199).

Olin et al., "Thermoplastic Polyurethane Elastomers Made from High Molecular Weight Poly–L™ Polyols," *Polyurethanes World Congress 1991*, pp. 313–318 (Sep. 24–26, 1991).

Reisch et al., "Polyurethane Sealants and Cast Elastomers with Superior Physical Properties," *33rd Annual Polyurethane Technical/Marketing Conference*, pp. 368–374 (Sep. 30–Oct. 3, 1990).

Schuchardt et al., "Preparation of High Molecular Weight Polyols Using Double Metal Cyanide Catalysts," *32nd Annual Polyurethane Technical/Marketing Conference*, pp. 360–364 (Oct. 1–4, 1989).

Allison et al. (1991) Molecular Immunol 28 (3):279–284.

Allison et al. in *Vaccines: New Approaches to Immunological Problems* ed. by R. W. Ellis, Butterworth–Heinemann, 1992 pp. 431–449.

Gupta et al (1993) Vaccine 11(3):293–306.

P. 85 "Earlier Genus May Not Defeat Species" Source?.

Byars et al (1987) Vaccines 5:223–228.

METHODS AND VACCINES COMPRISING SURFACE-ACTIVE COPOLYMERS

A portion of this work was performed under United States Government Support awarded by the National Institute of Health (NIH), Grant Nos. AI-25856 and GM-36954. The United States Government may have certain rights in this invention.

Portions of this work were funded by a grant from the National Institutes of Health, Grant Number AI25856.

CROSS-REFERENCE TO RELATED APPLICATIONS

This application is a continuation of U.S. patent application Ser. No. 08/133,760, filed Oct. 7, 1993, now abandoned which is a continuation of application Ser. No. 07/716,807, filed Jun. 21, 1991, now abandoned which is a continuation-in-part of Ser. No. 07/544,831, filed on Jun. 27, 1990, now abandoned, which is a continuation-in-part of Ser. No. 07/449,086, filed on Dec. 8, 1989, now abandoned, which is a continuation of Ser. No. 07/341,315, filed on Apr. 21, 1989, now abandoned, which is a continuation of U.S. patent application Ser. No. 07/208,335, filed on Jun. 17, 1988, now abandoned, which is a continuation-in-part of U.S. patent application Ser. No. 07/075,187, filed on Jul. 16, 1987, now abandoned, which is a continuation-in-part of U.S. application Ser. No. 06/909,964, filed on Sep. 22, 1986, now abandoned.

TECHNICAL FIELD

The present invention relates to vaccine adjuvants and to improved vaccines that use the adjuvants. The adjuvants can be designed so that the immune response is predominantly antibodies of a desired isotype; e.g., IgG2 or IgG3 isotypes in mice or the corresponding isotypes in man and other animals, thereby improving protection by a vaccine. In addition, the improved vaccine and adjuvant of the present invention provides long lasting protection.

BACKGROUND ART

The term "antigen" is defined as anything that can serve as a target for an immune response. The immune response can be either cellular or humoral. The term "vaccine" is defined herein as a suspension or solution of antigenic moieties, usually consisting of infectious agents, or some part of the infectious agents, that is injected into the body to produce active immunity. The antigenic moiety making up the vaccine can be either a microorganism or a natural product purified from a microorganism, a synthetic product or a genetically engineered protein, peptide, polysaccharide or similar product. The term "cell mediated immunity" is defined as an immune response mediated by cells rather than by antibody. It includes, but is not limited to, delayed type hypersensitivity and cytotoxic T cells. The term "adjuvant" as used herein is any substance whose admixture with an injected immunogen increases or otherwise modifies the immune response. A "hapten" is defined herein as a substance that reacts selectively with appropriate antibodies or T cells but the hapten itself is usually not immunogenic. Most haptens are small molecules or small parts of large molecules, but some macromolecules can also function as haptens. The term "conjugation" is defined herein as the covalent or other form of linking two or more molecules. It can be accomplished either by chemical means or in vivo by biologic means such as genetic engineering. The term "isotype" is a subtype of an antibody. The term "lipopolysaccharide" (LPS) is a amphipathic glycophospholipid obtained from the outer membrane of gram-negative bacteria which has a hydrophobic moiety called lipid A and a sugar moiety (polysaccharide or oligosaccharide). The term "non-toxic LPS" is defined as an LPS with very low toxicity based on one or more measurements of 50% lethal dose in animals ($LD_{50}$), 50% chick embryo lethal dose ($CELD_{50}$), pyrogenicity in rabbit, or dermal Shwartzman reaction. The in vitro measurements of the induction of either/both tissue necrosis factor and IL-1 by macrophage can also be used to determine the toxicity of LPS. The term "detoxified LPS" is defined as being LPS with reduced toxicity due to chemical modification of the structure of Lipid A moiety, i.e., removal of one phosphate group, removal of one to three fatty acyl groups, the introduction of new functional groups (e.g., methyl, acetyl, alcohol and the like), or partial reduction or oxidation.

An effective vaccine must induce an appropriate response to the correct antigen or antigens. There are several distinct types of immune responses which vary in their ability to confer protection against particular diseases. For example, antibodies may confer protection against bacterial infections, but cell mediated immunity is required for eliminating from the body many viral infections and tumors. There are multiple distinct types of antibody and cell-mediated immune responses. Cell-mediated responses are divided into two basic groups: 1) delayed-type hypersensitivity in which T cells act indirectly via macrophages and other cells or cell products, and 2) cytotoxicity in which specialized T-cells specifically and directly attack and kill infected cells.

There are five major classes of antibody: IgM, IgG, IgE, IgA and IgD. These classes have distinct functions in the immune response. IgG, the dominant class in the blood, is subdivided into several different subclasses or isotypes. In mice, these isotypes are IgG1, IgG2a, IgG2b, and IgG3. In humans, the isotypes are IgG1, IgG2, IgG3 and IgG4.[1] Similar isotypes have been defined in most other mammalian species in which they have been investigated. The nomenclature of IgG isotypes is different in different species because the names were coined before the structure or function of the antibody isotypes were understood. Although much still remains to be learned, the IgG isotypes appear to be highly conserved among mammalian species.

[1] Clark, W. R., The Experimental Foundations of Modern Immunology, Chapter 4, "The properties and fine structure of immunoglobulins", pgs. 62–74, John Wiley & Sons The IgG isotypes differ in their ability to confer protection to particular infections. IgG2a and IgG2b in mice activate complement, mediate antibody mediated cell mediated cytotoxicity and other functions. They are particularly effective in conferring protection against many bacterial, viral and parasitic infections. The counterparts in humans appear to be IgG1 and IgG3. In contrast, murine IgG3 is particularly effective in conferring protection against bacteria with polysaccharide coats such as the pneumococcus. The human counterpart seems to be IgG4. Isotypes such as IgG1 in mice do not fix complement, neutralize toxins effectively, but are markedly less effective for many bacterial and viral infections. Because the different IgG isotypes differ markedly in their ability to confer immunity, it is important that vaccines induce the most appropriate isotype for a particular infection. Even though the nomenclature is different, available evidence and modem theory indicate that the properties of immunogens which determine the isotype of antibody produced are similar across mammalian species. In other words, an immunogen which stimulates delayed type hypersensitivity or complement fixing IgG antibody in one species will generally stimulate similar responses in other species.

Biosynthetic and recombinant DNA technology is permitting development of vaccines possessing antigenic epitopes that were previously impossible to produce. Current vaccine candidates include virtually all infectious agents, allergens and even host components such as hormones and molecules involved in autoimmune diseases, cancer and other diseases. The infections agents include, but are not limited to, viruses, bacteria, parasites, rickettsiae and fungi. Hormones are being evaluated as vaccines for diverse purposes such as prevention of pregnancy and treatment of disease. Vaccines for treatment of cancers, such as melanoma, are being evaluated in animals and man. In each case, optimal effect of the vaccine depends upon stimulating the appropriate type, intensity and duration of the immune response.

The work on the parasitic disease malaria is especially important. This disease affects in excess of 200 million people per year worldwide and is the most important disease in the world in terms of morbidity and loss of work. The techniques of genetic engineering have been used to identify, and now to produce in substantial quantities, several peptides and proteins associated with malarial parasites. In particular, a twelve amino acid peptide from the sporozoite stage has been determined to carry an important antigenic site. Antibodies against this particular peptide can kill the parasite immediately after it is injected. Unfortunately, this peptide, by itself, does not produce an adequate immune response. Each species of malaria has a different peptide, but the characteristic structure and repeat units is found in all of them.

In an effort to induce an effective immune response to the sporozoite peptide, the peptide has been conjugated with carriers and administered with adjuvants. To date, however, the adjuvants used with the peptide or peptide conjugates have not produced satisfactory results. Similarly important antigens have been identified on the blood stages of malarial parasites, but available vaccine formulations have been unable to induce protective immunity.

Human immunodeficiency virus (HIV) causes AIDS. Many recombinant and peptide antigens have been prepared from HIV. There is evidence that antibodies against these antigens can neutralize the virus and that the body's immune response is able to prevent or control infections. However, generally effective vaccines to induce protective immune responses against HIV have remained an elusive goal. *Hemophilus influenza* and *Pneumococcal pneumonia* provide further examples. The important antigens of these bacteria are polysaccharides which elicit protective immune responses poorly in infants and elderly persons who are in most danger from these infections. Similar situations exist for numerous other viral, bacterial and parasitic infections in addition to tumors and other diseases which can be modulated by immune responses. Modem science has provided the means to identify and produce antigens from most conditions which are influenced by immune responses. The failure of many new antigens to induce optimal protection has highlighted an increasing need for means to influence the type, intensity, and duration of immune response produced by vaccines.

Thus, interest has arisen in the development of potent, nontoxic adjuvants that will enhance, and perhaps more importantly, modulate the immunogenicity of haptenic epitopes. In addition, adjuvants are-needed for use with conventional vaccines to elicit an earlier, more potent, or more prolonged response of the appropriate type. Such an adjuvant would also be useful in cases where antigen supply is limited or is costly to produce.

The development of adjuvants has, until recently, been empirical. An enormous number of compounds have been found to modulate the immune response. These compounds have been notably diverse in both substance and function, a fact that has complicated attempts to discover the unifying mechanisms of adjuvant action. The elucidation of these mechanisms has lagged behind recent advances in the understanding of the immune system.

This diversity of adjuvants has presented difficulties in their classification. Adjuvants are occasionally grouped according to their origin, be it mineral, bacterial, plant, synthetic, or host product. The first group under this classification are the mineral adjuvants, such as aluminum compounds. The first use of aluminum compounds as adjuvants was described in 1926. Since that time antigens precipitated with aluminum salts or antigens mixed with or adsorbed to performed aluminum compounds have been used extensively to augment immune responses in animals and humans. Aluminum compounds and similar adjuvants appear to work through the following mechanism. The aluminum physically binds to the antigen to form particles. These form a depot of antigen in tissue following injection. Excretion of the antigen is slowed, thus prolonging the time of interaction between the antigen and antigen-presenting cells such as macrophages or follicular-dendritic cells. In addition, immunocompetent cells are attracted to the area of injection and are activated. Aluminum particles have been demonstrated in regional lymph nodes of rabbits seven days following immunization, and it may be that another significant function is to direct antigen to T cell containing areas in the nodes themselves. Adjuvant potency has been shown to correlate with intimation of the draining lymph nodes. While many studies have confirmed that antigens administered with aluminum salts led to increased humoral immunity, cell mediated immunity appears to be only slightly increased, as measured by delayed-type hypersensitivity. Aluminum hydroxide has also been described as activating the complement pathway. This mechanism may play a role in the local inflammatory response as well as immunoglobulin production and B cell memory.

Primarily because of their excellent record of safety, aluminum compounds are presently the only adjuvants used in humans. They are, however, not without problems. Aluminum containing vaccines occasionally cause local reactions. Although allergic manifestations are not usually a clinical problem, aluminum compounds have been also said to attract eosinophils to the area of injection via a T-cell-dependent mechanism, to induce an IgE response if injected after antigen priming, and to elicit a carrier-specific cell population with helper function for IgE response. In addition, aluminum-containing vaccines cannot be lyophilized, thus necessitating refrigerated transport and storage with the resulting risk of contamination.

Finally, and most importantly, aluminum compounds are not always successful in inducing sustained protection from disease. This is due, in part, to their inability to induce the most appropriate isotypes of antibody or the optimal type of cell-mediated immunity. Thus, while aluminum salts have been a sufficient adjuvant for strong immunogens that require only antibody responses to elicit protection, they are not effective when used with weak immunogens like synthetic peptides of malaria or for introducing cell-mediated immune responses or IgG isotype of the type required to fight infections.

Another large group of adjuvants are those of bacterial origin. Adjuvants with bacterial origins have recently been purified and synthesized (e.g. muramyl dipeptides, lipid A)

and host mediators have been cloned (Interleukin 1 and 2), providing chemically characterized products for study. The last decade has brought significant progress in the chemical purification of three adjuvants of active components of bacterial origin: *Bordetella pertussis,* lipopolysaccharide and Freund's Complete Adjuvant (FCA).

*B. pertussis* is of interest due to its ability to modulate cell-mediated immunity through action on T-lymphocyte populations. For lipopolysaccharide and Freund's Complete Adjuvant, adjuvant active moieties have been identified and synthesized which permit study of structure-function relationships.

Lipopolysaccharide and its various derivatives, including lipid A, have been found to be powerful adjuvants in combination with liposomes or other lipid emulsions. It is not yet certain whether derivatives with sufficiently low toxicity for general use in humans can be produced. Freund's Complete Adjuvant is the standard in most experimental studies. However, it produces severe local and systemic inflammatory reactions which may be severe enough to cripple or kill the host. It cannot be used in humans and may be banned for use in animals.

Many other types of materials have been used at various times as adjuvants. They include plant products such as saponin, animal products such as chitin and numerous synthetic chemicals. The source of an adjuvant among these categories has not proved particularly useful in predicting its biological properties.

Adjuvants have also been categorized by their proposed mechanisms of action. This type of classification is necessarily somewhat arbitrary because most adjuvants appear to function by more than one mechanism. Adjuvants may act through antigen localization and delivery, or by direct effects on cells making up the immune system, such as macrophages and lymphocytes. Another mechanism by which adjuvants enhance the immune response is by creation of an antigen depot. This appears to contribute to the adjuvant activity of aluminum compounds, oil emulsions, liposomes, and synthetic polymers. The adjuvant activity of lipopolysaccharides and muramyl dipeptides appears to be mainly mediated through activation of the macrophage, whereas *B. pertussis* affects both macrophages and lymphocytes. Recent and speculative approaches to immunopotentiation, such as the utilization of monokines and lymphokines, and the manipulation of the antigen, carrier, and adjuvant to augment the immune response are currently fashionable.

Small immunogens, such as the synthetic peptide of malaria, can be attached to larger proteins or other carriers to increase the immune response. The relationship between molecular size and complexity of an antigen relative to immunogenicity reflects the availability of antigenic determinants on the molecule. This relationship was first noted by Landsteiner when he demonstrated the need to complex small radicals with larger (carrier) molecules to stimulate an immune response. However, the mechanistic basis for the requirement was to await experiments that demonstrated the carrier effect and the need for a minimum of two antigenic determinants on a molecule to express immunogenicity. These determinants represented the carrier and haptenic determinants that interact with T and B lymphocytes, respectively. However, the influence of the carrier moiety extends beyond simple antigenicity through activation of T cells in T-dependent humoral responses.

The combination of determinants on an antigen molecule can influence the immune response by differential activation of various types of helper and suppressor T cells. A model system demonstrating this effect is the genetically controlled humoral response of responder (C57B1/6) and non-responder (DBA/1) mice to the synthetic terpolymer 1-glutamic acid$^{60}$-L-alanine$^{30}$-L-tyrosine$^{10}$ (GAT). While C57B1/6 mice respond to this polypeptide, DBA/1 mice will respond only if the GAT is coupled to methylated bovine serum albumin (MBSA). However, if the mice are injected with GAT prior to immunization with GAT-MSBA, a detectable antibody response to GAT does not occur. The explanation for these observations is that GAT stimulates helper T cells in the responder mice but preferentially activates suppressor T cells in non-responder mice. This predominance of suppressor cells prevents a response to GAT even when coupled to MBSA. However, if primary immunization is with GAT-MBSA, activation of helper T cells by the carrier moiety provides help that overrides the effect of any suppressor cells activated by GAT.

Determinants associated with a native protein molecule have also been demonstrated to contribute differently to help and suppression. Conjugation of an immunogenic carrier to an antigen can change the isotype of antibodies produced in response to that antigen. Purified polysaccharides from many encapsulated bacteria are thymus-independent antigens due to their polymeric nature with multiple repeating antigenic determinants. While they represent protective antigens of these bacteria, the IgM antibodies produced have limited efficacy in preventing disease. This is largely due to their inability to stimulate immunologic memory or adequate immune responses in very young or old individuals who are at high risk from the infections. Therefore, polysaccharides from *Neisseria meningitidis* and *Haemophilus influenza* type b have been conjugated to proteins, such as tetanus toxoid. These conjugated preparations act as thymus-dependent antigens and induce IgG responses to the polysaccharide moiety as well as immunologic memory. They also induce responses in young or old individuals. Likewise, the thymic-independent polysaccharide carriers have little potential for enhancing the immunogenicity of peptides, such as those involved with malaria which require thymic-dependent IgG immune responses.

Publications by Feldmann and Lee and others state that flagella antigens of Salmonella organisms are typical thymic-independent antigens which stimulate strong IgM antibody responses.[2,3] They stimulate only late maturing B cells which are absent from infants. Such immunogens also tend to induce tolerance in infants and do not induce memory or other aspects of the complex immune responses induced by thymic-dependent antigens in adults. This published data would lead one to believe that they have little potential as adjuvants or carriers for malaria peptides or other small antigens which require thymic-dependent IgG antibody responses.

[2]Feldmann, M., et al., "The Relationship Between Antigenic Structure and the Requirement for Thymus-Derived Cells in the Immune Response", *J. Exp. Med.*, Vol. 134, pgs. 103–119 (1971)

[3]Lee, et al., "Decline and Spontaneous Recovery of the Monoclonal Response to Phosphorylcholine During Repeated Immunization", *J. Immun.*, Vol. 113, pgs. 1644–1646 (1974)

There probably is no precise point of transition that distinguishes a carrier from an adjuvant. The carrier moiety is contributory to a property of antigens that has been termed intrinsic adjuvanticity. The capacity of certain materials to convert a tolerogen to an immunogen has been termed as extrinsic adjuvanticity. Adjuvanticity can be enhanced by increasing the size of the antigen through aggregation of proteins or adsorption to immunogenic or inert carriers. Thus materials, such as aluminum hydroxide, latex particles, bentonite, or liposomes that adsorb antigen and enhance the immune response, are termed adjuvants. However, this observed effect of aggregation of antigen represents only a limited view of adjuvant actions which are now recognized as being extremely complex.

Small peptides and other haptens are incapable of evoking a strong immune response without the use of an adjuvant. Most adjuvants that are currently available are toxic and/or do not evoke an immune response that is effective in protecting the animal or human against infection with the infectious agent. Thus, what is needed is a vaccine which can be administered to an animal or human and will cause the immune system to mount a prolonged and potent immune response of the correct type against an appropriate antigen.

Large hydrophobic nonionic block copolymer surfactants have been shown to be effective immunologic adjuvants which are potentially useful in man.[4,5,6] They appear to act as adhesives which bind protein antigens to the surface of oil drops and/or cells in a way which facilitates antigen presentation. Previous studies have demonstrated that these copolymers can induce high titer, long lasting antibody responses. Interestingly, closely related copolymers have only weak activity, are not adjuvants, or induce inappropriate responses or tolerance. This makes prediction of adjuvant activity complex and imprecise.

[4] Hunter, R. L., et al., "The Adjuvant Activity of Nonionic Block Polymer Surfactants I. The Role of Hydrophile-Lipophile Balance", *J. Immunol.;* Vol. 127, pgs. 1244–1250 (1981)

[5] Hunter, R. L., et al., "The Adjuvant Activity of Nonionic Block Polymer Surfactants II. Antibody Formulation and Inflammation Related to the Structure of Triblock and Octablock Copolymers", *J. Immunol.,* Vol. 133, pgs. 3167–3175 (1984)

[6] Hunter, R. L., et al., "The Adjuvant Activity of Nonionic Block Polymer Surfactants III. Characterization of Selected Biologically Active Surfaces", *Scand. J. Immunol.,* Vol. 23, pgs. 287–300 (1986)

One might predict that adjuvants whose primary activity was cell stimulation or immunomodulation might work well in combination with the adhesive copolymer adjuvants. The combination of copolymer PLURONIC® L121 with a threonyl derivative of MDP has been reported to induce better response, particularly a cell mediated immune response, than L121 by itself.[7]

[7] See U.S. Pat. Nos. 4,606,918 and 4,770,874

Lipopolysaccharides are well-known as B cell mitogens with pronounced effects on macrophages.[8] Its adjuvant activities have been know for many years, but its use has been limited by toxicity and variable efficacy. It has been reported in several articles and reviews that the biological activity of the lipopolysaccharides resides in the lipid A portion of the lipopolysaccharide molecule.[9] Several strategies have been developed for reducing the toxicity of LPS preparations while maintaining their adjuvant activity. They include the removal of a phosphate group from lipid A to produce monophosphoryl lipid A (MPL) or the removal of one or more fatty acid chains from the lipid A moiety. Some types of LPS, particularly that from *Rhodopseudomonas sphaeroides,* have an altered lipid A and are inherently non-toxic.

[8] Louis, J. A., et al., Lipopolysaccharides: From Immunostimulation to Autoimmunity, *Springer Seminars in Immunopathology,* Vol. 2, pgs. 215–229 (1979)

[9] For example, Galanos, C., et al., "Biological Activities and Immunological Properties of Lipid A", *Microbiology,* pgs. 269–276 (1977)

The isotype of antibody is very important in resistance to many infections, but little is known about how to produce a particular isotype response. IgG2a has been associated with being a protective isotype for a variety of pathogens, including *Trypanosoma cruzi,*[10,11] *T. musculi*[12] and *Plasmodium yoelii* (malaria) and the bacterium Brucella. IgE antibodies are particularly toxic for parasites in mice. Many parasites including helminths, schistosomes, and nematode larvae naturally stimulate predominantly IgG1 and IgE antibodies.

The production of IgG1 and IgE appear to be linked. Each isotype has functional advantages which may be appropriate for neutralizing a particular infectious agent. IgG2a binds most avidly to macrophages, which may influence antibody dependent cell mediated cytotoxicity and phagocytosis and can activate complement. The murine IgG3 isotype is particularly effective in protecting against infections with encapsulated bacteria such as *S. pneumoniae.*

[10] Scott, M. T., et al., "Restricted IgG isotype profiles in *T. cruzi* infected mice and Chagas' disease patients", *Clin. Exp. Immunol.,* Vol. 58, pgs. 372–379 (1984)

[11] Takehara, et al., "*Trypanosoma cruzi:* role of different antibody classes in protection against infection in the mouse", *Exp. Parasitology,* Vol. 52, pgs. 137–146 (1981)

[12] Wechsler, et al., "Heat labile IgG2a antibodies affect cure of *Trypanosoma muculi* infection in C57BL/6 mice", *J. Immunol.* Vol. 137, pgs. 2968–2972 (1986)

Finally, diseases caused by *Streptococcus pneumoniae* are among the most important bacterial infections of infancy and childhood. A multivalent vaccine containing capsular polysaccharides from 23 types of pneumococci is widely used today. Several studies show that the efficacy of the vaccine in preventing bacteremic illness was 0% in children 2–10 years of age and 49% in persons older than 10 years. There is no convincing evidence that the vaccine is effective for the chronically ill and studies have shown that there is no benefit for the elderly and the institutionalized patients.

By themselves, capsular polysaccharides are thymus independent type 2 (TI-2) antigens which are poorly immunogenic in the very young or very old. TI-2 antigens induce only a restricted number of isotypes, mainly IgM. They induce only a weak memory response, or no memory response, and tolerance is easily induced.

Thus, what is needed in the vaccine art is a composition and method of administering vaccines so that the most efficacious and protective antibody isotype is induced. The vaccine should also be capable of inducing a long-lasting high titer of antibodies.

SUMMARY OF THE INVENTION

The present invention comprises a vaccine adjuvant which, when admixed with an antigen and administered into a human or animal, will induce a more intense immune response to the antigen than when the antigen is administered alone. In many cases, the adjuvant that is described as the present invention will increase overall titer of antibodies specific for the vaccine antigen. For example, when the present invention is practiced with a conventional antigen, the isotype that is induced is changed from a predominantly IgG1 isotype to the more protective IgG2 isotype and, in some cases, IgG3 isotype or the corresponding isotype in other species. Thus, by practicing the present invention, one can improve the overall protective effect of conventional vaccines.

In addition, the present invention is particularly effective in inducing protective antibodies against peptide antigens including, but not limited to, (asparagine-alanine-glycine-glycine) 5-tyrosine [(NAGG)$_5$] malaria antigen. It is effective for a wide range of antigens and types of antigens. This includes polysaccharides, such as pneumococcal polysaccharide, oligosaccharides, proteins, peptides, and natural or synthetic haptens or combinations of these materials.

The present invention comprises an adjuvant and a vaccine which is comprised of an antigen and an improved adjuvant. In one embodiment of the present invention, the antigen is admixed with an effective amount of a surface-active copolymer having the following general formula:

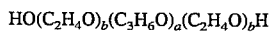

wherein the molecular weight of the hydrophobe ($C_3H_6O$) is between approximately 4500 to 9000 and the percentage of hydrophile ($C_2H_4O$) is between approximately 3% and 15% by weight.

The improved vaccine of the present invention also comprises an antigen and an adjuvant wherein the adjuvant comprises a surface-active copolymer with the following general formula:

wherein the molecular weight of the hydrophobe ($C_3H_6O$) is between approximately 3000 to 9000 and the percentage of hydrophile ($C_2H_4O$) is between approximately 3% and 15% by weight which is formulated as a water-in-oil emulsion. The copolymers destabilize commonly used water-in-oil vaccine emulsions, but surprisingly increase their efficacy and increase stability if the usual emulsifying agents are omitted.

It is also contemplated as part of the present invention an adjuvant comprising a non-toxic lipopolysaccharide. The non-toxic lipopolysaccharide can be a naturally occurring lipopolysaccharide, such as the lipopolysaccharide derived from *Rhodopseudomonas sphaeroides*, or a detoxified lipopolysaccharide. It is contemplated that the adjuvant is prepared from a toxic lipopolysaccharide wherein the sugar portion of the molecule is intact and the lipid A portion of the molecule has been modified thereby rendering the lipopolysaccharide much less toxic.

The improved vaccine of the present invention also comprises an antigen and an adjuvant wherein the adjuvant comprises a surface-active copolymer with the following general formula:

wherein the molecular weight of the hydrophobe ($C_3H_6O$) is between approximately 3000 to 9000 and the percentage of hydrophile ($C_2H_4O$) is between approximately 3% and 15% by weight and a lipopolysaccharide (LPS) derivative. The adjuvant comprising a combination of LPS and surface-active copolymer produces a synergy of effects in terms of peak titer, time to reach peak titer and length of time of response. In addition, the combination tends to increase the protective IgG2 isotypes.

The combination of lipid conjugated polysaccharide with copolymer and an immunomodulating agent such as monophosphoryl lipid A, induces the production of a strong IgG response in which all of the subclasses of IgG are present. In particular, the IgG2 and IgG3 subclasses which are protective against pneumococcal infections are predominant. This is an unexpected finding because there is no protein or peptide in the immunogen preparation. It is believed that peptide moieties are essential for stimulating T cells which are required for production of these isotypes. Others have reported that polysaccharides are incapable of stimulating T cells. Nevertheless, the combination of copolymer, lipid conjugated polysaccharide and immunomodulating agent is able to produce such a response.

The present invention also comprises a vaccine that is especially useful for immunizing an animal or human against a protein, small peptide, polysaccharide, or hapten. According to the present invention, the protein, small peptide, polysaccharide or hapten is conjugated to the flagella that is derived from a microorganism. The flagella may be derived from any flagellated microorganism; however, those from *Salmonella species* are preferred.

In addition, the flagella may be genetically engineered. Accordingly, it is an object of the present invention to provide a vaccine that is particularly effective in providing a prolonged and potent immune response to small immunogenic determinants. The conjugated flagella plus antigen is even more effective when admixed with a copolymer with the following general formula:

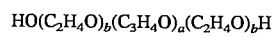

wherein the molecular weight of the hydrophobe ($C_3H_6O$) is between approximately 3000 to 9000 and the percentage of hydrophile ($C_2H_4O$) is between approximately 3% and 15% by weight and a lipopolysaccharide (LPS) derivative. The adjuvant comprising a combination of LPS and surface-active copolymer produces a synergy of effects both in terms of peak titer and time to reach peak titer. In addition, the combination tends to increase the protective IgG2 isotypes.

Accordingly, it is an object of the present invention to provide an improved adjuvant for administering with antigens comprising an adjuvant capable of inducing more intense immune responses to the antigens.

Another object of the present invention is to provide a vaccine which induces stronger antibody responses to antigens in infants and young children and in aged people who respond poorly to conventional vaccines.

Another object of the present invention is to provide an adjuvant that will induce desired isotypes of antibodies.

Another object of the present invention is to provide an adjuvant and vaccine which will induce protective immune responses in very young and aged individuals who respond poorly to conventional vaccines.

Another object of the present invention is to provide an adjuvant and vaccine which will induce an appropriate balance of antibody and cell mediated immunity thereby providing the maximum protection against a particular disease.

Another object of the present invention is to provide an adjuvant that will induce longer lasting antibody populations.

Another object of the present invention is to provide a effective vaccine that can utilize a recombinant protein or a synthetic peptide to produce a sustained immune response capable of protecting an individual from infection by the malaria parasite.

Another object of the present invention is to provide an effective vaccine that can utilize a synthetic peptide of the AIDS virus to produce an immune response that is effective in preventing the disease.

Yet another object of the present invention is to provide a vaccine that is capable of stimulating the immune system of an animal or human to produce a potent and prolonged IgG response to a small immunogenic determinant, such as a peptide, hapten or polysaccharide or a large molecule such as a protein or polysaccharide.

Another object of the present invention is to provide a vaccine which has very low toxicity for humans or animals.

Yet another object of the present invention is to provide a vaccine which causes little or no local allergic reaction.

A further object of the present invention is to provide a vaccine which can be lyophilized.

Another object of the present invention is to provide a replacement for Freund's Complete Adjuvant for the production of antibodies in animals.

It is yet another object of the present invention to provide an adjuvant that will induce desired antibody isotypes.

Another object of the present invention is to provide an adjuvant that can be used with a conventional vaccine preparation.

These and other objects, features and advantages of the present invention will become apparent after a review of the following detailed description of the disclosed embodiment and the appended claims.

DETAILED DESCRIPTION

Figure 1:
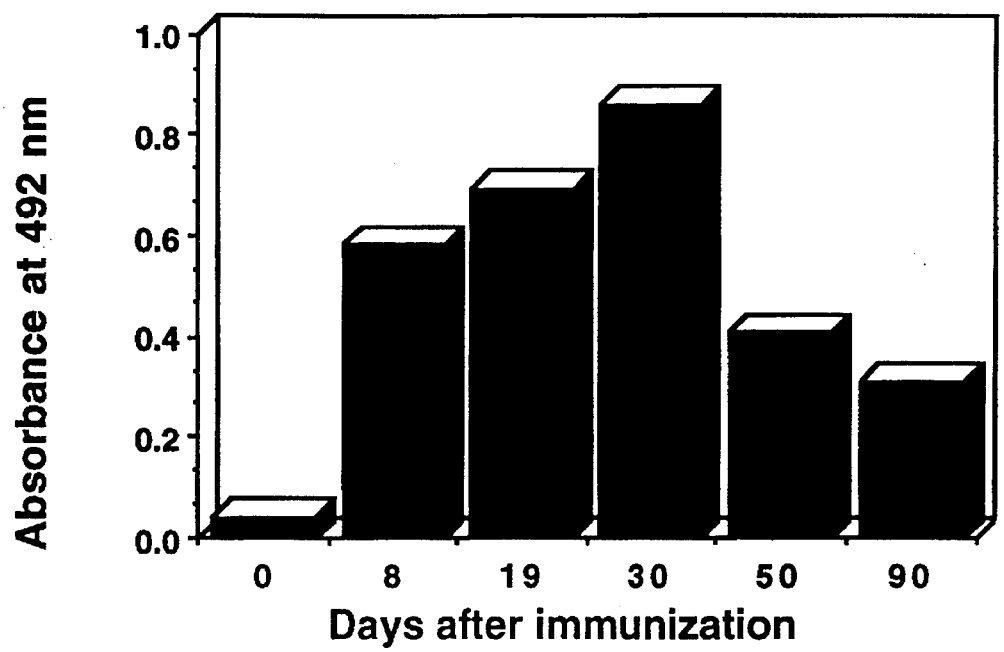
FIG. 1 is a graph illustrating the antibody titer in a mouse immunized with trinitrophenol (TNP) conjugated to flagella protein from Salmonella.

The present invention comprises an improved adjuvant. In one embodiment of the present invention, an antigen is admixed with an effective amount of an adjuvant, the adjuvant comprises a surface-active copolymer having the following general formula:

$$HO(C_2H_4O)_b(C_3H_6O)_a(C_2H_4O)_bH$$

wherein the molecular weight of the hydrophobe $(C_3H_6O)$ is between approximately 4500 to 9000 and the percentage of hydrophile $(C_2H_4O)$ is between approximately 3% and 15% by weight. The copolymers may be obtained from BASF Corporation, Parsippany, N.J. or from CytRx Corporation, Atlanta, Ga.

A preferred surface-active copolymer is a copolymer designated PLURONIC® L141 with the following formula:

$$HO(C_2H_4O)_b(C_3H_6O)_a(C_2H_4O)_bH$$

wherein the molecular weight of the hydrophobe $(C_3H_6O)$ is approximately 4600 and the percentage of hydrophile $(C_2H_4O)$ is approximately 10% by weight.

Another preferred surface-active copolymer is a copolymer designated PLURONIC®L180.5 with the following formula:

$$HO(C_2H_4)_b(C_3H_6)_aC_2H_4O)_bH$$

wherein the molecular weight of the hydrophobe $(C_3H_6O)$ is approximately 5200 and the percentage of hydrophile $(C_2H_4O)$ is approximately 5% by weight.

Another preferred surface-active copolymer is a copolymer designated PLURONIC® L181.5 with the following formula:

$$HO(C_2H_4O)_b(C_3H_6O)_a(C_2H_4O)_bH$$

wherein the molecular weight of the hydrophobe $(C_3H_6O)$ is approximately 5200 and the percentage of hydrophile $(C_2H_4O)$ is approximately 15% by weight.

Another preferred surface-active copolymer is a copolymer designated PLURONIC® L190.5 with the following formula:

wherein the molecular weight of the hydrophobe ($C_3H_6O$) is approximately 8600 and the percentage of hydrophile ($C_2H_4O$) is approximately 5% by weight.

An adjuvant formulation which is contemplated as part of the present invention is comprised of oil such as animal oil, such as squalane or squalene, vegetable oil or mineral oil, a non-ionic surface active agent suitable for forming water-in-oil emulsions such as Span 80 (sorbitan monooleate), silica and a surface active copolymer with the following general formula:

wherein the molecular weight of the hydrophobe ($C_3H_6O$) is between approximately 3000 to 9000 and the percentage of hydrophile ($C_2H_4O$) is between approximately 3% and 15% by weight. In addition, the surface active copolymer can be an octablock copolymer with the following general formula:

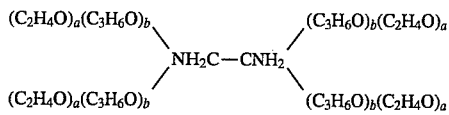

wherein:

the molecular weight of the hydrophobe portion of the octablock copolymer consisting of ($C_3H_6O$) is between approximately 5000 and 7000 daltons;

a is a number such that the hydrophile portion represented by ($C_2H_4O$) constitutes between approximately 10% and 40% of the total molecular weight of the compound;

b is a number such that the ($C_3H_6O$) portion of the octablock copolymer constitute between approximately 60% and 95% of the compound and a lipopolysaccharide derivative.

The preferred amounts of the components are approximately 40% to 90% by weight of squalene, 2% to 50% by weight sorbitan monooleate, approximately 0.5 to 10% by weight of silica and approximately 2% to 10% by weight of the surface active copolymer. A preferred surface-active copolymer is PLURONIC® L141. The silica particles are preferably approximately 0.5 to 20μ in diameter.

Another adjuvant which is contemplated as part of the present invention are non-toxic lipopolysaccharides and detoxified toxic lipopolysaccharides. These are lipopolysaccharides which either are inherently non-toxic or are toxic lipopolysaccharides which have been chemically modified to reduce the toxicity. This includes mild alkaline hydrolysis of fatty acids.

Naturally occurring non-toxic lipopolysaccharides include, but are not limited to, those lipopolysaccharides that are associated with the *Rhodopseudomonas species*, including *R. sphaeroides, R. acidophilia, R. blastica, R. gelatinosa, R. capsulata, R. palustris* and *R. viridis*. There are several methodologies for detoxifying toxic lipopolysaccharides available. Some of these methods are referred to in the Examples. These methodologies generally include chemical modification of the lipid A part of the molecule. It is important to note that the detoxified lipopolysaccharide is a toxic lipopolysaccharide wherein the polysaccharide portion of the molecule is intact and the lipid A portion of the molecule has been modified by removal of fatty acids, thereby rendering the lipopolysaccharide much less toxic.

The improved adjuvant of the present invention also comprises a lipopolysaccharide derivative combined with a surface-active copolymer with the following general formula:

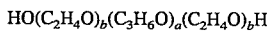

wherein the molecular weight of the hydrophobe ($C_3H_6O$) is between approximately 3000 to 9000 and the percentage of hydrophile ($C_2H_4O$) is between approximately 3% and 15% by weight. The present invention also comprises a lipopolysaccharide derivative combined with an octablock copolymer with the following general formula:

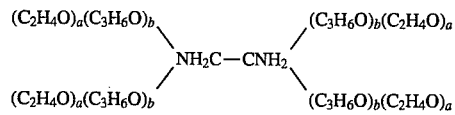

wherein:

the molecular weight of the hydrophobe portion of the octablock copolymer consisting of ($C_3H_6O$) is between approximately 4000 and 9000 daltons, preferably 5000 to 7000 daltons;

a is a number such that the hydrophile portion represented by ($C_2H_4O$) constitutes between approximately 5% and 40% of the total molecular weight of the compound;

b is a number such that the ($C_3H_6O$) portion of the octablock copolymer constitute between approximately 60% and 95% of the compound.

The ($C_3H_6O$) portion of the copolymer can constitute up to 95% of the compound. The ($C_2H_4O$) portion of the copolymer can constitute as low as 5% of the compound.

The adjuvant comprising a combination of LPS and surface-active copolymer produces a synergy of effects both in terms of peak titer and time to reach peak titer. In some cases, especially with the lower molecular weight lipopolysaccharides, the initial liter is higher and then is slightly depressed with time. With the higher molecular weight lipopolysaccharides, the initial liter is higher and the response remains high over time. With all of the lipopolysaccharides, the combination tends to increase the protective IgG2a and IgG2b isotypes. This is unexpected because the LPS, by itself, has been reported to act as an adjuvant to induce a predominantly IgG1 immune response.

The improved adjuvant also comprises a surface-active copolymer with the following general formula:

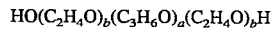

wherein the molecular weight of the hydrophobe ($C_3H_6O$) is between approximately 3000 to 9000 and the percentage of hydrophile ($C_2H_4O$) is between approximately 3% and 15% by weight and a reverse octablock copolymer with the following general formula:

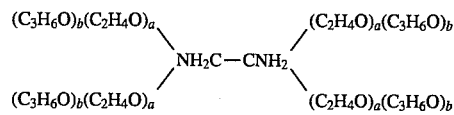

wherein:

the molecular weight of the hydrophobe portion of the octablock copolymer consisting of ($C_3H_6O$) is between approximately 5000 and 7000 daltons;

a is a number such that the hydrophile portion represented by ($C_2H_4O$) constitutes between approximately 10% and 40% of the total molecular weight of the compound;

b is a number such that the ($C_3H_6O$) portion of the octablock copolymer constitutes between approximately 60% and of the compound.

The ($C_3H_6O$) portion of the copolymer can constitute up to 95% of the compound. The ($C_2H_4O$) portion of the copolymer can constitute as low as 5% of the compound.

a is a number such that the hydrophile portion represented by polyoxyethylene ($C_2H_4O$) constitutes between approximately 5% to 40% of the total molecular weight of the compound;

the mean aggregate molecular weight of the hydrophobe portion of the octablock copolymer consisting of polyoxypropylene ($C_3H_6O$) is between approximately 4000 and 8000 daltons; and b is a number such that the polyoxypropylene ($C_3H_6O$) portion of the total molecular weight of the octablock copolymer constitutes between approximately 60% and 90%.

The ($C_3H_6O$) portion of the copolymer can constitute up to 95% of the compound. The ($C_2H_4O$) portion of the copolymer can constitute as low as 5% of the compound.

The improved adjuvant also comprises a surface-active copolymer with the following general formula:

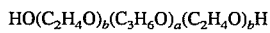

$$HO(C_2H_4O)_b(C_3H_6O)_a(C_2H_4O)_bH$$

wherein the molecular weight of the hydrophobe ($C_3H_6O$) is between approximately 3000 to 9000 and the percentage of hydrophile ($C_2H_4O$) is between approximately 3% and 15% by weight and an octablock copolymer with the following general formula:

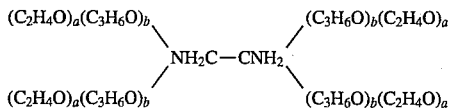

wherein:
the molecular weight of the hydrophobe portion of the octablock copolymer consisting of ($C_3H_6O$) is between approximately 5000 and 7000 daltons;

a is a number such that the hydrophile portion represented by ($C_2H_4O$) constitutes between approximately 10% and 40% of the total molecular weight of the compound;

b is a number such that the ($C_3H_6O$) portion of the octablock copolymer constitutes between approximately 60% and 90% of the compound.

The ($C_3H_6O$) portion of the copolymer can constitute up to 95% of the compound. The ($C_2H_4O$) portion of the copolymer can constitute as low as 3% of the compound.

The present invention also includes vaccines which comprise antigens and the aforementioned adjuvants.

The present invention also comprises a vaccine that is especially useful for immunizing an animal or human against a polysaccharide, protein, small peptide or other hapten. According to the present invention, the small peptide or hapten is conjugated to flagella that is derived from a microorganism. The flagella may be derived from any flagellated microorganism; however, those from *Salmonella species* are preferred. It is to be understood that the preferred bacterial species from which the flagella are derived for any particular application is dependent upon the particular antigen requirements of the application and is not critical for this invention.

Some bacteria possess a single flagellum while others have a tuft of flagella and still others have flagella distributed over the entire cell surface. Bacterial flagella are between 10 and 35 nm in diameter and may sometimes exceed 10 to 15 μm in length, or many times the diameter of the cell. Most bacterial flagella show a regular and uniform curl with a wavelength of about 2.5 μm.

When bacterial flagella, which are protein in nature, are acidified to pH=3, they dissociate into identical monomeric subunits called flagellin, which has a molecular weight of approximately 40,000 in most species. Under appropriate conditions of pH and salt concentration, flagellin monomers will spontaneously reaggregate to form structures that appear to be identical with intact flagella possessing periodic curls of the same wavelength as the native flagella.

Intact bacterial flagella in the native form or fixed with a number of fixative agents can be used in practicing the present invention. Additionally, repolymerized flagellin is satisfactory in practicing the present invention. It is believed that an essential component of the present invention is that the preparation consists of a polymer composed of flagellin molecules regularly spaced in a geometric pattern to produce the elongated flagellar structure typical of the particular microorganism.

A number of procedures for preparing flagella from bacterial cultures have been developed and are well-known to those of ordinary skill in the art. The preferred procedure is a modification of the procedure of Kobayashi, et al., as described herein[13].

[13] Kobayashi, et al., *Arch. Biochem. Biophys.* 84, pgs. 342–362 (1959)

*Salmonella typhi* organisms of strain TY2 are grown in motility agar. The highly motile organisms should be selected because they produced the most flagella. Organisms are then inoculated in 20 liters of trypticase soy broth and incubated at 37° C. for approximately 30 hours until the end of the log phase of growth. The organisms may be killed at this time by the addition of formaldehyde to produce a 0.3% suspension. The organisms are preferably collected by centrifugation; however, care should be taken to avoid production of excessive shear force. The flagella are then removed from the organisms by shaking vigorously for 20 minutes in a shaker. Other mixes and devices which produce a shear force to break off the flagella without disrupting the organism are equally satisfactory.

The flagella are then separated from the cell bodies by differential centrifugation. The cell bodies are removed by centrifuging at approximately 2000 rpm in a standard laboratory centrifuge. The flagella are then collected by ultracentrifugation at 30,000 rpm. The flagella are then resuspended and recentrifuged in an ultracentrifuge, and soluble contaminating materials are poured off. Large contaminating materials will form a black spot at the bottom of the transparent flagella pellet. This material is physically removed and discarded. The end product derived from 20 liters of bacterial culture will be approximately 100 mg of purified flagella.

Flagellin may be produced by acidifying unfixed flagella at a pH of approximately 2 overnight. This treatment dissociates the flagellar proteins to produce the monomers of flagellin which have a molecular weight of approximately 30,000. The monomers reassemble into the polymerized flagella when allowed to stand at neutral pH for a period of at least 24 hours. The repolymerized flagellin is nearly as effective as the native flagella as an adjuvant and carrier for small antigen moieties. The monomeric flagellin or proteolytic cleavage fragments of flagellin protein are very much less effective.

The antigen, i.e., protein, polysaccharide, hapten or peptide moieties, can be chemically conjugated to the flagella by any one of the standard means well known to those of ordinary skill in the art. One of the simplest and most effective means is by using gluteraldehyde. Gluteraldehyde is a divalent cross-linking compound which covalently attaches the peptide to the flagella and further fixes the flagella preparation. Other chemical cross-linking reagents or chemical antigen derivatives, such as dinitrofluorobenzene, are effective. The methods of conjugating an antigen, hapten or peptide moieties are well known to those of ordinary skill in the art.

The amounts of antigen attached to the flagella varies with the particular application and is not a critical component of this invention. Preferably, between 2 and 10 peptide or hapten units per flagellin monomer in the flagella preparation is sufficient. Smaller multiples are needed for larger protein or polysaccharide antigens.

The conjugated flagella preparation is purified by dialysis, centrifugation, or any other standard method. The material is then resuspended in saline at a concentration approximating 100 μg/ml.

This preparation is effective in low doses between 1 and 100 μg per injection. A dose of 10 μg produces a satisfactory response in many situations. The material can be injected by any convenient route, intravenous, subcutaneous, intramuscular, or intraperitoneal. The subcutaneous or intramuscular route is usually the most convenient for many vaccine purposes.

As an example, injections of 20 μg of *Salmonella typhi* flagella conjugated with dinitrophenol resulted in IgG antibody titers specific for the hapten DNP which rose at the end of the first week after injection and persisted for over one year.

Persistence of the immune response to flagella and to antigenic moieties conjugated to flagella is unusual and unexpected. The material does not form a local depot of antigen at the site of injection. Approximately 90 to 95% of the injected dose of flagella is broken down and excreted within 24 hours. A portion of the material is retained for a prolonged time in germinal centers within local lymph nodes. It is believed that the presence of this antigen in germinal centers is responsible for the prolonged antibody production.

This invention has numerous advantages over other available adjuvant preparations. It produces very little inflammation at the site of injection and is entirely biodegradable. This contrasts sharply with oil emulsions or mineral salts, such as aluminum. Very small doses of antigen are required to produce prolonged immune responses. A significant portion of the antibody is complement-fixing IgG which is the type required for protection against malaria, sporozoites, and other important infections. The product is stable especially when prepared with fixatives, such as gluteraldehyde. It can be lyophilized and stored at room temperature indefinitely. When reconstituted with saline, it is stable for several weeks with refrigeration and several days at room temperature.

Unlike live attenuated vaccines which may produce infections in susceptible hosts, this vaccine preparation consists only of polymerized protein with traces of polysaccharide.

The preferred dose of a vaccine prepared according to the present invention is between 5 μg and 500 μg. The optimal dose for any vaccine will depend upon the antigen that is conjugated with the flagella protein and the immunological condition of the animal or human that is being vaccinated.

The vaccine of the present invention also includes the administration of the vaccine with an adjuvant to further enhance the immune response. The preferred adjuvant that can be used with the vaccine of the present invention is a block copolymer that comprises a polymer of hydrophilic polyoxyethylene built on an ethylene diamine initiator. Polymers of hydrophobic polyoxypropylene are then added to a block of hydrophilic polyoxyethylene. This results in an octablock copolymer with the following general formula:

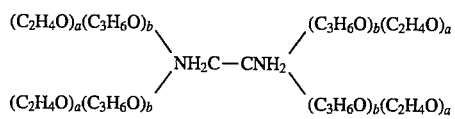

wherein:

the molecular weight of the hydrophobe portion of the octablock copolymer consisting of $(C_3H_6O)$ is between approximately 5000 and 7000 daltons;

a is a number such that the hydrophile portion represented by $(C_2H_4O)$ constitutes between approximately 10% and 40% of the total molecular weight of the compound;

b is a number such that the $(C_3H_6O)$ portion of the octablock copolymer constitutes between approximately 60% and 90% of the compound.

The $(C_3H_6O)$ portion of the copolymer can constitute up to 95% of the compound. The $(C_2H_4O)$ portion of the copolymer can constitute as low as 5% of the compound.

The preferred adjuvant has the following formula:

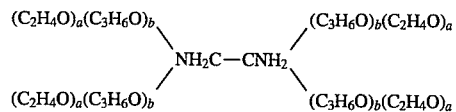

wherein a is equal to approximately 5 and b is equal to approximately 32.

Another copolymer that can be used with the vaccine comprising the present invention has the following formula:

$$HO(C_2H_4O)_b(C_3H_6O)_a(C_2H_4O)_bH$$

wherein the molecular weight of the hydrophobe $(C_3H_6O)$ is between approximately 2000 to 5500 and the total molecular weight of the compound is between approximately 2300 and 5500.

The preferred adjuvant has the following formula:

$$HO(C_2H_4)_b(C_3H_6O)_a(C_2H_4O)_bH$$

wherein the molecular weight of the hydrophobe $(C_3H_6O)$ is approximately 4600 and the percentage of hydrophile $(C_2H_4O)$ is approximately 10% by weight.

Another preferred adjuvant has the following formula:

$$HO(C_2H_4O)_b(C_3H_6O)_aC_2H_4O)_bH$$

wherein the molecular weight of the hydrophobe $(C_3H_6O)$ is approximately 5200 and the percentage of hydrophile $(C_2H_4O)$ is approximately 10% by weight.

The polymer blocks are formed by condensation of ethylene oxide and propylene oxide onto a tetrafunctional ethylene diamine initiator at elevated temperature and pressure in the presence of a basic catalyst. There is some statistical variation in the number of monomer units which combine to form a polymer chain in each copolymer. The molecular weights given are approximations of the average weight of copolymer molecule in each preparation. A further description of the preparation of these block copolymers is found in U.S. Pat. No. 2,674,619 and U.S. Pat. No. 2,979,528 which are incorporated herein by reference.[14]

[14] Also see Schmolka, I. R., "A Review of Block Polymer Surfactants", *J. Am. Oil Chemists' Soc.*, 54:110–116 (1977) and Block and Graft Copolymerization, Vol. 2, edited by R. J. Ceresa, John Wiley & Sons, New York (1976)

The published molecular weight for poloxamers and poloxamines is commonly determined by the hydroxyl method. The end groups of polyether chains are hydroxyl groups. The number averaged molecular weight can be calculated from the analytically determined "OH Number" expressed in mg KOH/g sample. It should be understood that the absolute value of the molecular weight of a polydisperse compound can be different depending upon the methodology used to determine the molecular weight. Thus, it is important to know by what method the molecular weight of the copolymer has been determined. As used herein, the molecular weights of all of the copolymers was determined by the hydroxyl method. A slightly different number is obtained when the molecular weight is determined by another method such as high performance liquid chromatography.

The vaccine which comprises the present invention is mixed with the octablock copolymer and administered to the human or animal. The preferred amount of adjuvant administered with the vaccine of the present invention is between approximately 0.1 mg and 5.0 mg with the most preferred amount between approximately 0.5 mg and 2 mg.

Another embodiment of the adjuvants of the present invention are various derivatives of lipid A. The structures of the various species of lipid A are described in articles by Takayama, K., et al. and Raetz, C. R. H., both of which are incorporated herein by reference.[15,16] Monophosphoryl lipid A has lower toxicity than the complete lipid A molecule but has a lower toxicity to animals than does the complete lipid A. Lipid IVA and lipid X are precursors in the biosynthesis of lipid A. The structures of some of the lipid A derivatives that are contemplated as part of the present invention are shown in FIGS. 10 through 13.

[15]Takayama, K., et al., "Fatty Acyl Derivatives of Glucosamine 1 Phosphate in *Escherichia coli* and Their Relation to Lipid A", *J. Biol. Chem.*, Vol. 256, pgs. 7379–7385 (1983)

[16]Raetz, C. R. H., "Structure and Biosynthesis of Lipid A in *Escherichia coli*, in *Escherichia Coli* and *Salmonella Typhimurium*", *Cellular and Molecular Biology*, Vol. 1, Neidhardt, F. C. Editor, American Society for Microbiology Several recent reports have implicated IgG2a antibodies as conferring protection against several viral and bacterial infections. IgG2b antibody has been less well studied but has also been reported to be protective. Antibody of the IgG1 subclass does not fix complement and is thought to be of considerably less protective efficacy in many situations. Consequently, the ability of LPS derivatives to shift the antibody response toward the IgG2 isotypes, especially when admixed with copolymers, can be expected to increase the efficacy of vaccines.

Antigens that can be used in the present invention are compounds which, when introduced into a mammal, will result in the formation of antibodies. Representative of the antigens that can be used according to the present invention include, but are not limited to, natural, recombinant or synthetic products derived from viruses, bacteria, fungi, parasites and other infectious agents in addition to autoimmune diseases, hormones or tumor antigens which might be used in prophylactic or therapeutic vaccines. The viral or bacterial products can be components which the organism produced by enzymatic cleavage or can be components of the organism that were produced by recombinant DNA techniques that are well-known to those of ordinary skill in the art. The following is a partial list of representative antigens:

VIRUSES

HIV
Rotavirus
Foot and mouth disease
Influenza
Parainfluenza
Herpes species, Herpes simplex, Epstein Barr virus Chicken pox, pseudorabies
Rabies
Polio
Hepatitis A
Hepatitis B
Hepatitis C
Measles
Distemper
Venezuelan equine encephalomyelitis
Rota virus
Feline leukemia virus
Reovirus
Respiratory sycytial virus
Lassa fever virus
Polyoma tumor virus
Canine parvovirus
Bovine papilloma virus
Tick borne encephalitis
Rinderpest
Human rhinovirus species
Enterovirus species, Mengo virus
Paramyxovirus
Avian infectious bronchitis virus

BACTERIA

*Borderella pertussis*
*Brucella abortis*
*Escherichia coli*
*Salmonella species, Salmonella typhi*
Streptococci
Cholera
Shigella
Pseudomonas
Tuberculosis
Leprosy

RICKETSIAL INFECTIONS

Rocky mountain spotted fever
Thyphus

PARASITES

Malaria (*Plasmodium. falciparum, P. vivax, P. malariae*)
Schistosomes
Trypanosomes

FUNGUS

*Cryptococcus neoformans*

SUBUNIT RECOMBINANT PROTEINS

Herpes simplex
Epstein Barr virus
Hepatitis B
Pseudorabies
Flavivirus, Denge, Yellow fever
*Neisseria gonorrhoeae*
Malaria: circumsporozoite protein, merozoite protein
Trypanosome surface antigen protein
Pertussis
Alphaviruses
Adenovirus

PROTEINS

Diphtheria toxoid
Tetanus toxoid
Meningococcal outer membrane protein (OMP)
Streptococcal M protein
Hepatitis B
Influenza hemagglutinin

SYNTHETIC PEPTIDE

Malaria
Influenza
Foot and mouth disease virus
Hepatitis B, Hepatitis C

POLYSACCHARIDE

Pneumococcal polysaccharide
*Haemophilis influenza* polyribosyl-ribitolphosphate (PRP)
*Neisseria meningitides*
*Pseudomonas aeruginosa*
*Klebsiella pneumoniae*

OLIGOSACCHARIDE

Pneumococcal

Haptens are compounds which, when bound to an immunogenic carrier and introduced into a chordate, will elicit formation of antibodies specific for the hapten. Representative of the haptens are steroids such as estrogens and cortisones, low molecular weight peptides, other low molecular weight biological compounds, drugs such as antibiotics and chemotherapeutic compounds, industrial pollutants, flavoring agents, food additives, and food contaminants, and/or their metabolites or derivatives.

In addition to the foregoing embodiments of the present invention, addition of certain of the copolymers to silica suspensions has provided an unexpected increase in the adjuvant activity of the composition.

Silica is a known adjuvant, but its use has been limited by toxicity, especially fibrosis. This toxicity is reduced and the effectiveness increased by incorporation of the silica into an oily vehicle with or without other adjuvant moieties such as surface-active copolymers or LPS. The dose and toxicity of silica are reduced, while the effectiveness is increased by the present invention. Preferably, the oil emulsion comprises an oil and silica particles with the emulsion comprising between 40% and 99% oil. A preferred oil is squalane (Sigma Chemical Company, St. Louis, Mo.). In addition to the oil, one can optionally add a detergent or mixture of detergents to the oil. Examples of detergents that can be used in the present invention are polyoxyethylenesorbitan (Tween) and sorbitan (Span) (Sigma Chemical Company, St. Louis, Mo.). However, copolymers such as PLURONIC® L121 are frequently preferable.

Since, certain components of vaccine adjuvants are liable to oxidation, antioxidants have been included as preservatives. The oil vehicle squalene is particularly susceptible to oxidation. The block copolymers may also be affected. Many antioxidants are available which are potentially acceptable to prevent oxidative degradation of vaccine components. Examples of these, tocopherol (vitamin E) or tocopherol derivatives, were found to have the ability to enhance adjuvant activity in addition to preventing oxidation. It has been found that the antioxidants are particularly effective in increasing immune responses and reducing local inflammation in addition to serving as an antioxidant when used in combination with the block copolymer or silica emulsions. Thus, it is contemplated as part of the present invention the admixture of antioxidants, such as tocopherol or tocopherol derivatives, with the adjuvants and vaccines described herein.

The following specific examples will illustrate the invention as it applies to enhancing the immune response of an organism to small haptens. It will be appreciated that other examples will be apparent to those of ordinary skill in the art and that the invention is not limited to these specific illustrative examples.

EXAMPLE 1

*Salmonella typhi* organisms of strain TY2 are grown in motility agar. Organisms are then inoculated in 20 liters of trypticase soy broth and incubated at 37° for 30 hours until the end of the log phase of growth. The organisms are killed at this time by the addition of formaldehyde to produce a 0.3% suspension. The organisms are collected by centrifugation. Care should be taken to avoid production of excessive shear force. The flagella are then removed from the organisms by shaking vigorously for 20 minutes in a shaker. Other mixes and devices which produce a shear force to break off the flagella without disrupting the organism are equally satisfactory.

The flagella are then separated from the cell bodies by differential centrifugation. The cell bodies are removed by centrifuging at 2000 rpm in a standard laboratory centrifuge. The flagella are then collected by ultracentrifugation at 30,000 rpm. After the ultracentrifugation, the flagella are resuspended and recentrifuged in an ultracentrifuge, and soluble contaminating materials are poured off. Large contaminating materials form a black spot at the bottom of the transparent flagella pellet. This material is physically removed and discarded. The end product derived from 20 liters of bacterial culture is approximately 100 mg of purified flagella.

EXAMPLE 2

Flagellin is produced by acidifying the flagella at a pH of approximately 2 for 12 hours. This treatment dissociates the flagellar proteins to produce monomers of flagellin which have a molecular weight of approximately 30,000. The monomers reassemble into the polymerized flagella when allowed to stand at neutral pH for a period of at least 24 hours.

EXAMPLE 3

Gluteraldehyde is a divalent cross-linking compound which covalently attaches the peptide to the flagella and further fixes the flagella preparation. These methods of conjugating a functional group to a protein are well-known to one of ordinary skill in the art. Other chemical cross-linking reagents or chemical antigen derivatives, such as dinitrofluorobenzene are effective.

EXAMPLE 4

The conjugated flagella preparation is purified by dialysis, centrifugation, or any other standard method. The material is then resuspended in saline at a concentration approximating 100 µg/ml. This preparation is effective in low doses between 1 and 100 µg per injection. A dose of 10 µg produces a satisfactory response in many situations. The material can be injected by any convenient route, intravenous, subcutaneous, intramuscular, or intraperitoneal. The subcutaneous or intramuscular route is usually the most convenient for many vaccine purposes.

EXAMPLE 5

Detoxification of Ra-LPS (Ra-detox) is performed as follows: Ra-LPS obtained from *E. coli* EH-100 (10.0 mg) is suspended in 5.0 ml of water, sonicated for 15 minutes, and incubated at 100° C. for 5 minutes. One-thirtieth volume of triethylamine is added to the sample immediately after removal from incubation and is added to the sample immediately after removal from incubation and mixed well. This sample is allowed to stand at room temperature (22° C.) for 4 days. The sample is then lyophilized and the free fatty acids liberated by the treatment is extracted with hexane. The remaining residue constitutes the Ra-detox. Analytical TLC of the sample hydrolyzed in 0.1M HCl[17] revealed that the pattern of the MPL had shifted from the hexaacyl-pentaacyl to the pentaacyl-tetracyl forms. A single 3-hydroxymyristic acid at the 3 position of the lipid A is thought to be released resulting in the formation of predominantly pentaacyl Ra-LPS with reduced endotoxic activity.[18] Detoxified LPS can be prepared from a variety of other LPS forms, including, but not limited to, the Ra-LPS from *S. minnesota* R60 or *S. typhimurium* TV119 as well as the SR-LPS from *S. typhimurium* SF1512 and used as adjuvants.

[17]Qureshi, N., et al., "Purification and structural determination of nontoxic lipid A obtained from the lipopolysaccharide of *Salmonella typhimurium*", J. Biol. Chem., Vol. 257, pgs. 11808–11805 (1982)

[18]Louis, et al., supra

EXAMPLE 6

An ELISA assay is used for the determination of antibody directed against the trinitrophenol hapten. It is a modification of the method originally published by Saunders.[19]

[19]Saunders, G. C., "The art of solid phase enzyme immunoassay including selected protocols", *Immunoassays in the Clinical Laboratory*, Alan R. Liss, New York, pgs. 111–112 (1979)

The assay uses a protein, bovine serum albumin, hydrogel to reduce denaturation of proteins adherent to the plastic support and the use of proteins and surfactants to reduce nonspecific adsorption of proteins which tend to increase background and reduce sensitivity. Glutaraldehyde is used to attach antigen to BSA coated 96-well microtiter plates. Unbound glutaraldehyde is washed off. Antigen added to the plates attaches to the plate covalently via the free aldehyde groups of gluteraldehyde.

Remaining aldehyde groups are blocked with lysine and the plate is ready to use. The plates are incubated with various dilutions of antiserum, washed and then a second antibody such as peroxidase-conjugated goat anti-mouse IgG or one of the subclasses. The plates are washed and substrate (e.g., orthophenylene diamine with peroxide) is added. The resulting absorbance at 492 nm is read by a Titertek Multiscan photometer. The titer of antibody is calculated as the dilution of antiserum required to produce a ⅓ to ½ maximal optical density of the background. This is normalized by comparison to a reference antiserum simultaneously with the sample. This facilitates comparison of titers run on different days. The relative avidity of antibodies in relation to one another is estimated by analysis of the slope of the curve of optical density versus serum dilution.

Similar ELISA assays can be developed for many antigens including proteins, peptides and polysaccharides by those of ordinary skill in the art. In addition, one to four molar ammonium thiocyanate can be added to the ELISA wells after the first antibody to promote detachment of low avidity antibodies and thereby provide a more quantitative measure of avidity.

EXAMPLE 7

In the following experiment, 25 µg of flagella conjugated with an average of 4 TNP molecules per flagella is administered to mice via a hind footpad. The TNP-conjugated flagella is administered in a volume of 0.5 ml of saline. Antibody specific for TNP is measured at the following times after administration of the TNP-conjugated flagella: 8 days, 19 days, 30 days, 50 days and 90 days. The results of this experiment are shown in FIG. 1. As can be seen, the immune response to the TNP-conjugated flagella is still significantly high even after 90 days. The response to conventional TNP conjugates, such as TNP-conjugated hen egg albumin is much shorter in duration and the antibody titers are much lower. Animals frequently do not respond at all with detectable antibody to a hapten on a soluble protein carrier after a single injection.

EXAMPLE 8

Figure 2:
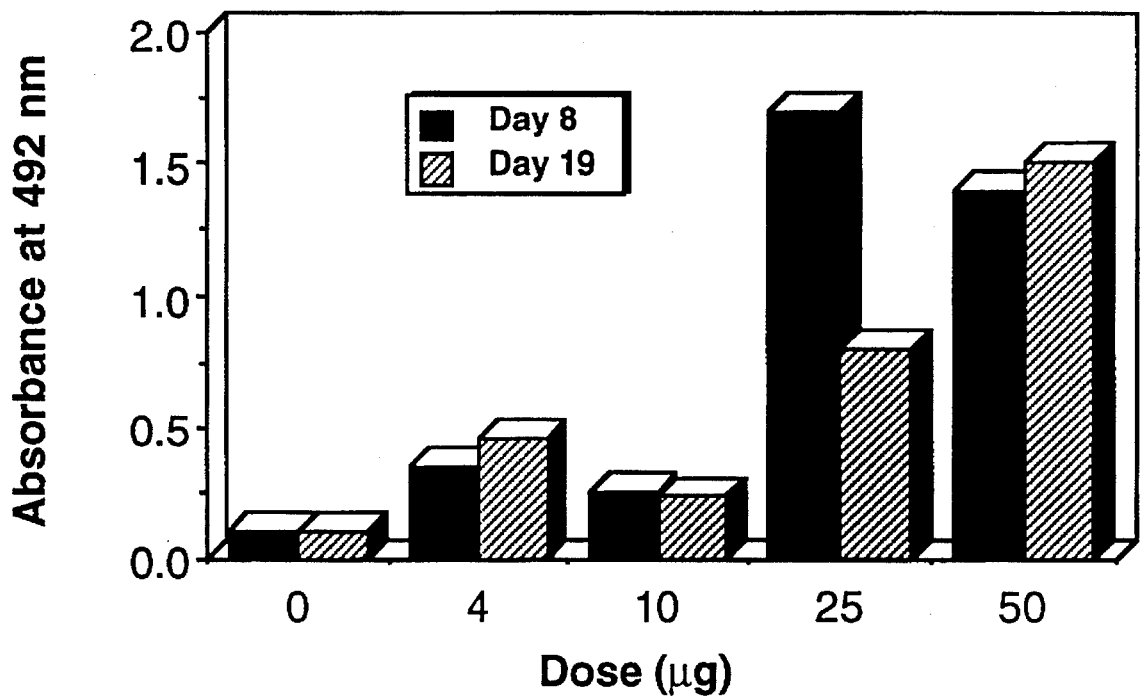
FIG. 2 is a graph illustrating the dose response of a mouse immunized with TNP conjugated to flagella protein from Salmonella.

The dose response of a mouse is measured by administering varying doses of TNP-conjugated flagella. Flagella conjugated with an average of 4 TNP molecules per flagellin molecule (molecular weight approximately 40,000) is administered to mice via a hind footpad. The TNP-conjugated flagella is administered in a volume of 0.5 ml of saline. The following concentrations of TNP-conjugated flagella are administered to mice: 4 µg, 10, µg, 25 µg and 50 µg. The antibody produced in response to the TNP-conjugated flagella is measured 8 days and 19 days after administration of the TNP-conjugated flagella. The results of this experiment are shown in FIG. 2.

EXAMPLE 9

Figure 3:
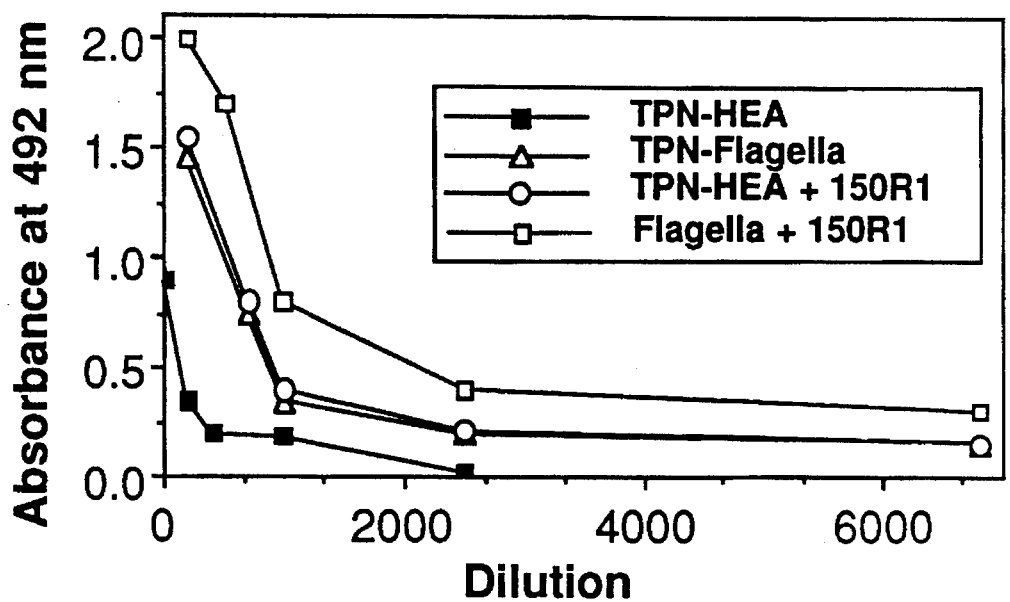
FIG. 3 is a graph comparing the immune response of a mouse immunized with TNP conjugated to hen egg albumin (HEA) and TNP conjugated to flagella protein from Salmonella. The graph also compares using the two compounds with and without the adjuvant T150R1.

A comparison of the immunologic response of mice to TNP conjugated to hen egg albumin (HEA) and TNP conjugated to bacteria flagella protein is shown in FIG. 3. In this experiment, TNP is conjugated to HEA using the reactive derivative trinitrobenzene sulfonic acid (TNBS) in the same fashion as flagella. 100 µg of the TNP-conjugated HEA or 25 µg of TNP-conjugated flagella are administered to mice via a hind footpad. Ten days after administration of the TNP-conjugated proteins, antibody titer is measured according to Example 6. As shown in FIG. 3, the TNP-conjugated flagella induced a significantly greater immune response, as measured by antibody titer, than did the TNP-conjugated HEA. It should be noted that the amount of TNP-HEA administered in this experiment is four times the amount of TNP-conjugated flagella (100 µg of TNP-HEA versus 25 µg of TNP-conjugated flagella).

EXAMPLE 10

The same preparations used in Example 9 are administered to mice with the addition of 1.0 mg of T150R1 adjuvant. 100 µg of the TNP-conjugated HEA or 25 µg of TNP-conjugated flagella are administered to mice via a hind footpad. Ten days after administration of the TNP-conjugated proteins with the adjuvant, antibody titer is measured according to Example 6. The results of these experiments are summarized in FIG. 3. As shown, the adjuvant raised the immune response to both the TNP-conjugated HEA and the TNP-conjugated flagella. However, the TNP-conjugated flagella induced a significantly greater immune response than did the TNP-conjugated HEA. Similar experiments were done with keyhole limpet hemocyanin (KLH) instead of HEA with similar results. KLH was more effective than HEA, but less effective than flagella as a carrier.

EXAMPLE 11

Because the block copolymer adjuvants appear to act via distinct mechanisms, there is a possibility of incorporating them in more complex formulations to optimize activity for particular applications. $TNP_{10}$-HEA is prepared in oil-in-water emulsions with 1.0 mg of the surface-active copolymer with the following formula:

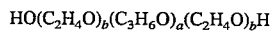

wherein the molecular weight of the hydrophobe ($C_3H_6O$) is approximately 4600 and the percentage of hydrophile ($C_2H_4O$) is approximately 10% by weight.

Figure 4:
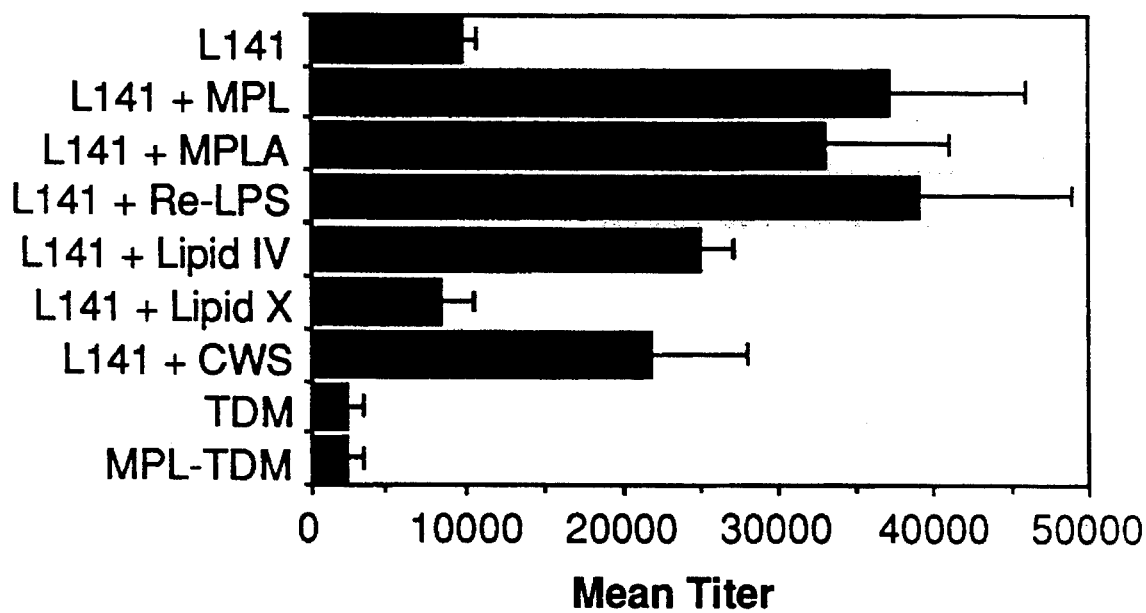
FIG. 4 is a graph illustrating the production of IgG antibody response in mice in response to immunization with $TNP_{10}$-HEA and various adjuvants.

The surface-active copolymer is prepared in oil-in-water emulsions with $TNP_{10}$-HEA and a variety of lipid A derivatives including the Re-LPS and monophosphoryl lipid A from two sources. In addition, two precursors of lipid A, lipid IVA and lipid X are evaluated, The LPS and both lipid A preparations produced a striking increase in antibody response over that of the triblock copolymer alone. The oil (2% Squalane) and copolymers are mixed with dry trinitrophenyl conjugated hen egg albumin ($TNP_{10}$-HEA) and subsequently homogenized in PBS, pH 7.4, with 0.2% Tween-80. Mice are given 50 µL divided between both rear footpads. The doses per animal are 50 µg antigen, 0.6 mg L141, and 0.1 mg T150R1. The combination of adhesive and ionophore copolymers produced a marked increase in antibody response over that of either alone. The results of this experiment are found in FIGS. 4 and 5.

The bars labeled MPL-TDM and TDM are preparations commercially available from Ribi Immunochemical (Hamilton, Mont.). These adjuvants are prepared according to instructions supplied with the adjuvants.

As can be seen, the commercial adjuvants MPL-TDM and TDM invoked a minimal response in the mouse compared with other preparations. However, the various combinations of copolymers and lipid A derivatives caused unexpectedly high titers of antibody.

EXAMPLE 12

Adjuvant effects of copolymers with lyophilized antigen in oil-in-water emulsions of 2% squalane are evaluated. Oil and copolymer are mixed with dry $TNP_{10}$-HEA and subsequently homogenized in PBS, pH 7.4, with 0.2% Tween-80. Mice are given 50 µL divided between both rear footpads. The doses per animal are 50 µg antigen, 0.6 mg triblock copolymer designated L141 and 1 mg of the copolymer designated T150R1.

The copolymer designated L141 has the following structure:

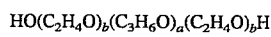

wherein the molecular weight of the hydrophobe ($C_3H_6O$) is approximately 4600 and the percentage of hydrophile ($C_2H_4O$) is approximately 10% by weight The copolymer designated T150R1 is an ionophore and has the following formula:

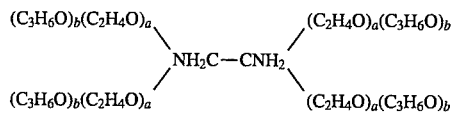

wherein a is equal to approximately 5 and b is equal to approximately 32.

Figure 5:
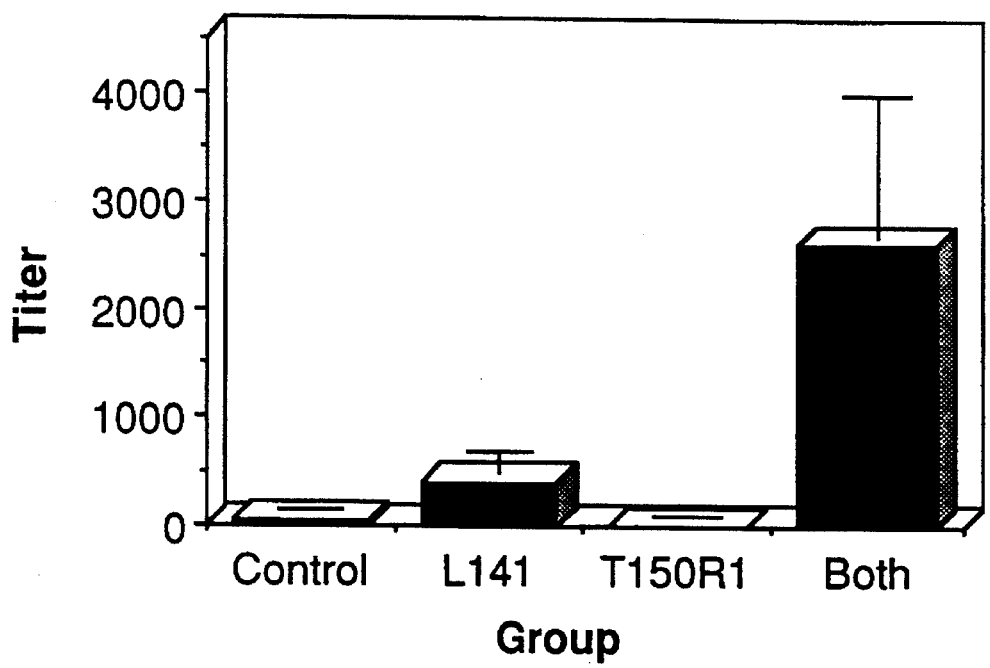
FIG. 5 is a graph illustrating the adjuvant effects of copolymers with lyophilized $TNP_{10}$-HEA antigen in oil-in-water emulsions of 2% squalane.

The results of this experiment is shown in FIG. 5. As can be seen, the combination of the triblock copolymer and the reverse octablock copolymer gives a synergistic adjuvant effect.

EXAMPLE 13

Figure 6:
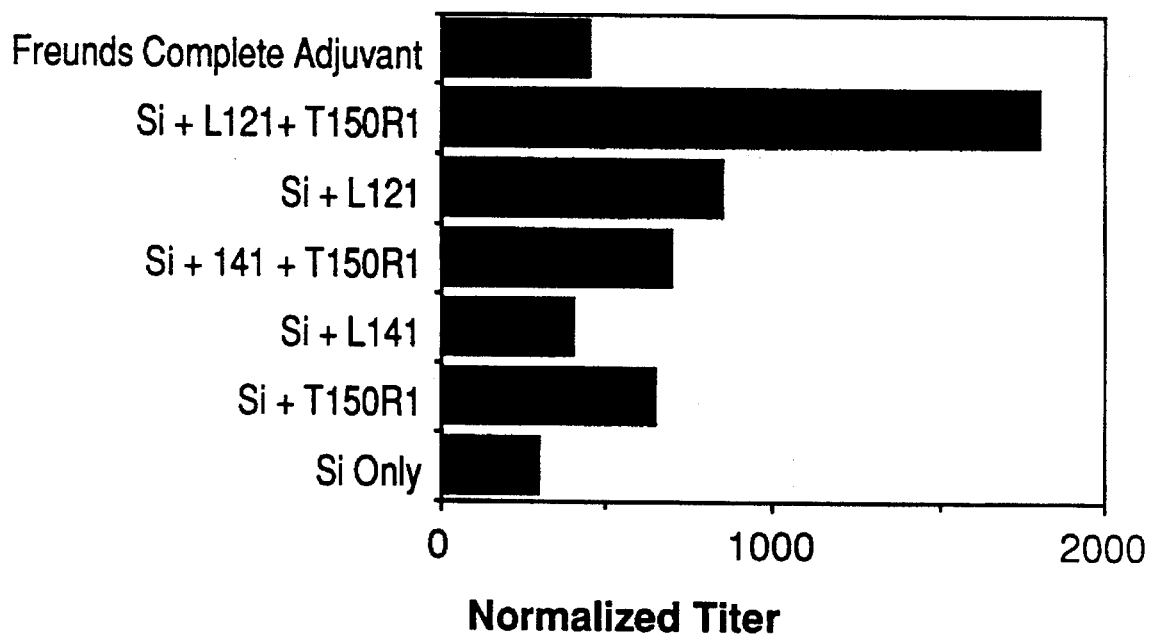
FIG. 6 is a graph illustrating the adjuvant effects of an oil emulsion of silica with and without selected copolymers.

In this experiment, 50 µg lyophilized $TNP_{10}$-HEA (10.4 TNP per mole) is administered to mice in 50 µL doses split between both footpads of a mouse. The dry antigen is mixed with oil prior to emulsification with saline. The Freund's Complete Adjuvant (FCA)(Grand Island Biologicals) is made up as 60% oil in saline with no additives. All other preparations are 60% oil with 50 µL Span-80, 10 µL Tween-80, and 15 mg silica (5 µm Minusil) in a dose of 1.6 µL emulsion. Where used, triblock copolymers are included at a concentration of 0.6 mg and reverse octablock copolymers are at a concentration of 0.1 mg per mouse. The data is a composite from two experiments with 5 to 15 mice per group. (See FIG. 6)

The triblock copolymer designated L121 is as follows:

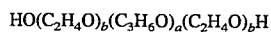

wherein the molecular weight of the hydrophobe ($C_3H_6O$) is approximately 4000 and the percentage of hydrophile ($C_2H_4O$) is approximately 10% by weight.

The copolymer designated L141 is as follows:

wherein the molecular weight of the hydrophobe ($C_3H_6O$) is approximately 4600 and the percentage of hydrophile ($C_2H_4O$) is approximately 10% by weight and 0.1 mg of the octablock copolymer with the reverse copolymer designated T150R1 as follows:

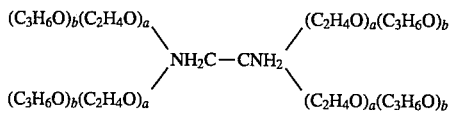

wherein a is equal to approximately 5 and b is equal to approximately 32.

All of the formulations had silica as a base except the Freund's Complete Adjuvant (FCA). As can be seen, all of the compositions with the copolymers had increased adjuvant activity and are more effective than FCA. (See FIG. 6)

The combination of oil and silica is more effective then either alone. The 60% oil emulsion, by itself, produces a mean titer of 100 and the silica by itself produces a mean titer of less than 20 while the combination induces a titer of over 300 at 30 days after a single injection. The silica emulsion, by itself, or with copolymers, is also found to be more effective than the oil emulsion alone for immunizing chickens for bursal disease virus or for immunizing rabbits with a variety of protein antigens. Finally, it is found that other surfactants can be substituted for the Span and Tween so long as they produce stable emulsions. The silica emulsions produce only mild local reactions compared to the intense, chronic inflammatory reactions induced by Freund's Complete Adjuvant. In addition, the silica admixtures are unable to induce autoimmune adjuvant arthritis. This is a major advantage over the most commonly used adjuvant for producing antisera, Freund's Complete Adjuvant.

EXAMPLE 14

Figure 7:
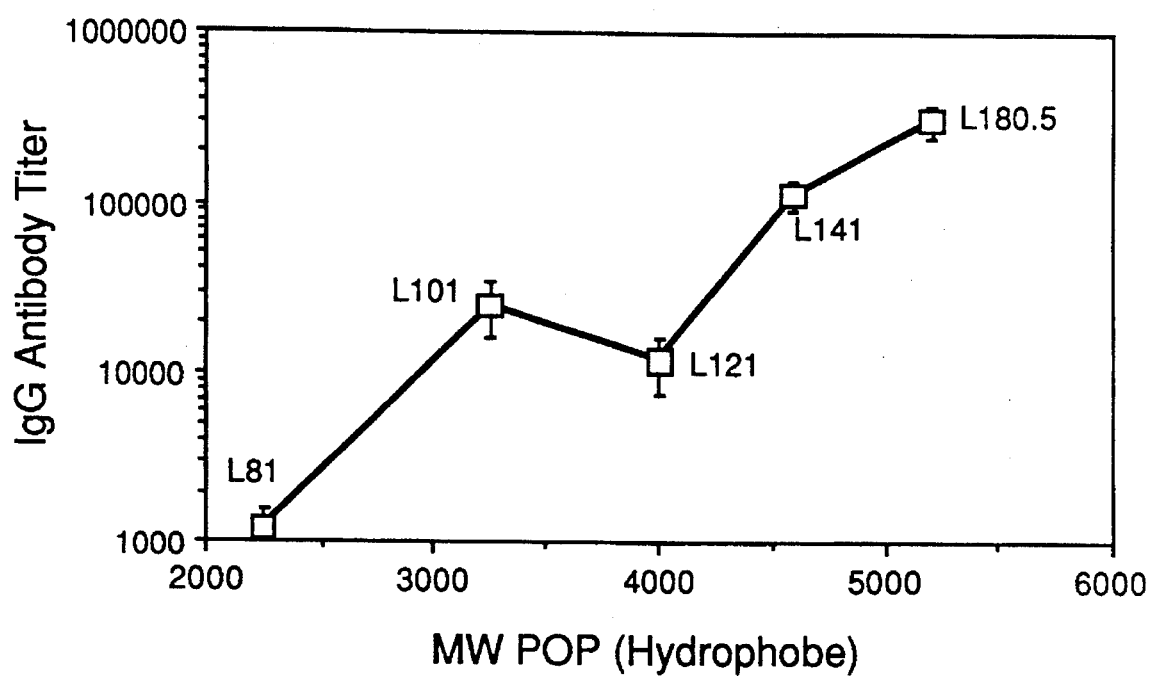
FIG. 7 is a graph comparing copolymer adjuvants administered with soluble antigen, $TNP_{10}HEA$.

Groups of five to ten mice were immunized with TNP-HEA in a 2% squalane-in-water emulsion containing 1 mg of each of the copolymers indicated in FIG. 7. The time courses of the antibody responses are similar in each of the groups except L81 which induces only a transient response. The liters peak at approximately one month after injection and persisted for over three months. The animals are boosted on day 90 after immunization. They are bled again one week post boost. The copolymers with 10% or less polyoxyethylene (POE) all induced strong immune responses. Copolymer L122 is a poor adjuvant. The adjuvant activity of copolymers with a range of POE chain lengths and the polyoxypropylene (POP) chains with molecular weights of 5200 (L180.5, L181.5 and L182.5) follow the pattern established previously for the series of smaller copolymers L121, L122 and L123. Copolymers with more than 10% POE are again found to be ineffective adjuvants.

The mean titers stimulated by the copolymers with 10% or less POE of each length of POP chain increases with increasing molecular weight of the POP hydrophobe as shown in FIG. 7. While there is variability between and among groups, the general pattern of increasing titer with increasing molecular weight of hydrophobe is observed repeatedly.

Figure 8:
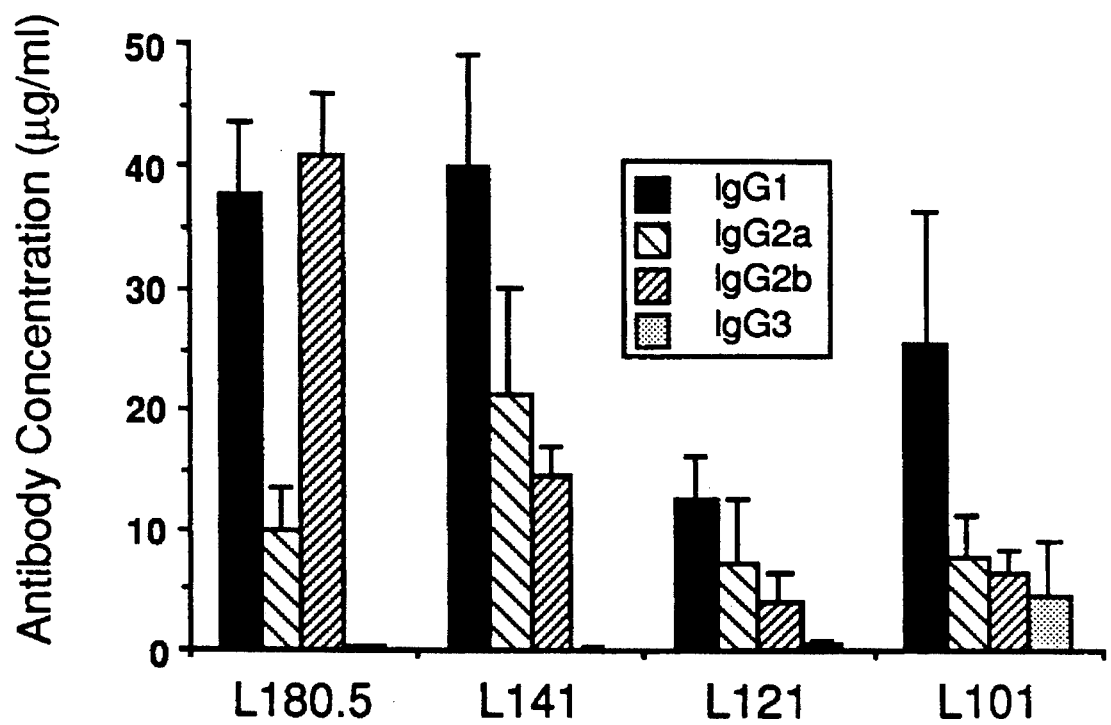
FIG. 8 shows the influence of molecular weight of POP on antibody titer to $TNP_{10}HEA$.
Figure 9:
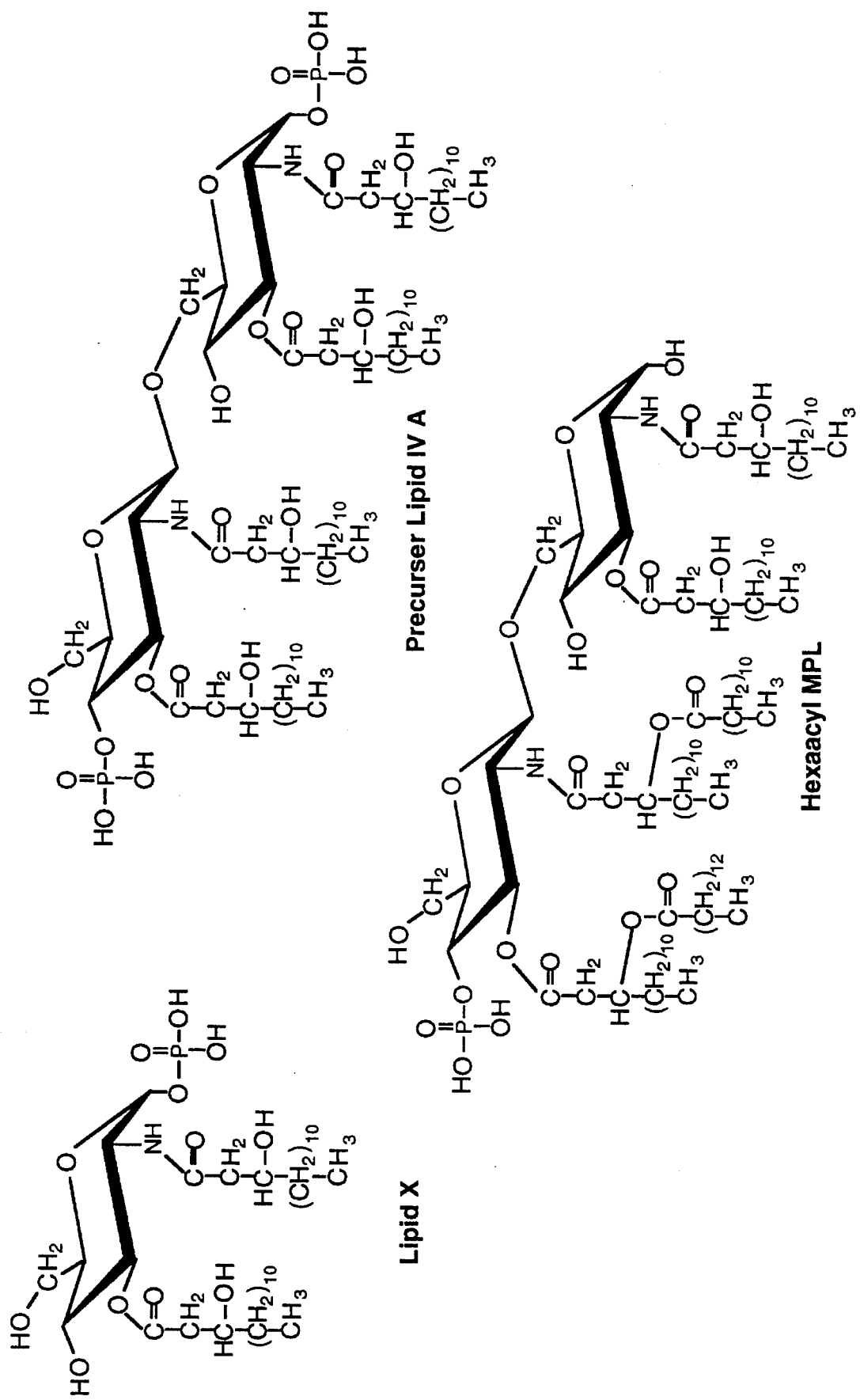
FIG. 9 shows the chemical structure of lipid A derivatives including lipid X, lipid IVA, monophosphoryl lipid A and (hexacyl MPL).

The isotype of antibody is measured at multiple time points using an ELISA assay with calibrated class specific antisera. As shown in FIG. 8, the copolymer preparations which were effective adjuvants for inducing antibody induced distinctly different patterns of isotype. The lower molecular weight preparation, L101, induces a predominant IgG1 response with lesser amounts of IgG2a and IgG2b. Increasing molecular weight of the hydrophobe increases the proportion of IgG2, especially IgG2b. Interestingly, the production of the IgG3 isotype follows the opposite pattern with the highest titers produced by the lower molecular weight preparations, L121 and especially L101. The ratio of IgG1 to IgG2b antibody increases in a nearly linear fashion with molecular weight of the hydrophobe as shown in FIG. 8. The distribution of isotypes is measured at multiple intervals following the 28 day determination. The isotype patterns produced by each copolymer tend to persist during subsequent assays.

EXAMPLE 15

Figure 13:
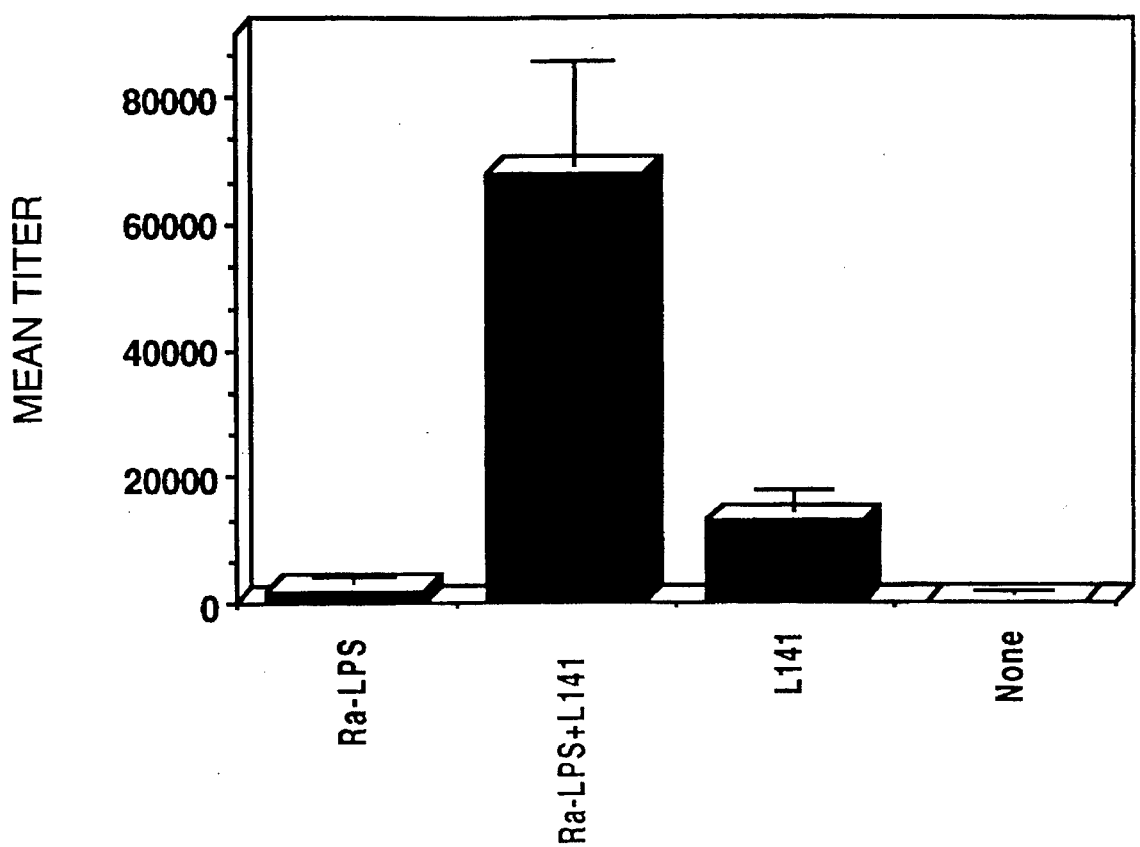
FIG. 13 shows the IgG response on day 28 when TNP-HEA is administered to mice with and without detoxified RaLPS and/or L141 copolymer.
Figure 14:
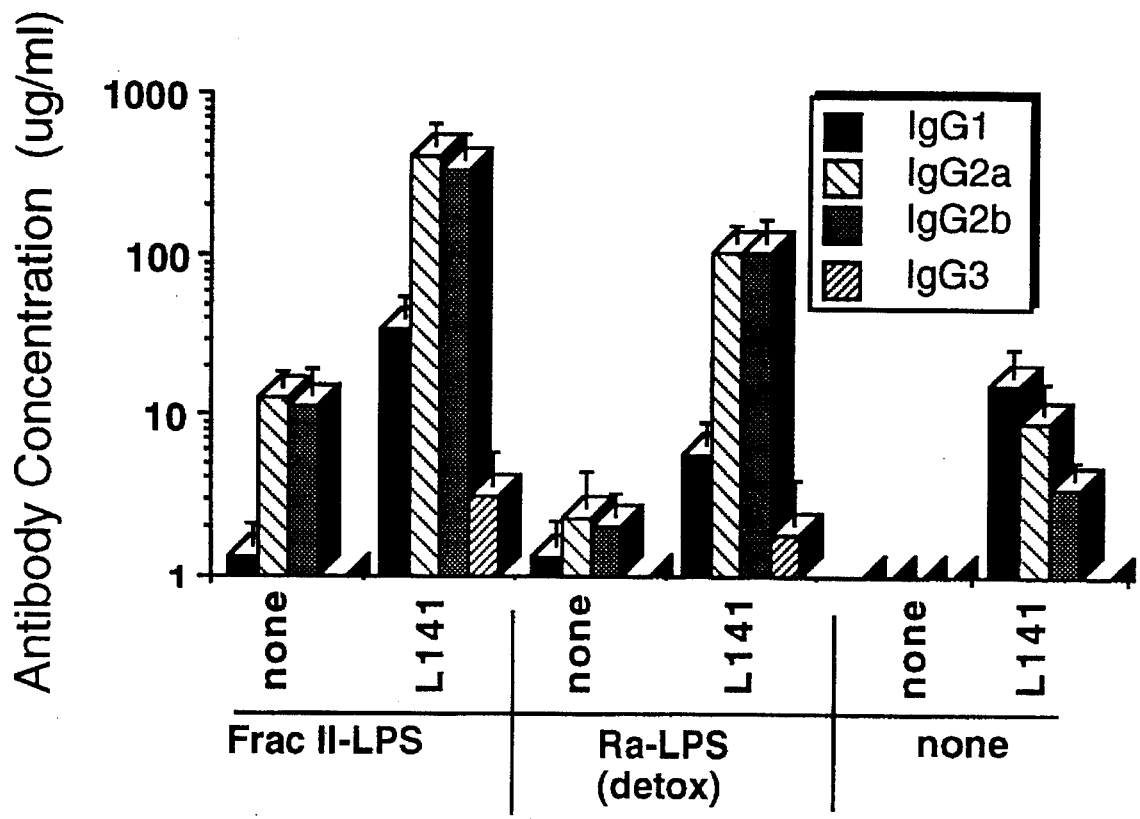
FIG. 14 shows the isotype response to $TNP_{10}HEA$ induced by whole toxic lipopolysaccharide and detoxified RaLPS with and without the copolymers present.

Groups of mice are immunized with 50µg of TNP-HEA in a squalane-in-water emulsion containing 1 mg of copolymer 141 and/or 100 µg of detoxified RaLPS. FIG. 13 shows a synergistic response when the detoxified RaLPS and the L141 are admixed with TNP-HEA and administered to mice. FIG. 14 shows the isotype of IgG induced by each of the adjuvant combinations plus a comparison with a toxic LPS. After 30 days, the isotype of antibody is determined for several of the endotoxin derivatives and fractions with reduced toxicity. Copolymer 141, by itself, produces a predominant IgG1 isotype antibody response with lesser amounts of IgG2a and IgG2b with only a trace of IgG3. Detoxified RaLPS reduced the amount of IgG1 antibody to the TNP-HEA while it markedly increased the IgG2a and IgG2b antibodies. In similar experiments, the non-toxic *S. sphaeroides* LPS did not significantly increase the total IgG titer, but it did reduce the amount of IgG1 antibody and increase the amounts of IgG2a and IgG2b. The other non-toxic and detoxified LPS derivatives both increased the titer and shifted the balance of isotypes towards IgG2a and IgG2b. The antigen injected without any adjuvant produces no detectable antibody.

EXAMPLE 16

Comparisons are made between trehalose dimycolate and the L141 copolymer in combination with monophosphoryl lipid A. Mice are immunized with 50 µg of TNP-HEA in a oil in water emulsion with the adjuvants as shown. The emulsions contained 50 µg of MPL and/or TDM per dose. The mice are bled on day 28.

Figure 15:
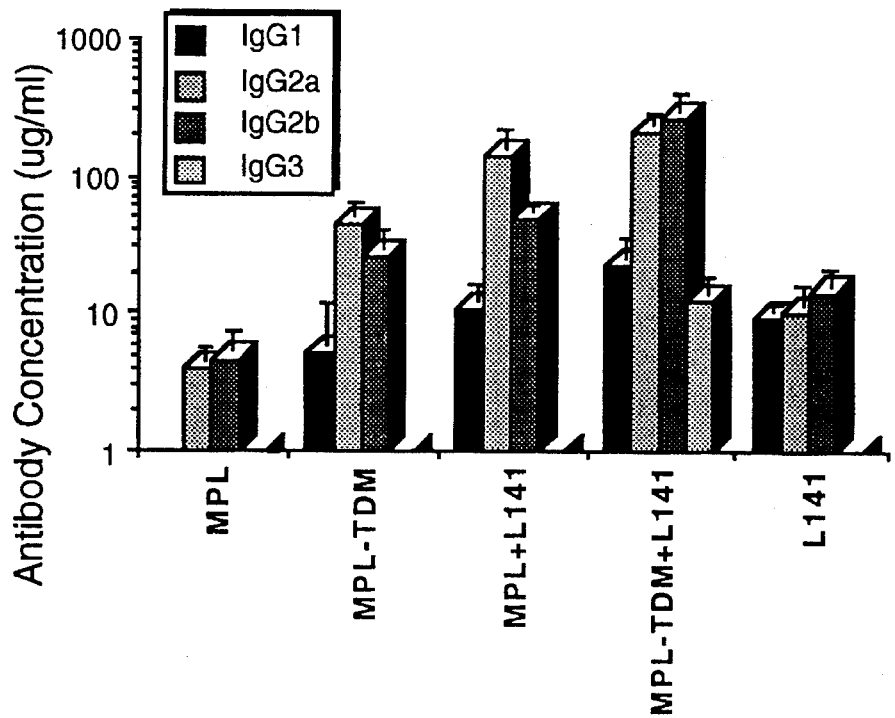
FIG. 15 shows the IgG isotype concentrations to $TNP_{10}HEA$ induced by L141 and/or TDM in combination with MPL.

The combination of L141 with MPL produced higher titers than TDM-MPL combination. The titers are predominantly of the IgG2a subclass. As shown in FIG. 15, the combination of all three materials produced the highest IgG2 titers of all with a significant addition of IgG3.

EXAMPLE 17

It has long been recognized that lipopolysaccharides from gram negative bacteria are effective immunomodulating agents and immunologic adjuvants. However, the toxicity of these materials has impeded their development as adjuvants. Recently, a means of reducing their toxicity while retaining substantial adjuvant activity have been reported. This method included the removal of a phosphate group from lipid A to produce monophosphoryl lipid A (MPL). In addition, the removal of one or more fatty acid chains from the lipid A moiety also reduces toxicity. Some types of LPS, particularly that from *Rhodopseudomonas sphaeroides* (see FIG. 11 for structure), are inherently non-toxic. Its structure is very similar to that of toxic lipid A. Rietchsel proposed that the entire structure of lipid A is required for toxicity and demonstrated that many modifications can reduce its toxicity.[20]

[20]Rietchsel, E., et al., "Bacterial Endotoxins: Relationships Between Chemical Structure and Biological Activity", *Immunologic Adjuvants and Vaccines*, Vol. 179, Ed. by Gregoriadis, G., et al., Plenum Press, pgs. 61–74

The present experiment is designed to evaluate the potential of a series of LPS derivatives to act as adjuvants in combination with nonionic block copolymer surfactants. The LPS derivatives are selected to evaluate a spectrum of structural modifications which are selected to evaluate several means of reducing toxicity and evaluating structure with the isotype and intensity of immune response. These agents are used by themselves and in combination with a block copolymer adjuvant, L141, to evaluate synergy between agents which appear to act via distinct mechanisms.

Finally, trehalose 6,6' dimycolate (TDM) has been reported to be an adhesive adjuvant which binds antigen to the surface of oil drops. Studies are shown to compare the adjuvant activity of TDM with that of block copolymers in combination with LPS derivatives.

Animals

Groups of 7–10 week old female ICR (outbred) mice obtained from Charles River Laboratories, Raleigh, N.C. are used.

Antigen Preparation

The trinitrophenyl (TNP) hapten is bound to recrystallized hen egg albumin (HEA). TNP is conjugated to HEA using 5 mM trinitrobenzene sulfonate in borate buffer, pH 8.2.[21] The extent of trinitrophenylation is determined spectrophotometrically using an extinction coefficient of 15,400 at 350 nm. Eight to nine TNP units are bound per mole of HEA.

[21]Justine S. G., et al., *Methods in Immunology*, 3rd Ed., Chapter 18, pgs. 153–158 (1977)

Adjuvants $Rd_1$-LPS from *S. minnesota* R7, Rc-LPS from *S. typhimurium* SL684, and Ra-LPS from *E. coli* EH-100 are purchased from Sigma Chemical Company, St. Louis, Mo. MPL from *S. minnesota* R595 is purchased from Ribi ImmunoChem Research, Inc., Hamilton, Mont. Cultures of *S. minnesota* R345, *S. minnesota* R60, and *S. typhimurium* SF1512 are obtained from Institute für Experimentelle Biologie und Medizin, Borstel, West Germany. Cultures of *E. coli* 09 and 058 are obtained from Statens Seruminstitut, DK-2300 Copenhagen, Denmark. Culture of *E. coli* D31m4 is obtained from Genetic Stock Center, Department of Human Genetics, Yale University School of Medicine, New Haven, Conn.

The growth of the temperature-sensitive mutants of *E. coli* MN7 and *S. typhimurium* i50 as well as the preparation of lipid X and precursor lipid IVA, respectively have all been described previously in Takayama, K., et al. and Raetz, C. R. H., et al., which are hereby incorporated in their entirety by reference.[22,23] The growth of *E. coli* D31m4 and the preparation of the purified Re-LPS are described by Qureshi, et al., which is incorporated herein by reference.[24] MPL is prepared from the D31m4 and Re-LPS according to Qureshi, N., et al., which is incorporated herein by reference.[25] This product contained a mixture of a hexaacyl and a minor pentaacyl MPL.

[22]Takayama, K., et al., "Fatty acyl derivatives of glucosamine 1-phosphate in *Escherichia coli* and their relation to lipid A. Complete structure of a diacyl GlcN-1-P found in a phosphatidylglycerol-deficient mutant", *J. Biol. Chem.*, Vol. 258, pgs. 7379–7385 (1983)

[23]Raetz, C. R. H., et al., "Isolation and characterization of eight lipid A precursors from a 3-deoxy-D-manno-octylosonic acid deficient mutant of *Salmonella typhimurium*", *J. Biol Chem.*, Vol. 260, pgs. 16080–16088 (1985)

[24]Qureshi, et al., "Complete structural determination of lipopolysaccharide obtained from deep rough mutant of *Escherichia coli*. Purification by high performance liquid chromatography and direct analysis by plasma desorption mass spectrometry." *J. Biol. Chem.*, Vol 263, pgs. 11971–11976 (1988)

[25]Qureshi, N., et al., "Purification and structural determination of nontoxic lipid A obtained from the lipopolysaccharide of *Salmonella typhimurium*", J. Biol. Chem., Vol. 257, pgs. 11808–11815 (1982)

Figure 10:
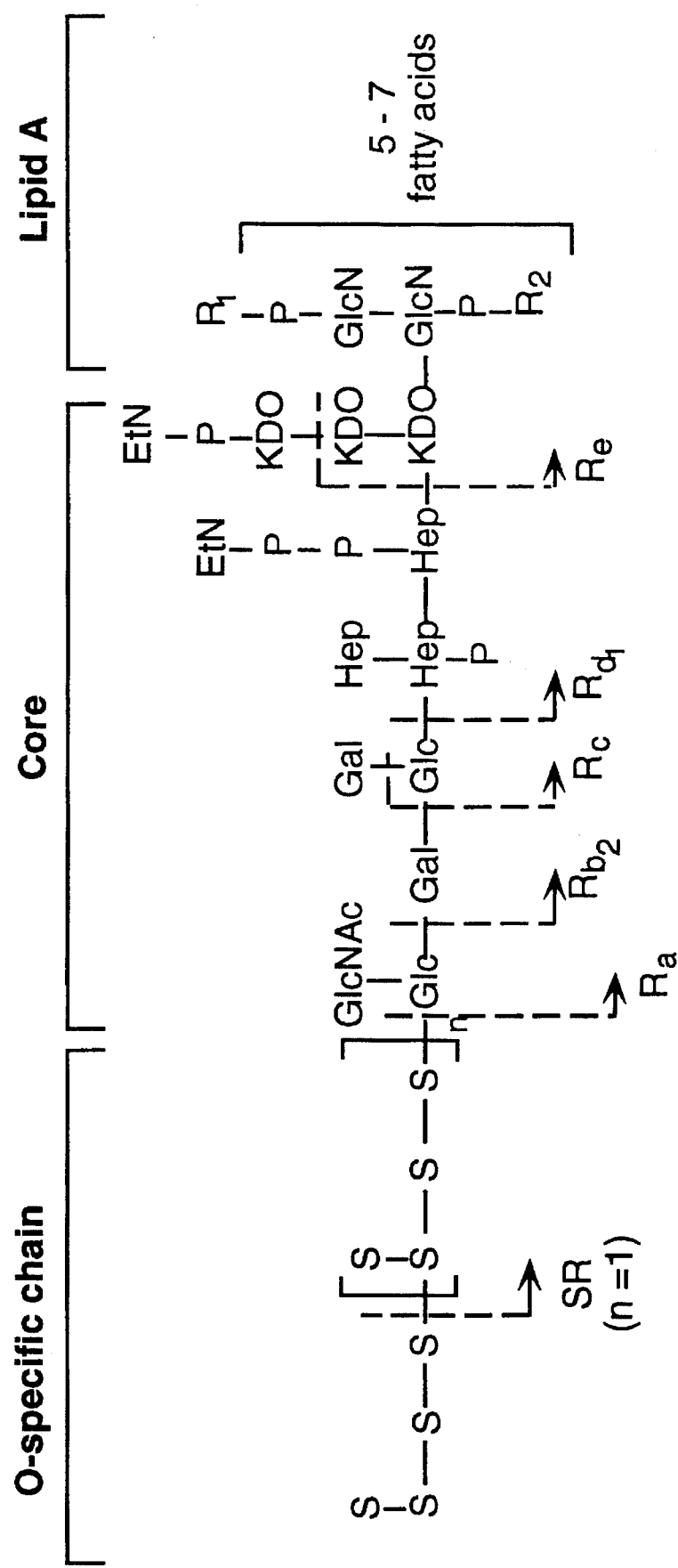
FIG. 10 shows the structures of rough chemotype lipopolysaccharides of Enterobacteriaceae (SR to Re). Abbreviations: S, sugar; Glc, glucose; GlcNAc, N-acetyl glucosamine; Gal, galactose; Hep, L-glycero-D-mannoheptose; P, phosphate; EtN, ethanolamine; KDO, 2-keto-3-deoxyoctonate; GlcN, glucosamine; R, and $R_2$, phosphoethanolamine or aminoarabinose (not present in *E. coli*). SR to Re indicates incomplete forms or rough chemotypes of LPS. The Rc and $Rd_1$ chemotypes lack the phosphate attached to Hep.
Figure 11:
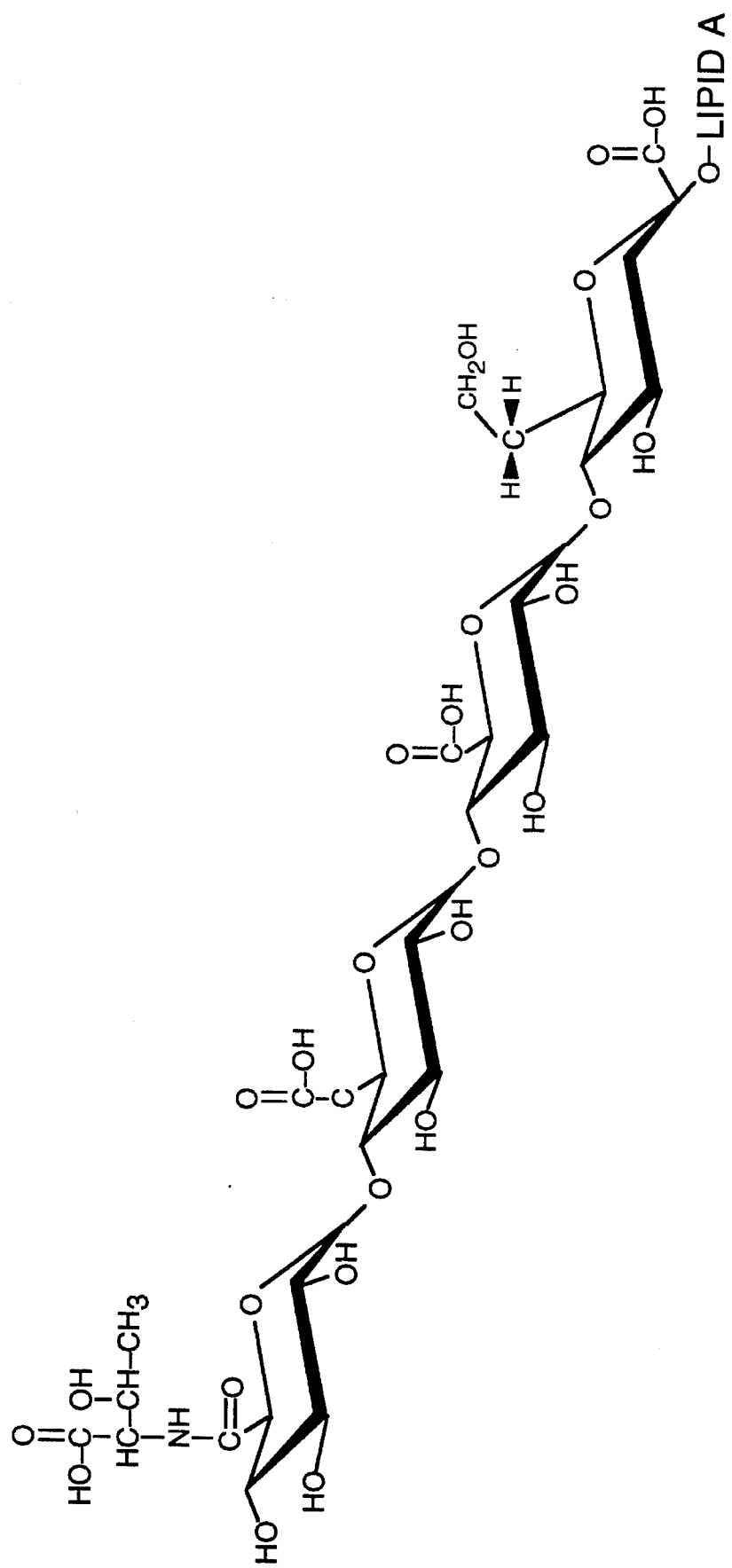
FIG. 11 shows the structure of *R. sphaeroides* LPS.
Figure 12:
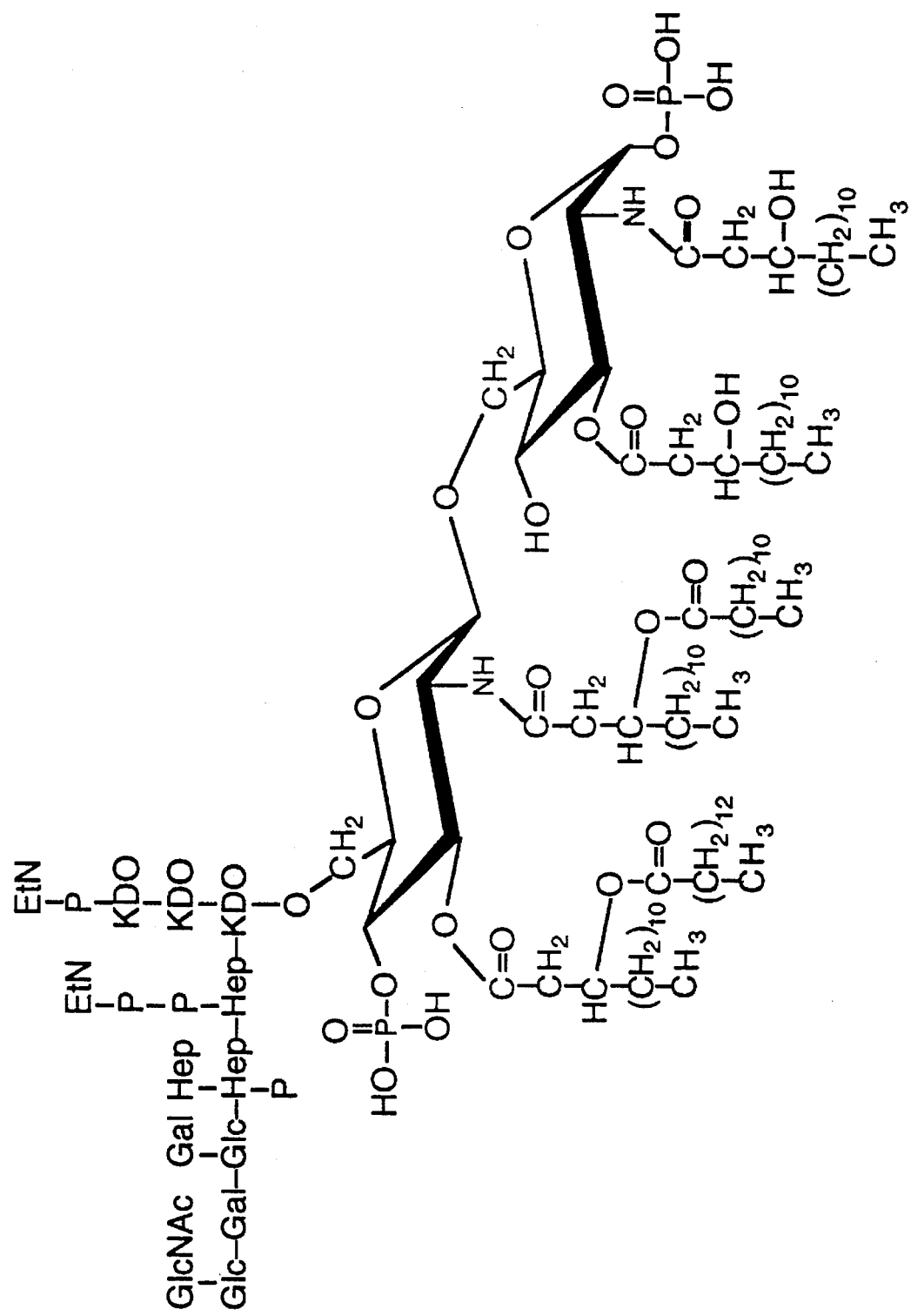
FIG. 12 shows the structure of detoxified RaLPS.

The rough chemotype lipopolysaccharide from *S. minnesota* R345, *S. minnesota* R60, *S. typhimurium* SF1512 and *R. sphaeroides* ATCC 17023 are prepared by the method of Galanos, et al., with modifications.[26,27] The structures of the series of rough chemotype LPS from the smallest (Re-LPS) to the largest (SR-LPS) are shown in FIG. 10. The structure of the *R. sphaeroides* LPS is shown in FIG. 11.

[26]Galanos, C., et al., "A new method for the extraction of lipopolysaccharides", *Eur. J. Biochem.*, Vol. 9, pgs. 245–249 (1969)

[27]Qureshi, N., et al., "Position of ester groups in the lipid A backbone of lipopolysaccharides obtained from *Salmonella typhimurium*", *J. Biol. Chem.*, Vol. 258, pgs. 12947–12951 (1983)

*E. coli* 09 and 058 are grown in LB broth and the smooth chemotype lipopolysaccharides are prepared by the hot phenol-water extraction method of Westphal and Jann.[28]

The yields are 8.0 and 14.9% (dry weight) respectively for the LPS from *E coli* 09 and 058. The structure of the O-antigen region of the *E. coli* 058 LPS is determined to be:

[28]Westphal, et al., "Extraction with phenol-water and further applications of the procedure", *Methods Carbohydrate Chem.* Vol. 5, pgs. 83–91 (1965)

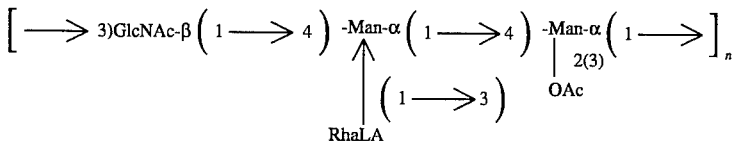

where RhaLA is 3-O-(R-1'-carboxyethyl)-L-rhamnose (rhamnolactylic acid).

The 09 LPS (100.7 mg) is dissolved in 2.0 ml of 0.2 M Tris-HCl, pH 7.8 containing 0.6% deoxycholic acid and fractionated on a 2.8×54 cm Bio-Gel P-100 column (Bio-Rad, Richmond, Calif.) at 37° C. using the same buffer. This procedure is similar to that of Vukajlovich, et al. which is incorporated herein by reference.[29] Two ml fractions are collected and assayed for both KDO and mannose. Based on these analyses, fractions 27–35 (I), 36–43 (II) and 44–51 (III) are pooled and extensively dialyzed against running water. These samples are finally desalted on a Bio-Gel P-4 column to yield 43.5 mg of I, 27.2 mg of II and 6.6 mg of III. These three samples are analyzed by sodium dodecyl sulfate-polyacrylamide gel electrophoresis. The electrophoresis showed that fraction I contained predominantly the smooth chemotype LPS, II contained a mixture of smooth and rough chemotype LPS and III contained mostly the rough chemotype LPS. These results are consistent with the mannose to total phosphorous molar ratios which are 9.2:1.0 for I; 5.3:1.0 for II; and 2.9:1.0 for III. The hexose region of the outer core of 09 LPS appears to have the type *E. coli* R1 whereas the inner core is the same for all Salmonella and *E. coli*. The structure of the O-antigen region of the 09 LPS is determined to be:

[29]Vukajlovich, et al., "Conversion of lipopolysaccharides to molecular aggregates with reduced subunit heterogeneity: Demonstration of LPS-responsiveness in 'Endotoxin-unresponsive $C_3H/HeJ$ splenocytes'", *J. Immunol.*, Vol. 130, pgs. 2804–2808 (1983)

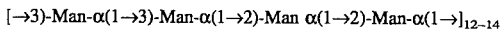

The lipid A precursors and derivatives (including MPL) are obtained from Dr. Kuni Takayama, VA Hospital, Madison, Wis. The MPL and MPL-TDM preparations are purchased from Ribi ImmunoChem Research, Inc., Hamilton, Mont. The nonionic block copolymer surfactant, L141, is obtained from CytRx Corporation, Atlanta, Ga. It consists of a central polymer of polyoxypropylene (POP) with a molecular weight of 4600 daltons and hydrophilic chains of polyoxyethylene (POE) on each end with a total molecular weight averaging 500 daltons.

Stimulation of Immune Response

The above mentioned additives, alone or in combination are lyophilized and incorporated into oil-in-water emulsions containing 2% squalane (hexamethyltetracosane). The final concentration yielded 50 µg TNP-HEA, 100 µg LPS, 50 µg MPL and MPL-TDM, and 1 mg copolymer L141 per mouse. Animals are given a subcutaneous injection in the hind footpad (40–50 µL volume) containing the above mentioned dosages of antigen and adjuvant according to specific group tested. Mice are bled at various time points throughout the course of the study via retro-orbital plexus using heparinized Natelson capillary tubes and plasma is stored at −70° C.

Antibody Detection Procedure

An evaluation of the immune response induced by each preparation is made using an Enzyme Linked Immunosorbant Assay (ELISA). Antigen is prepared by the reaction of picrylsulfonic acid with BSA fraction V. Microtiter plates are treated with 100 µL per well TNP-BSA (25 TNP units per mole BSA) at 0.5 µg/ml PBS, pH 8.4 overnight at 4 C. The antigen solution is replaced with 1% BSA in PBS, pH 7.4 and the plates are incubated for 1 hour at room temperature in order to block any sites left available for nonspecific binding of antibody. The plates are washed 4× with 0.05% poloxamer 188 in PBS, pH 7.4. Next, 100 µL of serial dilutions of test sera with 0.1% BSA and 0.1% poloxamer 188 in PBS, pH 7.4 are added and incubated for 1 hour at room temperature on an orbital shaker (200 rpm). The plates are then washed 3× and incubated for 90 minutes at 37 C. with affinity-purified horseradish peroxidase-conjugated goat antibody directed against mouse IgG or specific IgG subclass. A 1:2000 dilution of conjugate is used for all except IgG3, for this a 1:1000 dilution is used. Following this step, the plates are washed 3× and color development is achieved with orthophenylene diamine (OPD) HCL, 0.4 mg/ml, in citrate/phosphate buffer, pH 5.0. The reaction is stopped using 2.5N sulfuric acid ($H_2SO_4$) 15 minutes after the addition of OPD and read at 490 nm using a BIORAD model 3550 microplate reader. Titers are defined as the dilution of antiserum required to produce an absorbance of 1.0. Synergy is calculated by the following formula: titer of LPS+L141/titer of LPS or L14

Results

Figure 16:
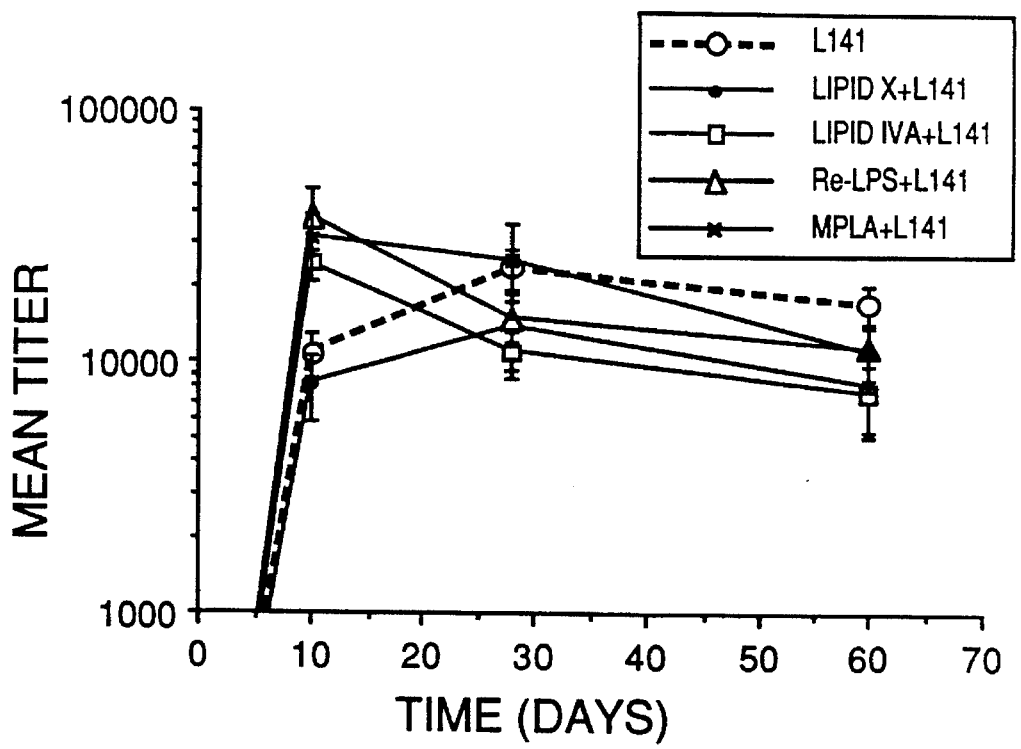
FIG. 16 shows the adjuvant effect of small LPS derivatives on the response to $TNP_{10}HEA$.

Groups of female outbred ICR mice are immunized in the hind foot pads with 50 µg of TNP-HEA in a 2% squalane-in-water emulsion containing 1 mg of copolymer L141 plus 100 µg of one of a series of lipid A derivatives as shown in FIG. 16. The smallest derivative, lipid X, suppressed the immune response at all time periods measured. Each of the other derivatives produced an accelerated response with higher titers at ten days after immunization but then produced moderately suppressed responses at 30 and 60 days.

Figure 17:
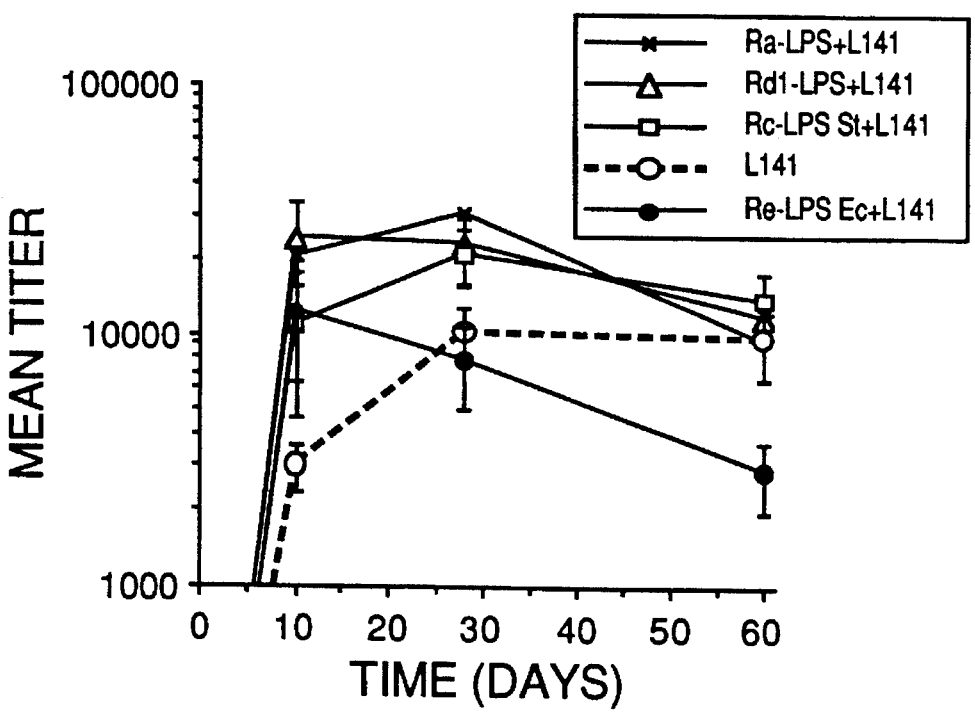
FIG. 17 shows the adjuvant effect for $TNP_{10}HEA$ of larger LPS mutant of defined chain lengths in combination with copolymer L141.
Figure 18:
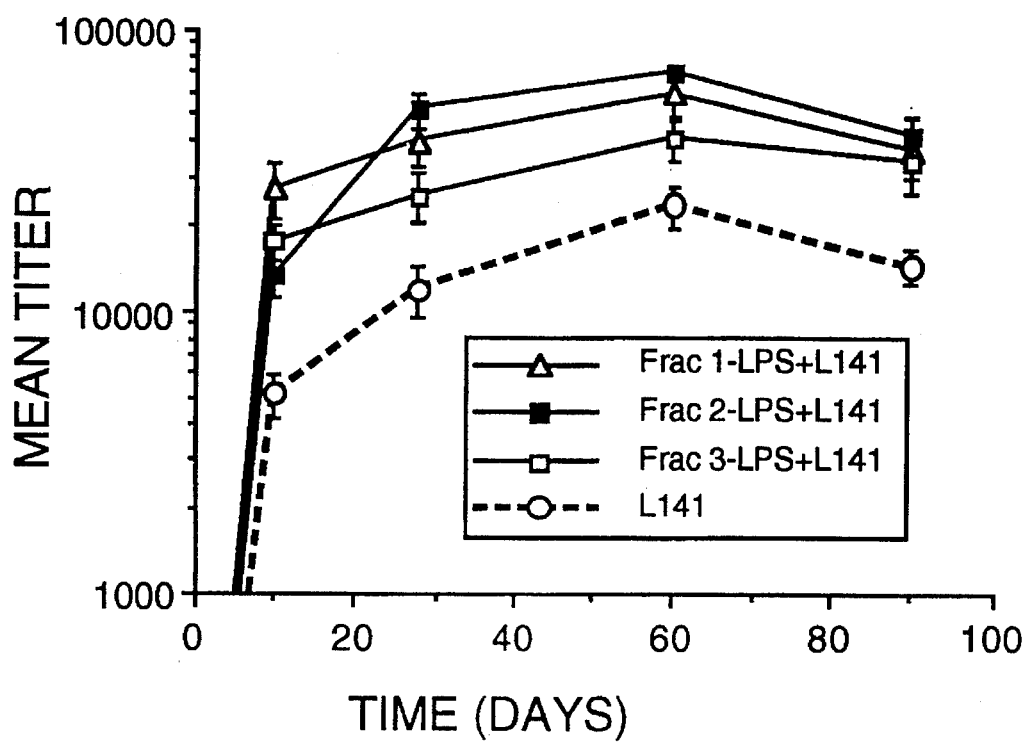
FIG. 18 shows adjuvant effect for $TNP_{10}HEA$ of fractions of the largest LPS's containing varying amounts of O-polysaccharide in combination with copolymer L141.

Similar studies are carded out with LPS preparations from mutant organisms which differed in the size of the core polysaccharide, FIG. 17. These LPS derivatives produced an increase in antibody response at 10 days after injection. The smallest preparation, Re-LPS, resulted in a suppressed response at day 60. The other derivatives produced a moderate enhancement. Finally, the adjuvant effects of fractions of LPS containing varying amounts of O-polysaccharide are evaluated in combination with copolymer L141, FIG. 18. Each of these preparations produced a rapidly increased immune response which is sustained for the entire period of measurement.

Several of the observations with each of the LPS fractions and derivatives alone and in combination with copolymer L141 are summarized in the Table 1.

TABLE 1

| LPS/lipid A precursor[1] | Source | Percent Survive[2] | Antibody Titer[3] | Day 28 Synergy Ratio[4] |
|---|---|---|---|---|
| Lipid X | E. coli MN7 | 100 | 14,201 ± 4,753 | 0.60 |
| Precursor lipid IVA | S. typhimurium i50 | 100 | 11,140 ± 2,350 | 0.50 |
| MPL | E. coli D31m4 | 100 | 27,184 ± 5,845 | 1.13 |
| Re-LPS | E. coli D31m4 | 100 | 14,985 ± 2,695 | 0.62 |
| Rd1-LPS | S. minnesota R7 | 83 | 52,925 ± 15,799 | 2.20 |
| Rc-LPS | S. typhimurium SL684 | 66 | 50,518 ± 13,555 | 2.10 |
| Rb2-LPS | S. minnesota R345 | NA | NA | NA |
| Ra-LPS | S. minnesota R60 | 16 | 72,169 ± 0 | 3.00 |
| Ra-LPS detox | E. coli EH-100 | 100 | 122,668 ± 29,635 | 5.10 |
| SR-LPS | S. typhiimurium SF1512 | 0 | NA | NA |
| R-LPS | R. sphaeroides ATCC 17023 | 100 | 21,651 ± 5,233 | 0.90 |
| S-LPS-I[5] | E. coli 09 | 100 | 81,792 ± 15,800 | 3.40 |
| S/R-LPS-II[5] | E. coli 09 | 50 | 103,443 ± 14,291 | 4.30 |
| R-LPS-III[5] | E. coli 09 | 66 | 50,518 ± 10,219 | 2.10 |
| S-LPS | E. coli 058 | 80 | 81,793 ± 18,253 | 3.40 |

[1]The structure of the various forms of LPS and lipid A are described in Materials and Methods section. S = smooth, R = rough
[2]The percent of animals which survived an injection of 100 µg of the LPS derivative in a squalane-in-water emulsion with 1.0 mg L141 and 50 µg TNP-HEA.
[3]IgG antibody titer to TNP at day 28 ± SE of animals immunized with the LPS plus L141 emulsions of TNP-HEA.
[4]The synergy ratio is the anti-TNP antibody induced by LPS plus L141 divided by that induced by similar emulsion with L141 but no LPS.
[5]The LPS from E. coli 09 was fractionated on a Bio-Gel P-100 column to yield fractions-I, -II, and -III. S = smooth; R = rough.

The titers are normalized for this table to facilitate comparison of results between experiments. A synergy ratio is calculated to evaluate the relative ability of the LPS preparations and derivatives to increase the IgG antibody response over that expected when either agent is used as an adjuvant alone. The toxicity of the immunogens containing LPS varied markedly as judged by survival. The preparations with less than 100% survival generally produced scruffled hair and other signs of endotoxin induced distress. Several of the preparations, however, produced no mortality and little clinical sign of toxicity. These included the monophosphoryl lipid A, lipid A derivatives, lipid X, lipid IVA, the detoxified Ra and the Rhodopseudomonas sphaeroides LPS. Ability of these preparations to increase the antibody response over those produced by copolymer L141 or the LPS preparation alone varied markedly among the LPS preparations used. Some of the preparations suppressed the immune response and others had little effect. However, those that did increase antibody titers, produced increases which are sustained over the three month period of observation. A particularly promising preparation is the detoxified Ra-LPS derivative which is a weak adjuvant by itself, but increased titers markedly in combination with copolymer L141. (FIG. 13)

Antibody Isotype

The isotype of antibody is determined for several of the endotoxin derivatives and fractions with reduced toxicity. (FIGS. 13 and 14). As expected, copolymer L141 by itself produced a predominant IgG1 isotype antibody response with lesser amounts of IgG2a and 2b with only a trace of IgG3. The antigen injected without adjuvant produced no detectable antibody. The LPS derivatives had a variable effect on the production of IgG1 antibody. The net result is the production of a predominant IgG2 response. Even in using preparations which produced no enhancement of antibody titers, there is a shift in isotypes away from IgG1 towards IgG2a and b.

EXAMPLE 18

Animals

Six week old, female, outbred ICR white mice are obtained from Charles River Breeding Laboratories (Raleigh, N.C.) and are allowed to acclimate in the animal facility for one week before immunizations. Food and water are available ad libitum.

Copolymers and Other Reagents

Synthetic block copolymers L121, L141, and L180.5 are obtained from CytRx Corporation, Norcross, Ga., the threonyl derivative of muramyl dipeptide (MDP) are obtained from Syntex Corporation (Palo Alto, Calif.), and the *Rhodopseudomonas sphaeroides* LPS is obtained from Dr. Kuni Takayama, VA Hospital (Madison, Wis.).

Malaria Peptide and Peptide Conjugation

The peptide (NAGG)5 is synthesized at the Microchemistry Facility at Emory University (Atlanta, Ga.) using a model 430A Peptide Synthesizer (Applied Biosystems, Inc.) and purity is evaluated by amino acid analysis and HPLC. $(NAGG)_5$ is a tandem repeat from the circumsporozoite protein of the sporozoite of *Plasmodium cynomolgi* N1H strain. Conjugation of the peptide (P) to bovine serum albumin (BSA) or hen egg albumin (HEA) (Sigma Chemical Co., St. Louis, Mo.) is carried out using a modification of the one step glutaraldehyde-coupling method of Rougon et al., 1984. Briefly, $4 \times 10^{-6}$ moles of the peptide dissolved in 0.8 ml PBS, pH 8.7 is mixed with $1.5 \times 10^{-7}$ moles BSA or HEA in 1.2 ml PBS, pH 8.7. To this mixture, 2 ml of a 0.02M solution of glutaraldehyde (Sigma Chemical Co., St Louis, Mo.) is added in aliquots of 0.05 ml over 15 minutes at room temperature, with vortexing between additions. The mixture is rotated over night at room temperature on an orbital shaker (150 rpm). Unbound glutaraldehyde and peptide are removed by passing the mixture through a Sephadex G-25 column with PBS, pH 7.3. The P-BSA or P-HEA is collected in the void volume and stored at −20° C.

ELISA Assay for Antibody Titers and Isotype Quantitation

Titers of antibody directed against the peptide are obtained using a modification of the method of Saunders.[30] Ninety six-well microtiter plates (Flow Laboratories, McLean, Va.) are coated overnight at 4° C. with 0.1 ml/well of a 0.002 mg/ml solution of peptide conjugated to hen egg albumin (P-HEA) in PBS, pH 7.3. All further incubations are carried out at room temperature. Antigen coated wells are blocked with 0.1 ml of a solution of 1% human albumin (Sigma Chemical Co., St Louis, Mo.) in PBS, pH 7.3 for 1 hour. After washing with PBS, pH 7.3 with 0.05% of the surfactant PLURONIC® F68 (poloxamer 188) 0.1 ml of serial 3-fold dilutions of plasma from immunized mice, are added to the wells in duplicate. Three-fold dilutions of mouse plasma from non-immunized mice and a monoclonal antibody directed against the peptide, $(NAGG)_5$, are also added in duplicate as ELISA negative and positive controls, respectively. The plates are incubated for 1 hour, at 200 rpm on an orbital shaker. After washing, 0.1 ml of a peroxidase conjugated goat anti-mouse IgG, IgG1, IgG2a, or IgG2b diluted 1:2000 or anti-IgG 3 (FisherBiotech, Orangeburg, N.Y.) diluted 1:1000 are added to each well and incubated for 1½ hours, at 200 rpm. After washing again, 0.1 ml of 2.5 mg/ml orthophenylene diamine (Sigma Chemical Co., St Louis, Mo.) and 0.03% hydrogen peroxide (Sigma Chemical Co., St Louis, Mo.) in citrate buffer, pH 5.0, are added to each well, incubated for 15 minutes, and the color reaction is stopped with 2.5M sulfuric acid. The absorbance at 490 nm is determined using a BioRad Microplate Reader and the titers are determined by regression analysis, using the dilution resulting in an absorbance value of 1. Isotype quantitation is done by converting the ELISA titers to nanograms per milliliter plasma of each subclass by referring to a standard curve. Ten micrograms per ml of a polyclonal goat anti-mouse IgG (Fisher Biotech, Orangeburg, N.Y.), diluted in PBS, pH 7.3, is used to coat the wells of a 96 well microtiter plate. Washing, blocking, and incubation times are the same as those in the ELISA assay above. Dilutions of mouse myeloma proteins of each isotype (Sigma Chemical Co., St Louis, Mo.) are used as standards. A goat anti-mouse iso-type-specific horse radish peroxidase conjugate (FisherBiotech, Orangeburg, N.Y.) is used to determine the absorbance of the standards at concentrations of 119 ng–0.03 ng. The concentrations of iso-type-specific standards, resulting in an absorbance value of 1, are determined from standard curves of the absorbance (490 nm) versus the concentration, by regression analysis. The concentration of peptide-specific isotype at an absorbance of 1, is multiplied by the ELISA titer at an absorbance of 1, to give the concentrations in ng/ml.

[30]Saunders, supra

Flagella Preparation

*Salmonella typhi*, strain TY2 (type 29), is obtained from the American Type Culture Collection. Frozen stock cultures are grown on Tryptic Soy Agar plates (Difco Laboratories, Detroit, Mich.) and passaged 4–5 times through 0.3% Tryptic Soy Motility Agar. The highly motile bacteria are selected because they produce the most flagella. Organisms are inoculated into Tryptic Soy Broth and incubated at 37° C. for 6 hours. Aliquots of the broth suspension of bacteria are inoculated onto Mueller Hinton Agar plates (Carr Scarlborough) incubated at 37° C. for 16 hours. The cells are harvested off the plates with PBS containing 0.1% thimerosal (Sigma Chemical Co., St Louis, Mo.). The flagella are removed from the cells by vigorous shaking for 20 minutes in a mechanical shaker (Red Devil Paint Shaker) and separated from the cell bodies by differential centrifugation as follows: the cell bodies are pelleted by centrifugation at 6000×9 for 30 minutes in a Sorvall RC-5B refrigerated Superspeed Centrifuge (DuPont Instruments) with a GSA rotor, followed by centrifugation at 16,000×9 for 10 minutes to pellet broken cells and other small debris. Flagella are then pelleted at 90,000×9 in a Beckman L8-70M ultracentrifuge with a SW27 swing bucket rotor, resuspended in thimerosal-PBS, repelleted, and resuspended in thimerosal-PBS. Protein concentration is determined by Lowry's Protein Determination.[31] Aliquots of 5.2 mg/ml flagella are frozen at −70° C.

[31]Lowry, O. H., et al., "Protein measurement with the folin phenol reagent", *J. Biol. Chem.*, Vol. 193, pgs. 265–275 (1951)

Flagella Conjugation

Conjugation of the peptide to Salmonella flagella (P-flagella) is performed using an adaptation of the two step glutaraldehyde-coupling procedure of Liang et al.[32] The peptide ($1.5 \times 10^{-7}$ moles) dissolved in 1.2 ml PBS, pH 8.7, are treated with an equal volume of 0.02M gluteraldehyde, added in aliquots of 0.05 ml with vortexing between additions, and allowed to rotate over night at room temperature on an orbital shaker (150 rpm). After overnight dialysis against PBS at 4° C. to remove unreacted glutaraldehyde, either $4 \times 10^{-6}$, $2 \times 10^{-6}$, or $1 \times 10^{-6}$ moles of peptide in 0.8 ml PBS, pH 8.7, representing peptide to flagella molar ratios of 26:1, 13:1, and 6.5:1, respectively, are added to the dialyzed flagella. The mixture is rotated overnight at room temperature. Unbound peptide is separated from flagella by ultracentrifugation at 90,000×9 for 1 hour in a Beckman L8- 70M ultracentrifuge with an SW27 swing bucket rotor. The flagella pellet is resuspended in PBS, pH 7.3, recentrifuged, resuspended in PBS, followed by the addition of 0.02M lysine (Sigma Chemical Co., St Louis, Mo.). This is allowed to react over night at 4° C., followed by recentrifugation, and resuspension in 2 ml PBS.

[32]Liang et al., "Oral Administration of Cholera Toxin-Sedai Virus Conjugate Potentiates Gut and Respiratory Immunity Against Sendai Virus", *J. Immunol.*, Vol. 141, No. 5, pgs. 1495–1501 (1988)

Emulsions and Mode of Immunization

Groups of 5–8 mice are immunized with oil-in-water emulsions containing a mixture of 2% squalane (Sigma Chemical Co., St Louis, Mo.) and PBS, pH 7.2 with 0.2% Tween-80 (Sigma Chemical Co., St Louis, Mo.). When present, copolymer adjuvants L121 or L141, are at a concentration of 1 mg/0.04 ml, *R. sphaeroides* LPS at 0.1 mg/0.04 ml, and lyophilized peptide or PBSA at 0.1 mg/0.04 ml or P-flagella at 0.05 mg/0.05 ml. All emulsions are prepared with the same concentrations except for one experiment where the P-BSA is present at 0.05 ml. The lyophilized antigen is mixed for 2 minutes with squalane and copolymer in a 2 ml glass homogenizer with a motorized pestle. The aqueous phase and additional adjuvants are added to the oil phase and emulsified for an additional 2 minutes for all experiments except one, where the P-BSA or P-flagella is not lyophilized but added in PBS to the aqueous phase. Either 0.04 ml of emulsion containing 0.1 mg P-BSA is injected into a single hind footpad, or 0.025 ml P-BSA or P-flagella (0.05 mg/ml) is injected into each hind footpad. In an experiment comparing routes of immunization, 0.1 mg P-BSA in either 0.04 ml of a squalane-in-water emulsion, with and without L121 or L141, is injected into a single hind footpad (FP), or in 0.2 ml of emulsion IP or SC. All mice are given a second immunization on day 29 with either the same amount of the identical formulation, antigen and L121 in an oil-in-water emulsion, or antigen in PBS. In a single experiment, three groups of mice are given a third immunization with P-BSA in an oil-in-water emulsion containing L121. Most groups of mice are bled from the retro-orbital plexis into heparinized tubes on days 0, 10, 28, and 36 after primary immunization. In the time course experiment, plasma is collected on days 10, 28, 60, 90, 97, 111, 141, 171, 201, 207, and 214 after primary immunization. Plasma from each mouse is assayed individually by ELISA and the means and standard errors are determined for each group.

EXAMPLE 19

Eight mice per group are immunized with 0.1 mg peptide or peptide-BSA emulsified in 2% squalane-in-water, with or without copolymers and/or *R. sphaeroides* LPS at 0.1 mg per mouse. All mice are given a second immunization at one month and plasma is collected after one week. Assays for peptide-specific total IgG and IgG isotypes are performed as described hereinabove. Total IgG antibody titers are shown as the mean +SEM of each group. The results are summarized in Table 2.

TABLE 2

| | Titer | Isotype (%) | | | |
|---|---|---|---|---|---|
| | IgG | IgG1 | IgG2a | IgG2b | IgG3 |
| Peptide | 33 | 100 | 0 | 0 | 0 |
| Peptide-BSA | 2205 ± 1732 | 99.3 | 0 | 0.7 | 0 |
| +R. sph-LPS | 7529 ± 1996 | 96.8 | 0.1 | 2.5 | 6.6 |
| +L121 | 17240 ± 3156 | 83.4 | 2.4 | 12.4 | 1.8 |
| +L141 | 17641 ± 7527 | 86.2 | 9.1 | 4.6 | 0 |
| +L121 + LPS | 13105 ± 2384 | 66.2 | 8.0 | 24.7 | 0.2 |
| +L141 + LPS | 48435 ± 13283 | 51.4 | 6.8 | 39.1 | 2.8 |

Malaria peptide alone produced a barely detectable response which is 100% IgG1. Peptide conjugated to BSA produced an almost 2 log-higher IgG response, nearly all of which is IgG1, with less than 1% IgG2b. Addition of LPS to peptide-BSA produced a 3.4 fold increased in total IgG, most of which is IgG1, with 2.5% IgG2b and barely detectable levels of IgG2a and IgG3. Addition of either copolymer to peptide-BSA produced over a 7 fold increase in total IgG and significant amounts of IgG2b and IgG2a. With L121, small amounts of IgG3 are also present.

When LPS is added with L121 and peptide-BSA, the proportion of IgG2b is nearly doubled and the IgG2a increased to 8% of total IgG, although the total IgG titer is slightly less than without LPS. L141 and LPS showed synergy, both with respect to producing nearly a 3 fold increase in total IgG titer and in their influence on subclass distribution. The proportion of IgG2b increased more than 8 fold above that with L141 alone, rising to over 39% of total IgG. Significant amounts of IgG2a are present, and this adjuvant combination produced a proportion of IgG3 of 2.8%.

EXAMPLE 20

Effect of Hapten Density on the Distribution of IgG Isotypes

The effect of different molar ratios of peptide per flagellin monomer, using dry preparations with L121 is examined. Groups of mice are immunized with emulsions containing 0.05 mg peptide-flagella at molar ratios of 26:1, 13:1, and 6.5:1 distributed into both hind footpads. The mice are boosted at one month with peptide-flagella of the same hapten density dissolved in saline. Plasma is collected after one week and assayed for concentrations of peptide-specific IgG isotypes.

Figure 19:
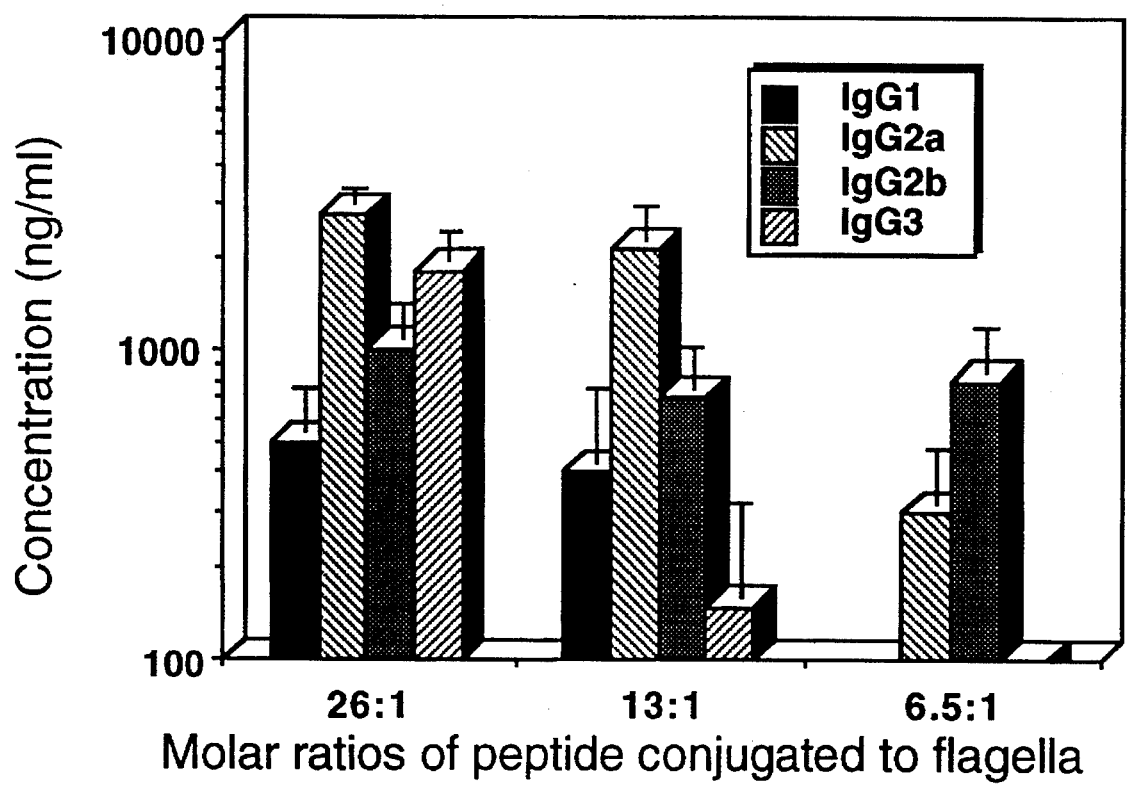
FIG. 19 shows the changes in intensity and IgG isotype distribution to different molar ratios of peptide conjugated to flagella.

Changes in the molar ratio of peptide to flagella influenced both the intensity of the IgG antibody response and the isotype distribution (FIG. 19). Increasing the molar ratio increased the total IgG concentration 6-fold between 6.5:1 and 26:1 and significantly changed the isotype pattern. Flagella with a 26:1 peptide ratio induced 11% IgG1, 43% IgG2a, 17% IgG2b and 29% IgG3. Reducing the peptide ratio to 13:1 almost exclusively affected IgG3, decreasing its proportion to 4%. Lowering the ratio to 6.5:1 eliminated IgG1 and IgG3 and reduced the concentration of IgG2a.

EXAMPLE 21

Animals

Seven to ten week old female ICR (outbred) mice from Charles River Laboratories are used as test animals. All copolymers are obtained from CytRx Corporation, Atlanta, Ga. TNP-HEA (Sigma Chemical Company, St. Louis, Mo.) is prepared according to the procedure in Methods in Immunology.[33]

[33]Justine S. G., et al., supra

Emulsion Preparation

Emulsions are 1 ml final volume and an 0.04 ml injection volume. Add indicated amount of TNP-HEA (lyophilized), 0.05 mg/mouse. Add 2% squalane in saline. Add indicated amount of copolymer at an amount of 1.0 mg/mouse. Homogenize the mixture for 2 minutes. Quantity sufficient to 1 ml using PBS/Tween-80 (0.2%). Homogenize for approximately 2 minutes at room temperature Injections Mice receive initial subcutaneous injection (0.04 ml) in hind footpad. A booster is given on day 90 in some cases—Antigen+Copolymer.

Footpad Measurements

Baseline measurements are made prior to injections. Following injections, measurements are made at specific time points until intimation subsides.

Blood Collection

Blood for plasma antibody detection is collected at specific time points throughout the course of the study. This is done via retro-orbital plexus using heparinized Natelson tubes. Samples are centrifuged for 15 minutes at 2500 rpm. Serum is stored at −70 C.

TABLE 3

| Copolymer | MW POP | % POE | IgG Antibody Day 28 | Titers Day 97 |
|---|---|---|---|---|
| L101 | ≈3250 | ≈10 | 24875 ± 8751 | 267919 ± 82631 |
| L121 | ≈4000 | ≈10 | 11828 ± 4407 | 209891 ± 120490 |
| L122 | ≈4000 | ≈20 | 184 ± 45 | |
| L141 | ≈4600 | ≈10 | 112431 ± 22728 | 510272 ± 125563 |
| L180.5 | ≈5200 | ≈5 | 307863 ± 66575 | 360072 ± 77470 |
| L181.5 | ≈5200 | ≈15 | 6715 ± 1604 | 152367 ± 33649 |
| P182.5 | ≈5200 | ≈25 | 1500 | |

Groups of five to ten mice are immunized with TNP-HEA in a 2% squalane-in-water emulsion containing 1 mg of each of the copolymers shown in Table 3. The time course of the antibody responses are similar in each of the groups. The titers peaked at approximately one month after injection and persisted for several months. The animals are boosted after three months. There are bled again one week later. The copolymers with 10% polyoxyethylene and molecular weights of polyoxypropylene equal or less than 4600 induced strong immune responses. The larger preparations with polyoxypropylene molecular weights of 5200 are effective adjuvants only with a smaller proportion of polyoxyethylene. The preparations with larger portions of polyoxyethylene are much less effective.

EXAMPLE 22

The following example compares one of the formulations contemplated as part of the present invention with prior art adjuvants. The formulation has the following general formula:

| Component | Concentration by weight |
|---|---|
| Squalene | 85% |
| Span 80 (Sorbitan monooleate) | 10% |
| Silica (5μ particles) | 1% |
| PLURONIC ® L141 | 4% |

Silica and copolymer are combined first and mixed thoroughly until silica is completely coated with the copolymer. Then the Span 80 and squalene is added and mixed for approximately 45 min with a magnetic stirrer. Prepare a water-in-oil emulsion with 50% water with the antigen is in the water.

Other adjuvants that are used in this example include RAS from Ribi Immunochem Research, Inc. Hamilton Mont., ADJUVAX™, Alpha-Beta Technology, Inc. Worcester, Mass. and Freund's Complete Adjuvant (Sigma Chemical Co. St. Louis, Mo. All adjuvants were prepared according to the manufacturer's instructions and administered as indicated.

Groups of female New Zealand White rabbits (N=4) were immunized with a peptide protein conjugate (luteinizing hormone releasing hormone-bovine serum albumin, LHRH-BSA) as follows:

| Adjuvant | Administration |
|---|---|
| Present invention (boosted) | 50 μg of antigen intramuscularly (IM) in each hind flank (25 μg antigen/25 μl emulsion × 2 injections) on day 1<br>50 μg of antigen intramuscularly (IM) in each hind flank (25 μg antigen/25 μl emulsion × 2 injections) on day 28 |
| Present invention | 50 μg of antigen intramuscularly (IM) in each hind flank (25 μg antigen/25 μl emulsion × 2 injections) on day 1 only |
| Freund's Adjuvant | 50 μg of antigen intramuscularly (IM) in each hind flank (25 μg antigen/250 μl emulsion × 2 injections) on day 1 in complete Freund's adjuvant |
| ADJUVAX ™ | 50 μg of antigen emulsified and injected according to manufacturer's instructions: 50 μg of antigen subcutaneously (SQ) in 2 sites (25 μg antigen/200 μl adjuvant × 2 injections) on days 1, 28 and 35 |
| RAS, Ribi | 50 μg of antigen emulsified and injected according to manufacturer's instruction. 50 μg antigen/1 ml emulsion as follows:<br>0.3 ml intradermal (50 μl × 6 sites)<br>0.4 ml intramuscular (0.2 ml/each hind flank)<br>0.1 ml subcutaneous in neck region<br>0.2 ml intraperitoneal on days 1 and 21 |

Figure 20:
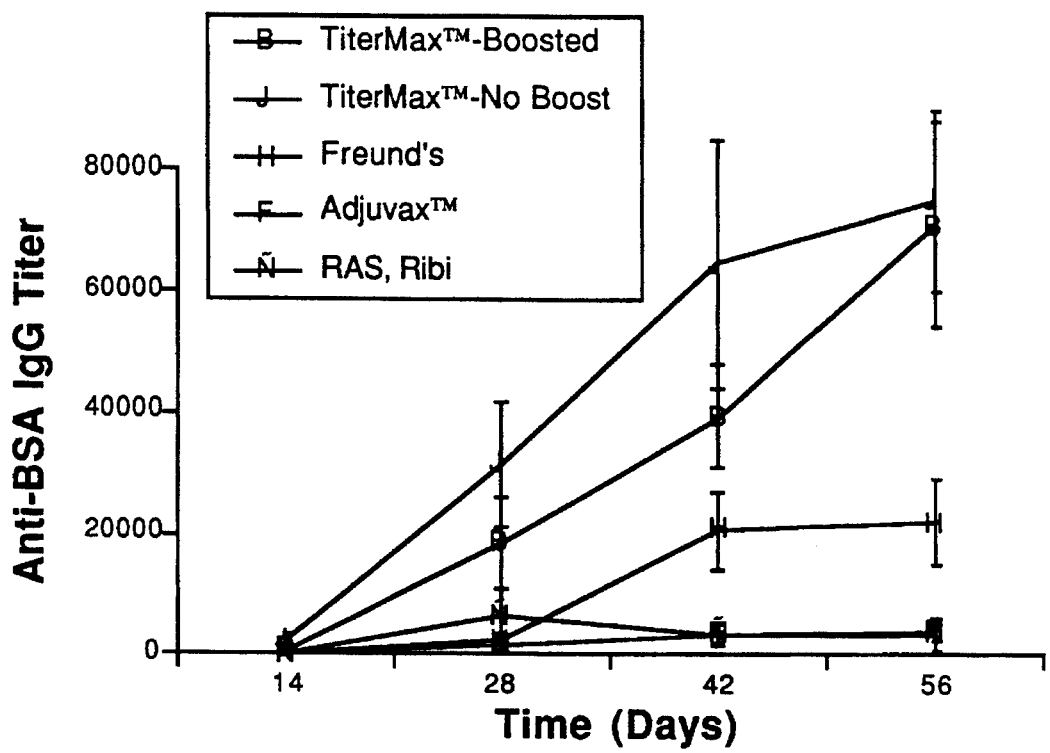
FIG. 20 shows a comparison between an adjuvant preparation according to the present invention and several commercially available adjuvant preparations.

The anti BSA antibody titer at 14, 28, 42 and 56 days for each of the adjuvants is shown in FIG. 20. As can be seen in FIG. 20, on day 56, the fomulation according to the present invention produced titers that were 3 to 4 times that of Freund's Complete Adjuvant. The volume of the fomulation according to the present invention is only one fifth the injected volume of Freund's Adjuvant. The formulation according to the present invention is significantly less toxic than Freund's complete adjuvant. In other species, the immune response seen with the fomulation according to the present invention was at least equal to or greater than that seen with Freund's.

EXAMPLE 23

Copolymer L180.5 is found to have surprising physical properties which make it an effective adjuvant without oil. The copolymer is insoluble at room temperature, but is soluble at refrigerator (≈4° C.) temperatures. Unlike the smaller adjuvant molecules such as L101, L121 and L141, the insoluble form at room temperature is a small particulate stable suspension. The smaller copolymers all form unstable suspension which coalesce into large amorphous masses. Such preparations are poor candidates for vaccine adjuvants. The following Example demonstrates the ability of copolymer 180.5 to serve as an adjuvant by itself, or in combination with detoxified Ra-LPS without oil. 0.1 ml of $TNP_{10}$-HEA (25 mg/ml) is mixed with 0.4 ml of copolymer L180.5 (125 mg/ml). The mixture is placed in the refrigerator until the copolymer goes into solution. It is then removed and warmed to room temperature slowly to facilitate the binding of antigen to the copolymer particles. A similar preparation was prepared identically except that an appropriate amount of detoxified Ra-LPS is added. Groups of 6 mice are immunized in the rear foot pad with 50 µg of $TNP_{10}$-HEA, 1 mg of copolymer 180.5 and 10 µg of LPS. Some of the groups are boosted with similar injections at day 18. The are bled for antibody determinations on days 24 and 72. The results are summarized in Table 4:

TABLE 4

| Adjuvant | IgG Antibody Titers | | | |
|---|---|---|---|---|
| | Day 24 | ±SE | Day 72 | ±SE |
| L180.5 | 184 | ±80 | 462 | ±288 |
| L180.5 boosted | 1155 | ±255 | 577 | ±274 |
| LPS | 387 | ±18 | 413 | ±158 |
| L180.5 + LPS | 80136 | ±19207 | 51869 | ±18571 |
| None | <20 | | <20 | |

The copolymer without oil induced a persistent and moderately strong primary and secondary antibody response. In the presence of LPS, the copolymer primed animals for a very strong secondary response. Similar injections of antigen without adjuvant failed to induce detectable primary responses and only very weak secondary responses.

EXAMPLE 24

In another experiment, animals are immunized with $10^7$ whole killed blood stage parasites of a mouse malaria (*Plasmodium yoelii*) in adjuvants containing 1 mg of copolymer L180.5 by itself or with 10 µg of detoxified Ra-LPS or squalane-in-water emulsions of 1 mg of copolymer L180.5 by itself or with 10 µg of detoxified Ra-LPS. The squalane, copolymer, LPS and antigen are combined in a homogenizer before adding 0.5% Tween 80 saline to form a oil in water emulsion. Animals are boosted on day 35 and challenged with 104 virulent blood stage plasmodium organisms on day 70. The control animals and those immunized with the antigen in Freund's complete adjuvant developed progressive malaria infections. Animals immunized with the antigen in any of the four adjuvants containing L180.5 with or without LPS were protected. Protection is defined as parasitemia less than 10% of the red blood cells and falling at 14 days after infection.

Protection correlated with antibody of the IgG2a isotype to epitopes on the surface of the parasites. This study demonstrates that adjuvants containing the copolymer with or without oil or LPS are able to induce protective immune responses to malaria and are more effective than Freund's complete adjuvant. They also induce high antibody titers.

EXAMPLE 25

Experiments were done with a recombinant protein of human immunodeficiency virus (Gp120 of HIV). Mice are immunized with 25 µg Gp120 in squalane-in-water or no oil formulations of 1 mg copolymer L180.5 with or without 10 µg detoxified RaLPS. The squalane, copolymer, LPS and antigen are combined in a homogenizer before adding 0.5% Tween 80 saline to form a oil in water emulsion. All groups are boosted once on day 28. The titers to the HIV protein on day 42 are shown in the following Table 5:

TABLE 5

| | IgG Titers to HIV Gp120 | |
|---|---|---|
| Adjuvant | Day 42 | ±SE |
| o/w L180.5 | 6767 | 3689 |
| o/w L180.5 + LPS | 63818 | 18226 |
| L180.5 | 7023 | 3100 |
| L180.5 + LPS | 26429 | 21395 |
| none | 4217 | 2216 |

EXAMPLE 26

Figure 21:
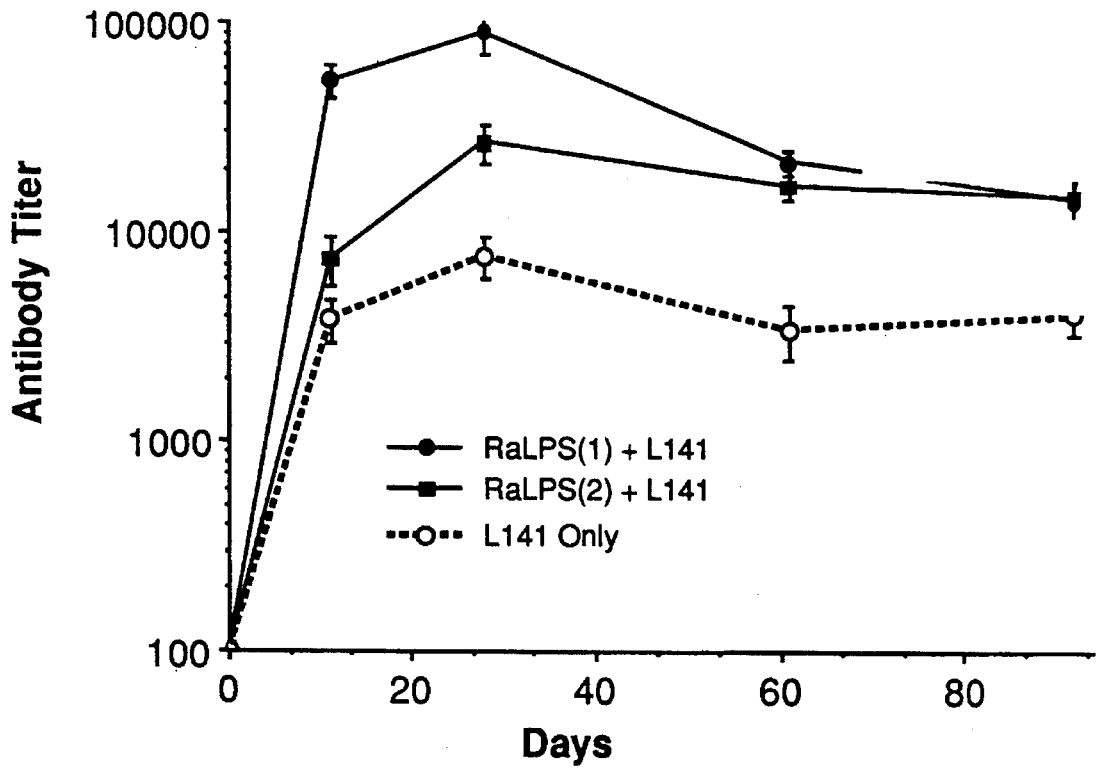
FIG. 21 shows the effect of detoxified LPS on an immune response.

Two preparations of RaLPS were prepared. One was detoxified by treatment for 30 minutes with borate. The second was detoxified by treatment for 7 hours with borate. Groups of 6 female ICR mice were immunized with 50 µg of each RaLPS in an oil and water emulsion of 50 µg $TNP_{10}HEA$. one mg copolymer L141, 5 mg of squalane which was suspended in 0.5% Tween 80 saline. The squalane, copolymer, LPS and antigen are combined in a homogenizer before adding 0.5% Tween 80 saline to form a oil-in-water emulsion. The injection volume was 50 µl per animals. The animals were bled at intervals for IgG antibody titers measured by ELISA. As shown in FIG. 21, the mildly detoxified preparation of LPS produced a higher early response while the more extensively detoxified preparation produced modest increase early but a sustained production comparable to the partially detoxified LPS preparation or fully toxic LPS preparation. This is in striking contrast to previous studies with MPL and other LPS preparations without core polysaccharides which produced early increase in titers but suppressed titers late as compared with the emulsion without LPS.

EXAMPLE 27

Figure 22:
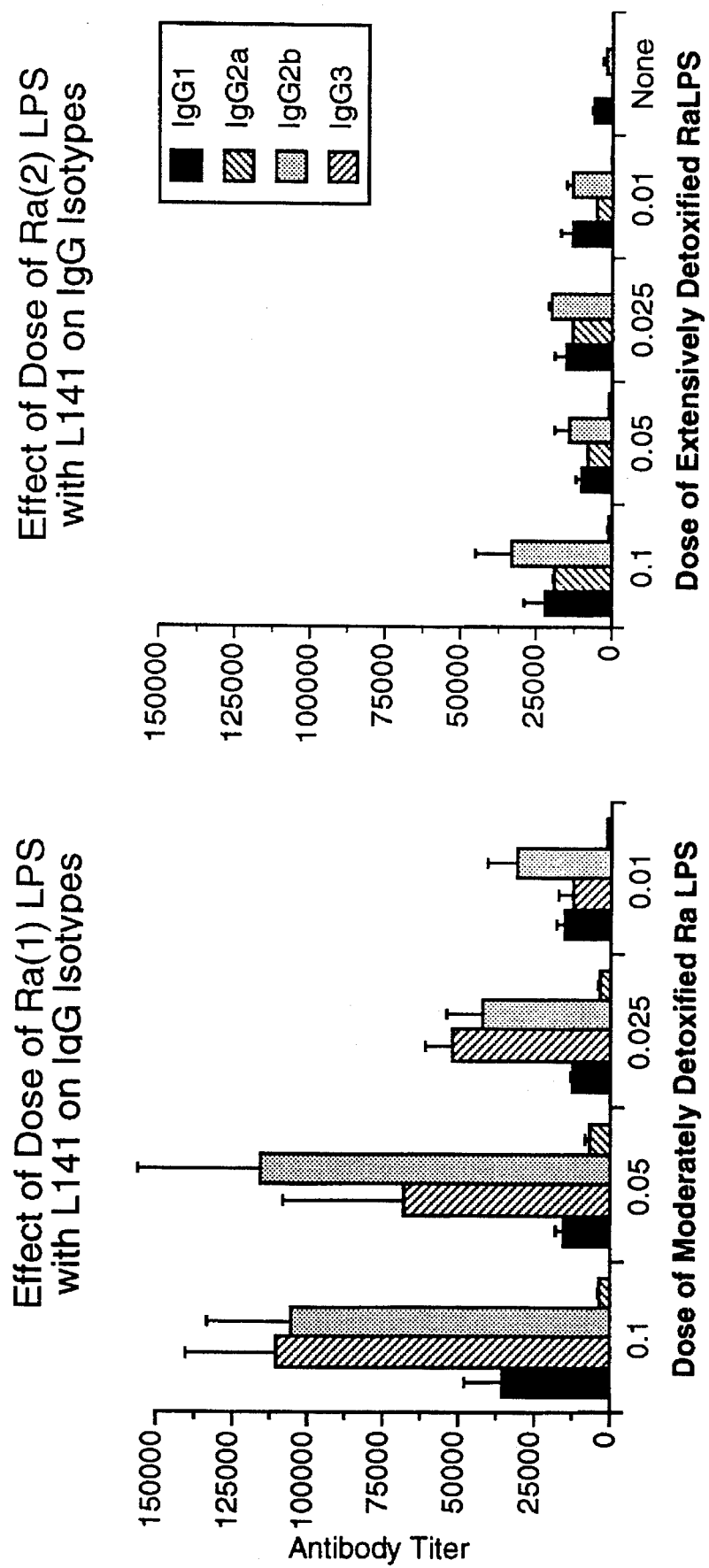
FIG. 22 shows dose response of detoxified LPS.

Animals were immunized with formulations identical to those described in Example 26 with doses of mildly or extensively detoxified RaLPS of 0.1, 0.05, 0.025, and 0.01 µg. Animals were bled for determination of IgG isotypes on day 28. As shown in FIG. 22, all doses of both preparations produced increases in all isotypes. The increase in IgG2a was dose dependent on the mildly detoxified RaLPS. The increase in IgG2b was partially dose dependent, while that in IgG1 was relatively independent of dose within the range tested. Surprisingly, the high dose of extensively detoxified produced a pattern of Isotype changes comperable to that of the lowest dose of the partially detoxified RaLPS. This demonstrates that the modulation of isotype can be controlled or optimized for particular applications by either the dose or extent of detoxification of the LPS.

EXAMPLE 28

Figure 23:
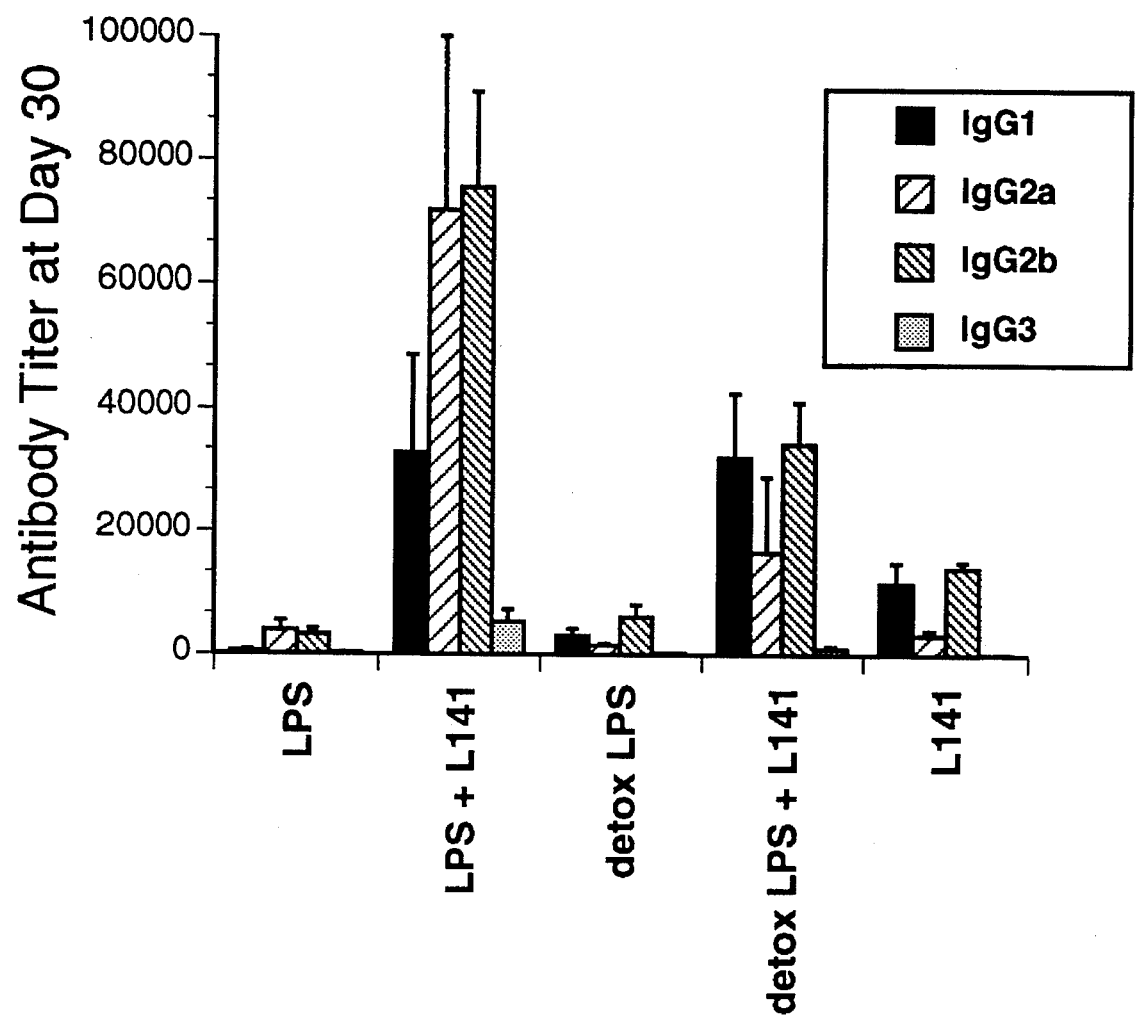
FIG. 23 shows the effect of LPS plus L141 on an immune response.

Experiments were done to test the adjuvant activity of LPS from Pseudomonas which inherently has low toxicity. This low toxicity may be due to the fact that the LPS from Pseudomonas has been reported to have only 5 fatty acids which have a carbon chain length of 10. LPS was isolated from *Pseudomonas aeruginosa* by standard procedures. A sample of the LPS was detoxified by treatment with TEA as described previously. Groups of 6 ICR female mice immunized with 50 µg of LPS, 50 µg $TNP_{10}HEA$. one mg copolmer L141, 5 mg of squalane which was suspended in 0.5% Tween 80 saline or similar emulsions without the L141 or without the LPS as indicated in FIG. 23. The squalane, copolymer, LPS and antigen are combined in a homogenizer before adding 0.5% Tween 80 saline to form a oil in water emulsion. The LPS was a weak adjuvant by itself but produced striding synergy when combined with L141 especially for the IgG2a and IgG2b isotypes. It functions similarly to the mildly detoxified RaLPS in Example 27. The detoxified Pseudomonas LPS functions similarly to the extensively detoxified RaLPS in Example 27.

EXAMPLE 29

Figure 24:
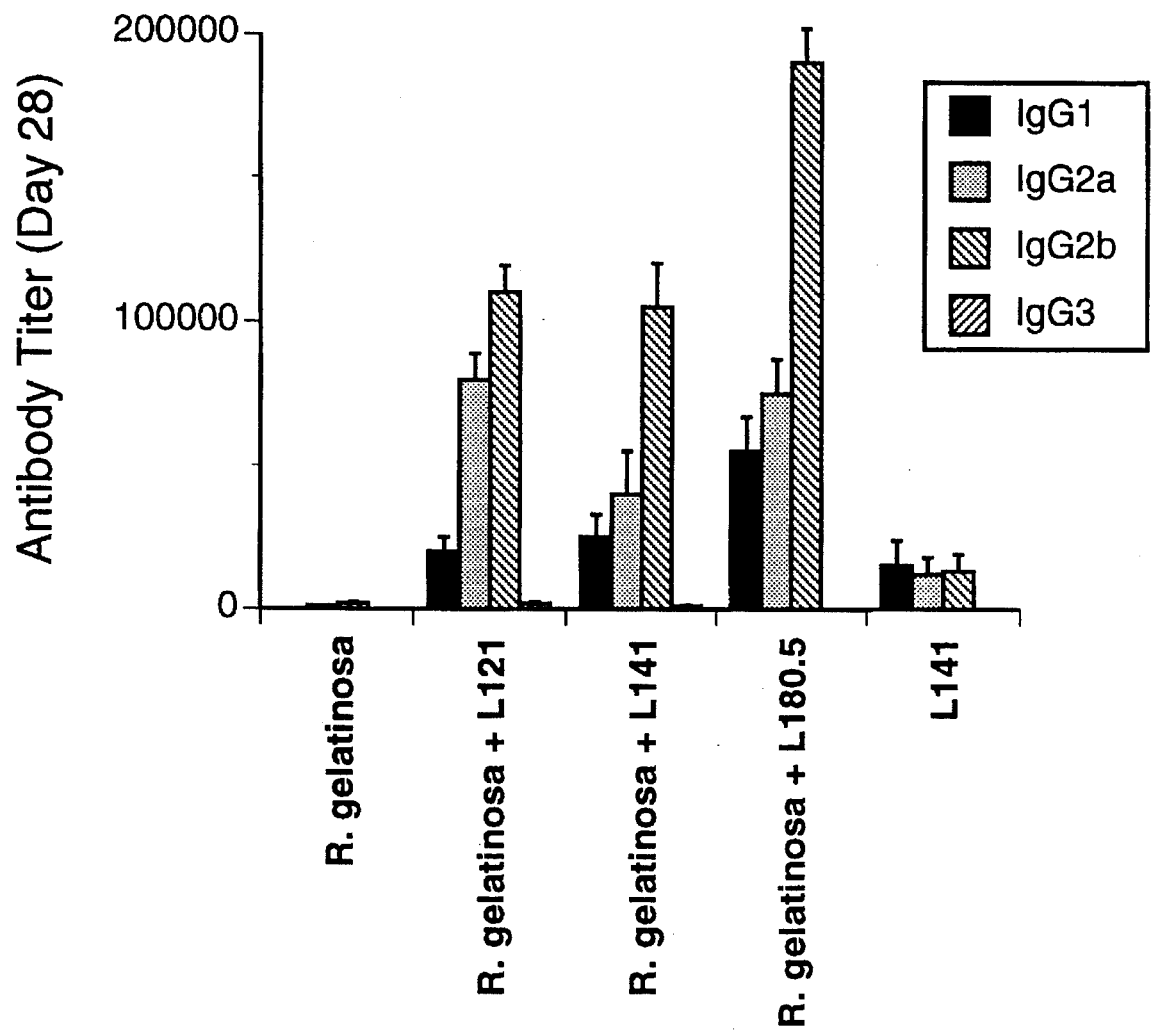
FIG. 24. shows the effect of LPS isolated from *R. gelatinosa* in combination with L141 on an immune response.

LPS was purified from the *R. gelatinosa* which is inherently intermediate in toxicity. Groups of 6 ICR female mice immunized with 50 μg of LPS, 50 μg $TNP_{10}HEA$. One mg copolymer L121, L141, L180.5, 5 mg of squalane which was suspended in 0.5% Tween 80 saline. The squalane, copolymer, LPS and antigen are combined in a homogenizer before adding 0.5% Tween 80 saline to form a oil in water emulsion. As indicated in FIG. 24, the copolymers L121 and L180.5 induce responses similar to those shown for L141. The combination of *R. gelatinosa* LPS with each of these copolymers produced large increases in IgG2a and IgG2b isotypes, but a small or no increase in IgG1. Furthermore, copolymer L180.5 was the most effective.

EXAMPLE 30

Groups of 5 Rhesus monkeys were immunized with an antisporozoite malaria vaccine consisting of a synthetic peptide (NAGG)5 conjugated to diphtheria toxoid, copolymer 180.5 and detoxified RaLPS. The squalane, copolymer, LPS and antigen are combined in a homogenizer before adding 0.5% Tween 80 saline to form a oil in water emulsion. The animals were give three subcutaneous injections at two week intervals each consisting of 100 μg of peptide conjugate, 100 μg of RaLPS, 5 mg copolymer 180.5 in a 2% squalane in water emulsion. All animals demonstrated high IgG antibody titers (OD approximately 3 at a 1 to 500 dilution by ELISA). Antibody titers by immunofluorescence against surface epitopes of sporozoites demonstrated a mean IgG antibody titer of 10,0000. Local reactions at the site of immunization were not detectable at two weeks after immunization and them was no evidence of systemic toxicity.

It should be understood that the foregoing relates only to a preferred embodiment of the present invention and that numerous modifications or alterations may be made without departing from the spirit and scope of the invention as set forth in the appended claims.

I claim:

1. A method of increasing the immune response in a human or animal to an antigen comprising the step of:

administering an admixture of antigen and adjuvant to an human or animal, wherein the adjuvant comprises:
a surface-active copolymer with the following formula:

$$HO(C_2H_4O)_b(C_3H_6O)_a(C_2H_4O)_bH$$

wherein the molecular weight of the hydrophobe $(C_3H_6O)$ is between approximately 2000 to 5100 and the percentage of hydrophile $(C_2H_4O)$ is between approximately 3% and 15% by weight, excluding a copolymer having the molecular weight of the hydrophobe $(C_3H_6O)$ of 4000 and the percentage of hydrophile $(C_2H_4O)$ of 10% by weight.

2. A vaccine comprising an admixture of a concentration of an antigen and an adjuvant effective to elicit an immune response when administered to an human or animal, the adjuvant comprising a surface-active copolymer with the following formula:

$$HO(C_2H_4O)_b(C_3H_6O)_a(C_2H_4O)_bH$$

wherein the molecular weight of the hydrophobe $(C_3H_6O)$ is between approximately 2000 and 5100 and the percentage of hydrophile $(C_2H_4O)$ is between approximately 3% and 15% by weight, excluding a copolymer having the molecular weight of the hydrophobe $(C_3H_6O)$ of 4000 and the percentage of hydrophile $(C_2H_4O)$ of 10% by weight.

3. A method of increasing the immune response in a human or animal to an antigen comprising the step of:

administering an admixture of antigen and adjuvant to an human or animal, wherein the adjuvant comprises:
a surface-active copolymer with the following formula:

$$HO(C_2H_4O)_b(C_3H_6O)_a(C_2H_4O)_bH$$

wherein the molecular weight of the hydrophobe $(C_3H_6O)$ is between approximately 2000 to 5000 and the percentage of hydrophile $(C_2H_4O)$ is between approximately 3% and 15% by weight, excluding a copolymer having the molecular weight of the hydrophobe $(C_3H_6O)$ of 4000 and the percentage of hydrophile $(C_2H_4O)$ of 10% by weight.

4. A method of increasing the immune response in a human or animal to an antigen comprising the step of:

administering an admixture of antigen and adjuvant to an human or animal, wherein the adjuvant comprises:
a surface-active copolymer with the following formula:

$$HO(C_2H_4O)_b(C_3H_6O)_a(C_2H_4O)_bH$$

wherein the molecular weight of the hydrophobe $(C_3H_6O)$ is between approximately 4000 to 9000 and the percentage of hydrophile $(C_2H_4O)$ is between approximately 3% and 15% by weight, excluding a copolymer having the molecular weight of the hydrophobe $(C_3H_6O)$ of 4000 and the percentage of hydrophile $(C_2H_4O)$ of 10% by weight.

5. A method of increasing the immune response in a human or animal to an antigen comprising the step of:

administering an admixture of antigen and adjuvant to an human or animal, wherein the adjuvant comprises:
a surface-active copolymer with the following formula:

$$HO(C_2H_4O)_b(C_3H_6O)_a(C_2H_4O)_bH$$

wherein the molecular weight of the hydrophobe $(C_3H_6O)$ is between approximately 4000 to 8000 and the percentage of hydrophile $(C_2H_4O)$ is between approximately 3% and 15% by weight, excluding a copolymer having the molecular weight of the hydrophobe $(C_3H_6O)$ of 4000 and the percentage of hydrophile $(C_2H_4O)$ of 10% by weight.

6. A vaccine comprising an admixture of a concentration of an antigen and an adjuvant effective to elicit an immune response when administered to an human or animal, the adjuvant comprising a surface-active copolymer with the following formula:

$$HO(C_2H_4O)_b(C_3H_6O)_a(C_2H_4O)_bH$$

wherein the molecular weight of the hydrophobe ($C_3H_6O$) is between approximately 2000 to 5000 and the percentage of hydrophile ($C_2H_4O$) is between approximately 3% and 15% by weight, excluding a copolymer having the molecular weight of the hydrophobe ($C_3H_6O$) of 4000 and the percentage of hydrophile ($C_2H_4O$) of 10% by weight.

7. A vaccine comprising an admixture of a concentration of an antigen and an adjuvant effective to elicit an immune response when administered to an human or animal, the adjuvant comprising a surface-active copolymer with the following formula:

$$HO(C_2H_4O)_b(C_3H_6O)_a(C_2H_4O)_bH$$

wherein the molecular weight of the hydrophobe ($C_3H_6O$) is between approximately 4000 to 9000 and the percentage of hydrophile ($C_2H_4O$) is between approximately 3% and 15% by weight, excluding a copolymer having the molecular weight of the hydrophobe ($C_3H_6O$) of 4000 and the percentage of hydrophile ($C_2H_4O$) of 10% by weight.

8. A vaccine comprising an admixture of a concentration of an antigen and an adjuvant effective to elicit an immune response when administered to an human or animal, the adjuvant comprising a surface-active copolymer with the following formula:

$$HO(C_2H_4O)_b(C_3H_6O)_a(C_2H_4O)_bH$$

wherein the molecular weight of the hydrophobe ($C_3H_6O$) is between approximately 4000 to 8000 and, the percentage of hydrophile ($C_2H_4O$) is between approximately 3% and 15% by weight, excluding a copolymer having the molecular weight of the hydrophobe ($C_3H_6O$) of 4000 and the percentage of hydrophile ($C_2H_4O$) of 10% by weight.

* * * * *